(12) United States Patent
Wong et al.

(10) Patent No.: US 8,926,975 B2
(45) Date of Patent: Jan. 6, 2015

(54) METHOD OF TREATING ANKYLOSING SPONDYLITIS

(71) Applicants: Robert L. Wong, Basking Ridge, NJ (US); Hartmut Kupper, Mutterstadt (DE); John R. Medich, Highland Park, IL (US)

(72) Inventors: Robert L. Wong, Basking Ridge, NJ (US); Hartmut Kupper, Mutterstadt (DE); John R. Medich, Highland Park, IL (US)

(73) Assignee: AbbVie Biotechnology Ltd, Hamilton (BM)

( * ) Notice: Subject to any disclaimer, the term of this patent is extended or adjusted under 35 U.S.C. 154(b) by 0 days.

(21) Appl. No.: 14/306,658

(22) Filed: Jun. 17, 2014

(65) Prior Publication Data

US 2014/0328855 A1 Nov. 6, 2014

Related U.S. Application Data

(63) Continuation of application No. 11/811,355, filed on Jun. 8, 2007.

(60) Provisional application No. 60/812,312, filed on Jun. 8, 2006, provisional application No. 60/857,352, filed on Nov. 6, 2006, provisional application No. 60/858,328, filed on Nov. 10, 2006.

(51) Int. Cl.
*A61K 39/395* (2006.01)
*C07K 16/24* (2006.01)

(52) U.S. Cl.
CPC .................................... *C07K 16/241* (2013.01)
USPC ..................................... 424/142.1; 424/145.1

(58) Field of Classification Search
None
See application file for complete search history.

(56) References Cited

U.S. PATENT DOCUMENTS

| | | | |
|---|---|---|---|
| 5,656,272 A | 8/1997 | Le et al. | |
| 5,872,215 A | 2/1999 | Osbourne et al. | |
| 5,874,060 A | 2/1999 | Armour et al. | |
| 6,090,382 A | 7/2000 | Salfeld et al. | |
| 6,258,562 B1 | 7/2001 | Salfeld et al. | |
| 6,448,380 B2 | 9/2002 | Rathjen et al. | |
| 6,451,983 B2 | 9/2002 | Rathjen et al. | |
| 6,498,237 B2 | 12/2002 | Rathjen et al. | |
| 6,509,015 B1 | 1/2003 | Salfeld et al. | |
| 7,070,775 B2 | 7/2006 | Le et al. | |
| 7,078,064 B2 | 7/2006 | Zabrecky et al. | |
| 7,192,584 B2 | 3/2007 | Le et al. | |
| 7,223,394 B2 | 5/2007 | Salfeld et al. | |
| 7,250,165 B2 | 7/2007 | Heavner et al. | |
| 7,276,239 B2 | 10/2007 | Le et al. | |
| 7,521,206 B2 | 4/2009 | Heavner et al. | |
| 7,541,031 B2 | 6/2009 | Salfeld et al. | |
| 7,588,761 B2 | 9/2009 | Salfeld et al. | |
| 7,691,378 B2 | 4/2010 | Heavner et al. | |
| 7,863,426 B2 | 1/2011 | Wan et al. | |
| 7,919,264 B2 | 4/2011 | Maksymowych et al. | |
| 8,034,906 B2 | 10/2011 | Borhani et al. | |
| 8,092,998 B2 | 1/2012 | Stuhlmuller et al. | |
| 8,093,045 B2 | 1/2012 | Pla et al. | |
| 8,187,836 B2 | 5/2012 | Hsieh et al. | |
| 8,197,813 B2 | 6/2012 | Salfeld et al. | |
| 8,206,714 B2 | 6/2012 | Salfeld et al. | |
| 8,216,583 B2 | 7/2012 | Krause et al. | |
| 8,231,876 B2 | 7/2012 | Wan et al. | |
| 8,372,400 B2 | 2/2013 | Salfeld et al. | |
| 8,372,401 B2 | 2/2013 | Salfeld et al. | |
| 8,414,894 B2 | 4/2013 | Salfeld et al. | |
| 8,420,081 B2 | 4/2013 | Fraunhofer et al. | |
| 8,436,149 B2 | 5/2013 | Borhani et al. | |
| 8,455,219 B2 | 6/2013 | Hsieh et al. | |
| 8,636,704 B2 | 1/2014 | Shang et al. | |
| 8,663,945 B2 | 3/2014 | Pla et al. | |
| 8,679,061 B2 | 3/2014 | Julian et al. | |
| 8,715,664 B2 | 5/2014 | Hoffman et al. | |
| 8,747,854 B2 | 6/2014 | Okun et al. | |
| 8,753,633 B2 | 6/2014 | Salfeld et al. | |
| 8,753,839 B2 | 6/2014 | Fraunhofer et al. | |
| 2003/0012786 A1 | 1/2003 | Teoh et al. | |
| 2003/0161828 A1 | 8/2003 | Abdelghany et al. | |
| 2003/0206898 A1 | 11/2003 | Fischkoff et al. | |
| 2003/0219438 A1 | 11/2003 | Salfeld et al. | |
| 2003/0235585 A1 | 12/2003 | Fischkoff et al. | |
| 2004/0009172 A1 | 1/2004 | Fischkoff et al. | |
| 2004/0033228 A1 | 2/2004 | Krause et al. | |
| 2004/0105858 A1 | 6/2004 | Kim et al. | |
| 2004/0120952 A1 | 6/2004 | Knight et al. | |
| 2004/0126372 A1 | 7/2004 | Banerjee et al. | |

(Continued)

FOREIGN PATENT DOCUMENTS

| | | |
|---|---|---|
| WO | WO97/29131 | 8/1997 |
| WO | WO02/12502 | 2/2002 |

OTHER PUBLICATIONS van der Heijde et al. Adalimumab effectively reduces the signs and symptoms of active ankylosing spondylitis in patients with total spinal ankylosis. Ann Rheum Dis. Sep. 2008;67(9):1218-21. Epub Dec. 4, 2007.*
Anderson J. et al., "Ankylosing spondylitis Assessment Group Preliminary Definition of Short-Term Improvement in Ankylosing Spondylitis", Arthritis & Rhemuatism (2001) 44(8): 1876-1886.
Asli, B. et al., "Inhibition of Tumor Necrosis Factor α and Ankylosing Spondylitis", N Engl J Med (2003) 348:4: 359-360.

(Continued)

*Primary Examiner* — David Romeo
(74) *Attorney, Agent, or Firm* — Foley Hoag LLP

(57) ABSTRACT

The invention provides methods, uses and compositions for the treatment of ankylosing spondylitis (AS). The invention describes methods and uses for treating ankylosing spondylitis, wherein a TNFα inhibitor, such as a human TNFα antibody, or antigen-binding portion thereof, is used to reduce signs and symptoms of ankylosing spondylitis in a subject. Also described are methods for determining the efficacy of a TNFα inhibitor for treatment of ankylosing spondylitis in a subject.

6 Claims, 11 Drawing Sheets

(56) References Cited

U.S. PATENT DOCUMENTS

| | | |
|---|---|---|
| 2004/0126373 A1 | 7/2004 | Banerjee et al. |
| 2004/0131614 A1 | 7/2004 | Banerjee et al. |
| 2004/0136989 A1 | 7/2004 | Banerjee et al. |
| 2004/0136990 A1 | 7/2004 | Banerjee et al. |
| 2004/0136991 A1 | 7/2004 | Banerjee et al. |
| 2004/0151722 A1 | 8/2004 | Banerjee et al. |
| 2004/0166111 A1 | 8/2004 | Kaymakcalan et al. |
| 2004/0219142 A1 | 11/2004 | Banerjee et al. |
| 2005/0249735 A1 | 11/2005 | Le et al. |
| 2006/0009385 A1 | 1/2006 | Hoffman et al. |
| 2006/0018907 A1 | 1/2006 | Le et al. |
| 2006/0083741 A1 | 4/2006 | Hoffman et al. |
| 2006/0246073 A1 | 11/2006 | Knight et al. |
| 2007/0041905 A1 | 2/2007 | Hoffman et al. |
| 2007/0071747 A1 | 3/2007 | Hoffman et al. |
| 2007/0081996 A1 | 4/2007 | Hoffman et al. |
| 2007/0172897 A1 | 7/2007 | Maksymowych et al. |
| 2007/0196373 A1 | 8/2007 | Le et al. |
| 2007/0202104 A1 | 8/2007 | Banerjee et al. |
| 2007/0298040 A1 | 12/2007 | Le et al. |
| 2008/0025976 A1 | 1/2008 | Le et al. |
| 2008/0118496 A1 | 5/2008 | Medich et al. |
| 2008/0131374 A1 | 6/2008 | Medich et al. |
| 2008/0166348 A1 | 7/2008 | Kupper et al. |
| 2008/0193466 A1 | 8/2008 | Banerjee et al. |
| 2008/0311043 A1 | 12/2008 | Hoffman et al. |
| 2009/0028794 A1 | 1/2009 | Medich et al. |
| 2009/0068172 A1 | 3/2009 | Kaymakcalan et al. |
| 2009/0110679 A1 | 4/2009 | Li et al. |
| 2009/0123378 A1 | 5/2009 | Wong et al. |
| 2009/0148513 A1 | 6/2009 | Fraunhofer et al. |
| 2009/0226530 A1 | 9/2009 | Lassner et al. |
| 2009/0258018 A1 | 10/2009 | Medich et al. |
| 2009/0271164 A1 | 10/2009 | Peng et al. |
| 2009/0280065 A1 | 11/2009 | Willian et al. |
| 2009/0304682 A1 | 12/2009 | Hoffman et al. |
| 2009/0317399 A1 | 12/2009 | Pollack et al. |
| 2010/0003243 A1 | 1/2010 | Okun et al. |
| 2010/0021451 A1 | 1/2010 | Wong et al. |
| 2010/0040630 A1 | 2/2010 | Elden et al. |
| 2010/0160894 A1 | 6/2010 | Julian et al. |
| 2010/0278822 A1 | 11/2010 | Fraunhofer et al. |
| 2011/0054414 A1 | 3/2011 | Shang et al. |
| 2011/0171227 A1 | 7/2011 | Okun et al. |
| 2011/0300151 A1 | 12/2011 | Okun et al. |
| 2012/0014956 A1 | 1/2012 | Kupper et al. |
| 2012/0039900 A1 | 2/2012 | Stuhlmüller et al. |
| 2012/0077213 A1 | 3/2012 | Pla et al. |
| 2012/0107783 A1 | 5/2012 | Julian et al. |
| 2012/0129185 A1 | 5/2012 | Maksymowych et al. |
| 2012/0171123 A1 | 7/2012 | Medich et al. |
| 2012/0177596 A1 | 7/2012 | Fischkoff et al. |
| 2012/0258114 A1 | 10/2012 | Salfeld et al. |
| 2012/0282262 A1 | 11/2012 | Okun et al. |
| 2012/0282270 A1 | 11/2012 | Krause et al. |
| 2013/0004507 A1 | 1/2013 | Fischkoff et al. |
| 2013/0028903 A1 | 1/2013 | Wan et al. |
| 2013/0115224 A1 | 5/2013 | Salfeld et al. |
| 2013/0122011 A1 | 5/2013 | Hoffman et al. |
| 2013/0122018 A1 | 5/2013 | Salfeld et al. |
| 2013/0156760 A1 | 6/2013 | Fraunhofer et al. |
| 2013/0195888 A1 | 8/2013 | Wang et al. |
| 2013/0243786 A1 | 9/2013 | Banerjee et al. |
| 2013/0273059 A1 | 10/2013 | Wan et al. |
| 2013/0280267 A1 | 10/2013 | Wan et al. |
| 2013/0309242 A1 | 11/2013 | Wan et al. |
| 2013/0309309 A1 | 11/2013 | Borhani et al. |
| 2013/0323261 A1 | 12/2013 | Wan et al. |
| 2013/0330356 A1 | 12/2013 | Salfeld et al. |
| 2013/0330357 A1 | 12/2013 | Salfeld et al. |
| 2013/0344537 A1 | 12/2013 | Hsieh et al. |
| 2014/0086929 A1 | 3/2014 | Krause et al. |
| 2014/0086930 A1 | 3/2014 | Krause et al. |
| 2014/0086931 A1 | 3/2014 | Krause et al. |
| 2014/0127222 A1 | 5/2014 | Krause et al. |
| 2014/0134674 A1 | 5/2014 | Pla et al. |
| 2014/0134675 A1 | 5/2014 | Pla et al. |

OTHER PUBLICATIONS

Boeger, C. et al., Treatment of ankylosing spondylitis with infliximab, Ann Rheum Dis (2001) 60: 1159-1160.

Boulos, P. et al., "Pharmacological treatment of ankylosing spondylitis" Drugs (2005) 65(15): 2111-2127.

Brandt, J. et al., "Successful Short Term Treatment of Severe Undifferentiated Spondyloarthropathy with the Anti-Tumor Necrosis Factor-α Monoclonal Antibody Infliximab", J Rheumatol (2002) 29: 118-22.

Brandt, J. et al., "Successful Treatment of Active Ankylosing Spondylities with the Anti-Tumor Necrosis Factor α Monoclonal Antibody Infliximab", Arthritis & Rheumat, (2000) 43(6): 1346-1352.

Braun, J., et al., "New treatment options in spondyloarthropathies: increasing evidence for significant efficacy of anti-tumor necrosis factor therapy" Curr Opin Rheumatol.(2001) 13:245-249.

Braun, J., et al., "Anti-TNFα: a new dimension in the pharmacotherapy of the spondyloarthropathies", Ann Rheum Dis (2002) 59(6): 404-7.

Braun, J., et al., "Anti-tumor necrosis factor α therapy for ankylosing spondylitis: international experience",Ann Rheum Dis (2002) 61(Suppl 3):ii51-ii60.

Braun, J., et al., "Therapy of ankylosing spondylitis and other spondyloarthritides: established medical treatment, anti-TNF-α therapy and other novel approaches", Arthritis Res (2002) 4:307-321.

Braun, J., et al., "Treatment of active ankylosing spondylitis with infliximab: a randomised controlled multicentre trial", Lancet (2002) 359: 1187-93.

Braun, J., et al., "International ASAS consensus statement for the use of anti-tumour necrosis factor agents in patients with ankylosing spondylitis", Ann Rheum Dis (2003) 62: 817-824.

Braun, J., et al., "Biologic therapies in the spondyloarthritis: new opportunities, new challenges", Curr Opin Rheumatol (2003) 5:394-407.

Braun, J., et al., "Novel approaches in the treatment of ankylosing spondylitis and other spondyloarthritides", Expert Opin. Investig. Drugs (2003) 12(7): 1097-1109.

Breban, M., et al., "Efficacy of infliximab in refractory ankylosing spondylitis: results of a six-month open-label study", Rheumatology (2002) 41:1280-1285.

Ching L-M. et al., "Induction of intratumoral tumor necrosis factor (TNF) synthesis and hemorrhagic necrosis by 5,6-dimethylxanthenone-4-acetic acid (DMXAA) in TNF knockout mice" Cancer Res. (1999) 59: 3304-3307.

Davis, J. et al., "Major clinical response and partial remission in ankylosing spondylitis subjects treated with adalimumab: The ATLAS Trial" Arthritis & Rheumatism (2005) 52: S208-209.

Davis, J. et al., "Understanding the role of tumor necrosis factor inhibition in ankylosing spondylitis" Seminars Arthritis Rheumatism (2005) 34(4): 668-677.

Davis, J. et al., "Adalimumab Reduces Pain and Fatigue in Ankylosing Spondylitis (AS) Patients—Results from the ATLAS Trial", Annual Scientific Meeting, 2006, Amsterdam, The Netherlands, Jun. 21-24, 2006.

Dayer, J.M. et al., "Anti-TNF-α therapy fo ankylosing spondylitis—a specific or nonspecific treatment", N Engl J Med, vol. 346, No. 18 (2002):1399-1400.

Dernis, E. et al., "Infliximab in spondylarthropathy-Influence on bone density", Clin Exp Rheumatol (2002) 20 (Suppl. 28): S185-S186.

Efthimiou, P. et al., "Role of biological agents in immune-mediated inflammatory diseases" Southern Med J (2005) 98(2): 192-204.

Gorman, J.D. et al., "Treatment of ankylosing spondylitis by inhibition of tumor necrosis factor α", N Engl J Med (2002) 346:1349-56.

Haibel H. et al., "Adalimumab reduced spinal symptoms in active ankylosing spondylitis: clinical and manetic responance imaging results of a fifty-two week open-label trial" Arthritis & Rheumatism (2006) 54:678-681.

(56) References Cited

OTHER PUBLICATIONS

Haibel H. et al., "Adalimumab in the treatment of active ankylosing spondylitis: Results of an open-label, 52-week trial" Ann Rheum Dis (2005) 64(Suppl III):316.

Horneff, G. et al., "TNF-α antagonists for the treatment of juvenile-onset spondyloarthritides", Clin Exp Rheumatol (2002) 20 (Suppl. 28):S137-S142.

Kaiser, M.J. et al., "Efficacy of infliximab (Remicade®) in the treatment of spondyloarthropathies. Two case reports", Joint Bone Spine (2001) 68:525-7.

Kempeni, J., "Preliminary results of early clinical trials with the fully human anti-TNFα monoclonal antibody D2E7", Ann Rheum Dis 1999;58:(Suppl I) I70-I72.

Luo, M.P. et al., "Adalimumab reduces fatigue in patients with active ankylosing spondylitis (AS)—6 month results of a Canadian AS study", Value in Health, 2005, 8(6): A13.

Luc, M. et al., "Patients without biological inflammation and responders to anti-TNF-alpha in axial ankylosing spoindylitis" Arthritis & Rheumatism (2005) 52: S216.

Maksymowych, W.P. et al., "Canadian Rheumatology Association Clonsensus on the Use of Anti-Tumor Necrosis Factor-α Directed Therapies in the Treatment of Spondyloarthritis", J Rheumatol (2003) 30:1356-1363.

Maksymowych, W.P. et al., "Efficacy of adalimumab in active ankylosing spondylitis (AS)—Results of the Canadian AS Study" Arthritis & Rheumatism (2005) 52: S217.

Marzo-Ortega, H. et al., "Inhibition of Tumor Necrosis Factor α and Ankylosing Spondylitis", N Engl J Med (2003) 348(4): 359-360.

Pham T. et al., "Initiation of biological agents in patients with ankylosing spondylitis: results of a Delphi study by the ASAS Group", Ann Rheum Dis (2003) 62:812-816.

Reimold, A.M. et al., "New Indications for Treatment of Chronic Inflammation by TNFα Blockade", Am J Med Sci (2003) 325(2): 75-92.

Rudwaleit M. et al., "How to diagnose axial spondyloarthritis early" Ann. Rheum Dis. (2004) 63: 535-543.

Schnarr, S. et al., "Anti-tumour necrosis factor (TNF)-α therapy in undifferentiated spondyloarthropathy", Clin Exp Rheumatol (2002) 20 (Suppl. 28): S126-S129.

Sieper J. et al., "New Treatment options in ankylosing spondylitis: a role for anti-TNFα therapy", Ann Rheum Dis (2001) 60: iii58-iii61.

Stokes, D.G. et al., "Potential of Tumor Necrosis Factor Neutralization Strategies in Rheumatologic Disorders Other Than Rheumatoid Arthritis", Seminars in Arthritis and Rheumatism, (2003) 33(1): 1-18.

Stone, M. et al., "Chinical and Imaging Correlates of Response to Treatment with Infliximab in Patients with Ankylosing Spondylitis", J Rheumatol (2001) 28: 1605-1614.

Van den Bosch, F. et al., "Crohn's disease associated with spoldyloarthropathy: effect of TNF-α blockade with infliximab on articular symptoms", The Lancet, (2000) 356: 1821-1822.

Van der Heijde D. et al., "Adalimumab therapy results in significant reduction of signs and symptoms in subjects with ankylosing spondylitis: The ATLAS Trial" Arthritis & Rheumatism (2005) 52(9): S281.

Van de Heijde D. et al., "Adalimumab improves health-related quality of life in patients with active ankylosing spondylitis—The ATLAS trial." (2005) 52(9): S211.

Wendling D. et al. "Anti-TNFα therapy in ankylosing spondylitis" Expert Opion Pharmacother. (2004) 5(7): 1497-1507.

Zou, J.X. et al., "Immunological basis for the use of TNFα-blocking agents in ankylosing spondylitis and immunological changes during treatment", Clin Exp Rheumatol (2002) 20 (Suppl. 28): S34-S37.

Wikipedia, Anklyosing Spondylitis [online], [retrieved on Jul. 3, 2013]. Retrieved from the Internet URL:http://en.wikipedia.org/wiki/Ankylosing_spondylitis.

Roussou et al. "The Bath Ankylosing Spondylitis Activity and Function Indices (BASDI and BASFI) and their correlation with main symptoms experienced by patients with spondyloarthritis." Clin Rheumatol (2010) 29:869-874.

Kavanaugh A.F. "Adalimumab treatment with and without methotrexate in patients with moderate to severe psoriatic arthritis: Results from ADEPT." Abstract #FR10227, Ann Rheum Dis (2005) 64 (Suppl III):325.

Braun et al. "Persistent clinical response to the anti-TNF-alpha antibody infliximab in patients with ankylosing spondylitis over 3 years." Rheumatology (Oxford) (2005) 44(5):670-676. Epub May 9, 2005.

Dernis-Labous et al. "Assessment of fatigue in the management of patients with ankylosing spondylitis." Rheumatology (Oxford) (2003) 42(12):1523-1528. Epub Sep. 16, 2003.

Heiberg et al. "The comparative effectiveness of tumor necrosis factor-blocking agents in patients with rheumatoid arthritis and patients with ankylosing spondylitis: a six-month, longitudinal, observational, multicenter study." Arthritis Rheum (2005) 52(8):2506-2512.

van der Heijde et al. "Adalimumab is effective in reducing signs and symptoms in ankylosing spondylitis patients with total spinal ankylosis—Results from ATLAS." Ann Rheum Dis. (2007) 66(Suppl II):412 (Abstract FRI0441).

* cited by examiner

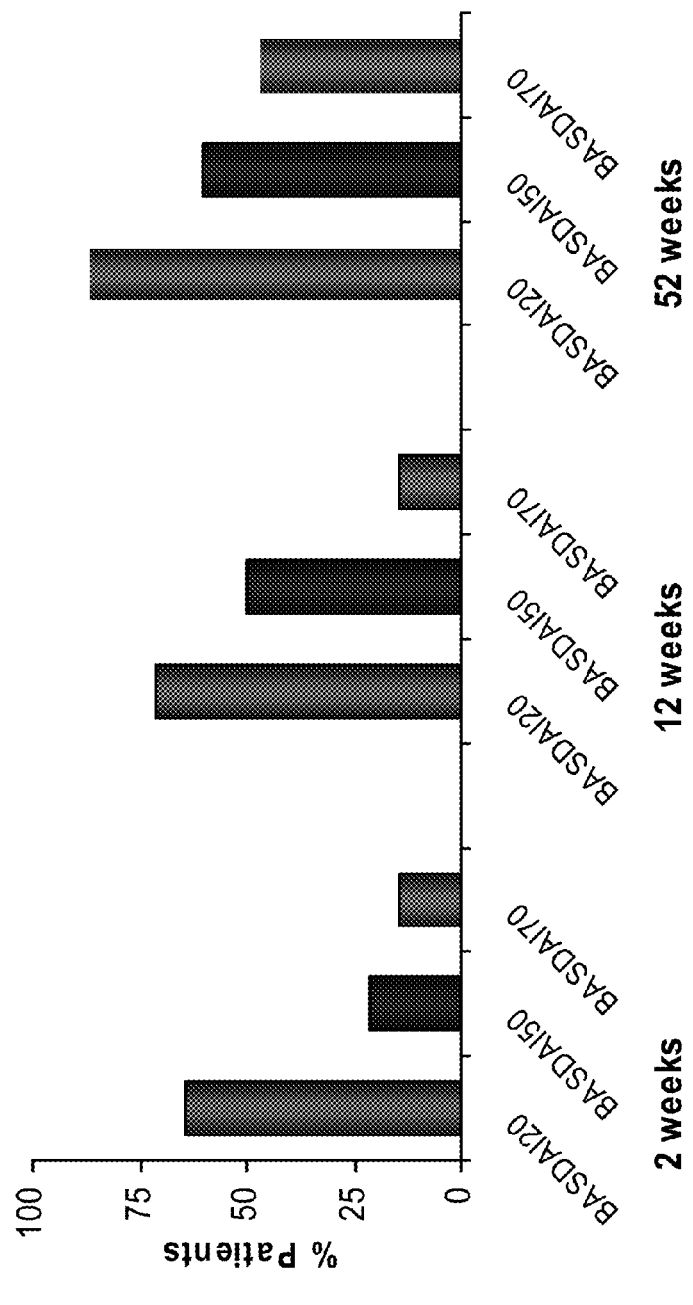
Figure 1: Improvement of BASDAI20, 50 and 70 after 2, 12 and 52 weeks of treatment with adalimumab

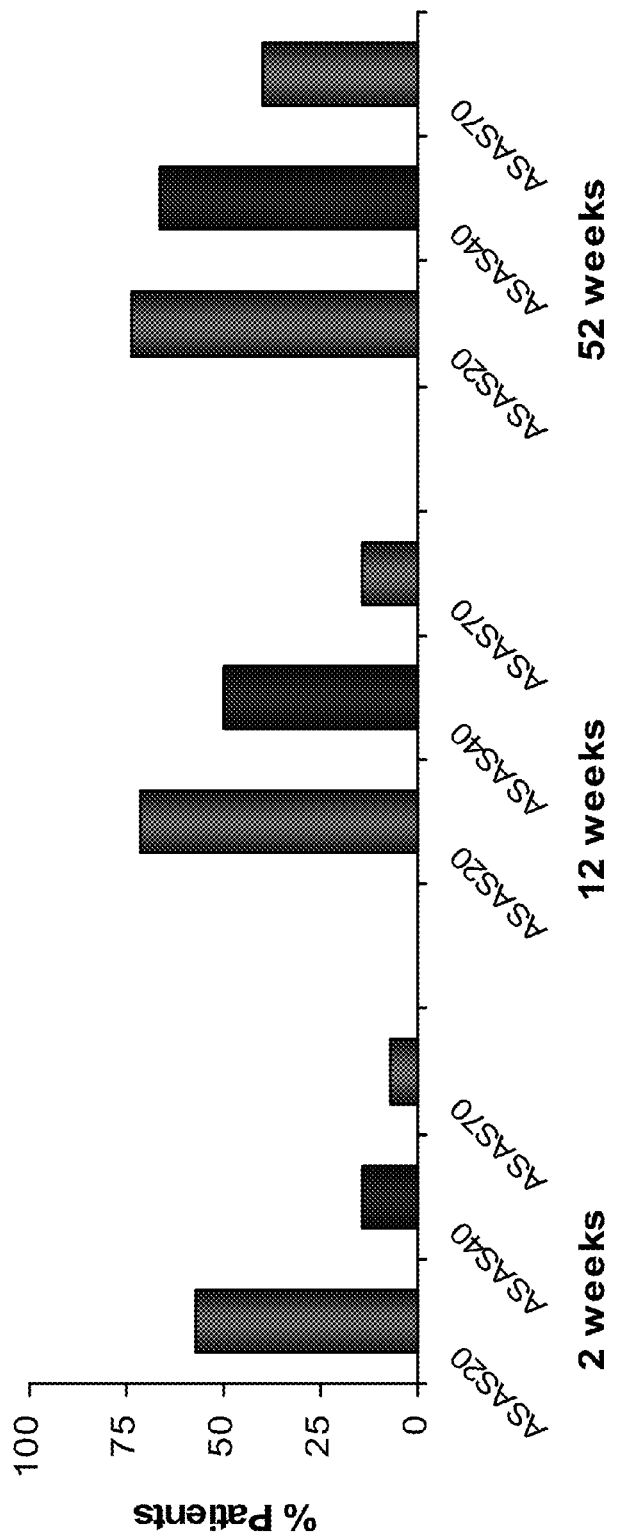
Figure 2: Improvement of ASAS20, 40 and 70 criteria after 2, 12 and 52 weeks of treatment with adalimumab

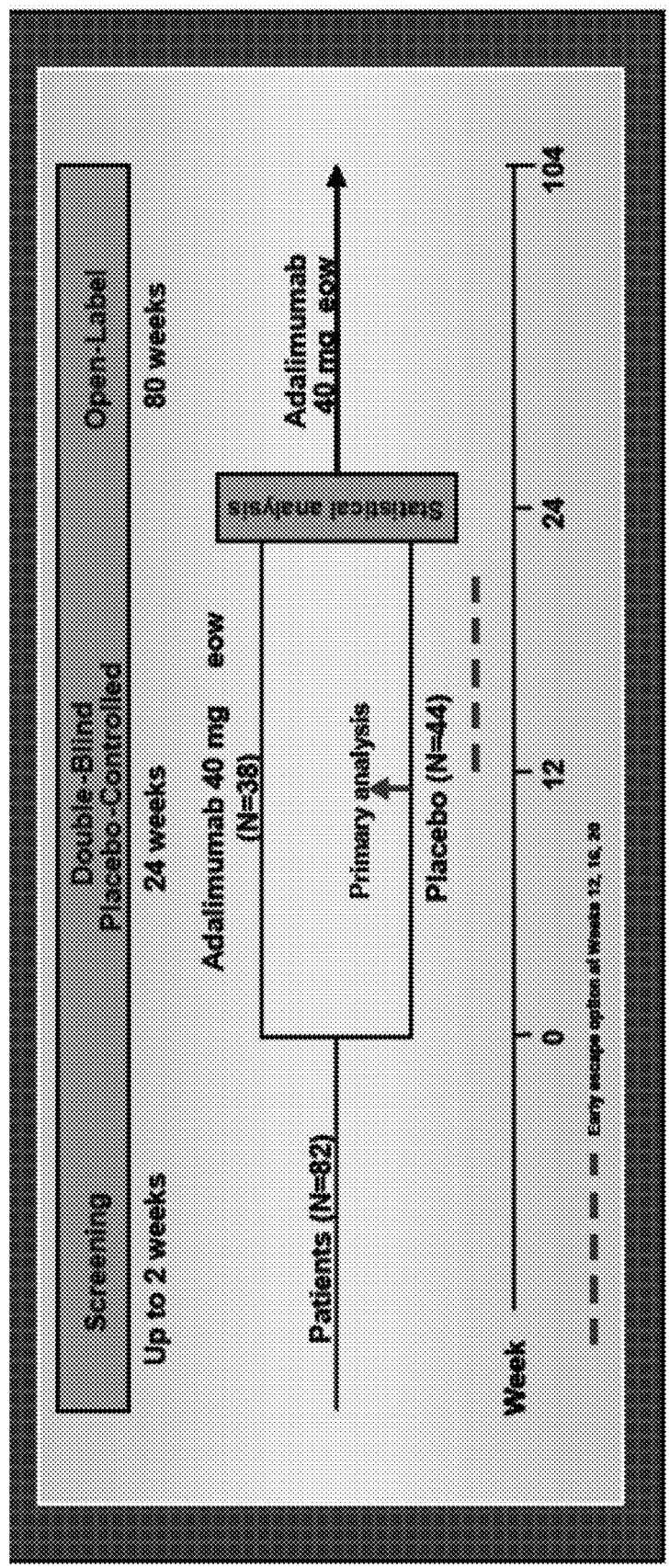
Figure 3: Canadian AS Study Design

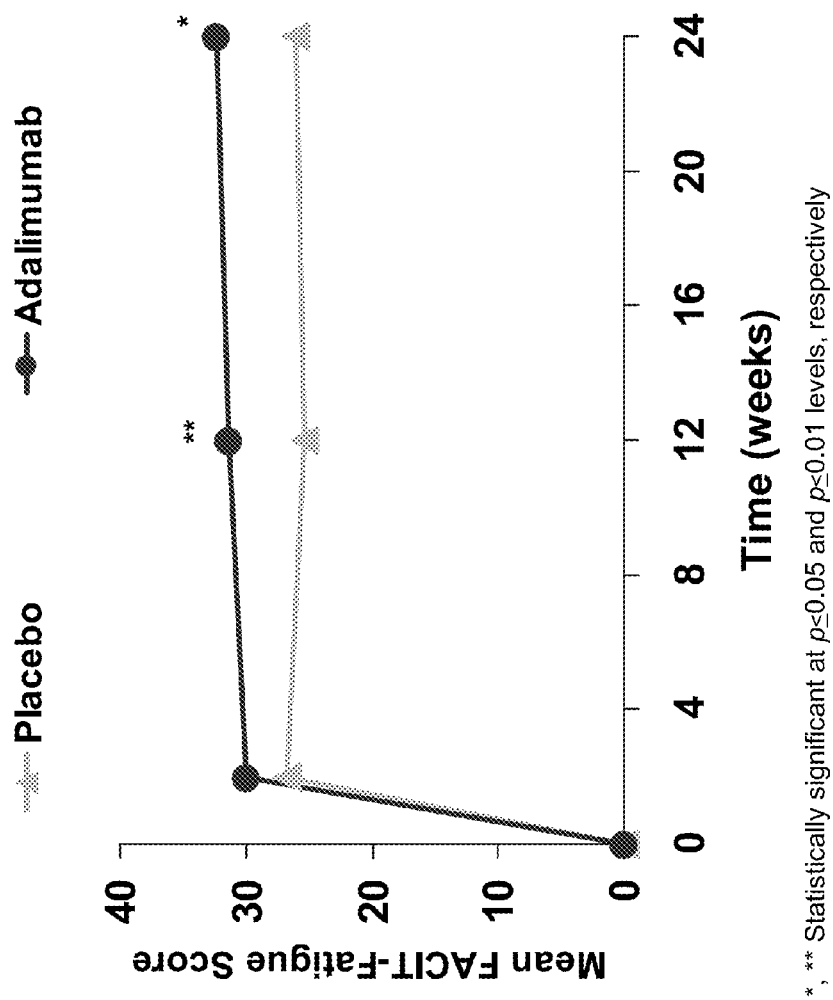
Figure 4: Mean FACIT-Fatigue Score by Treatment Group Over Time

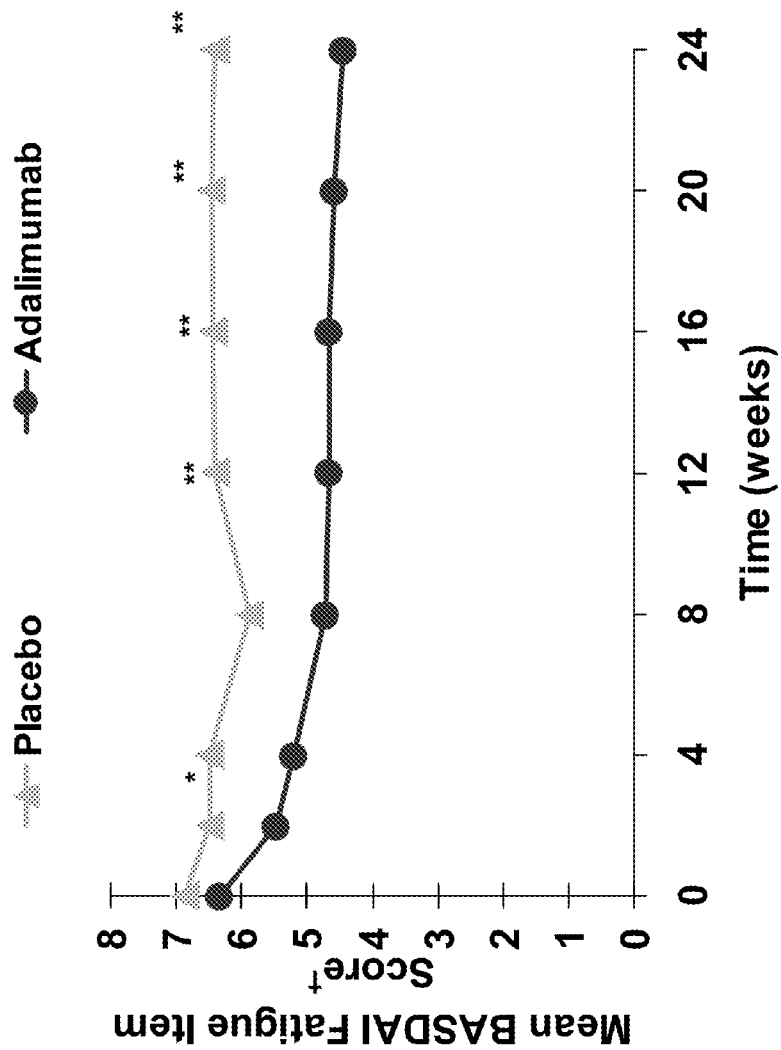
Figure 5: Mean BASDAI-Fatigue Item Score by Treatment Group Over Time

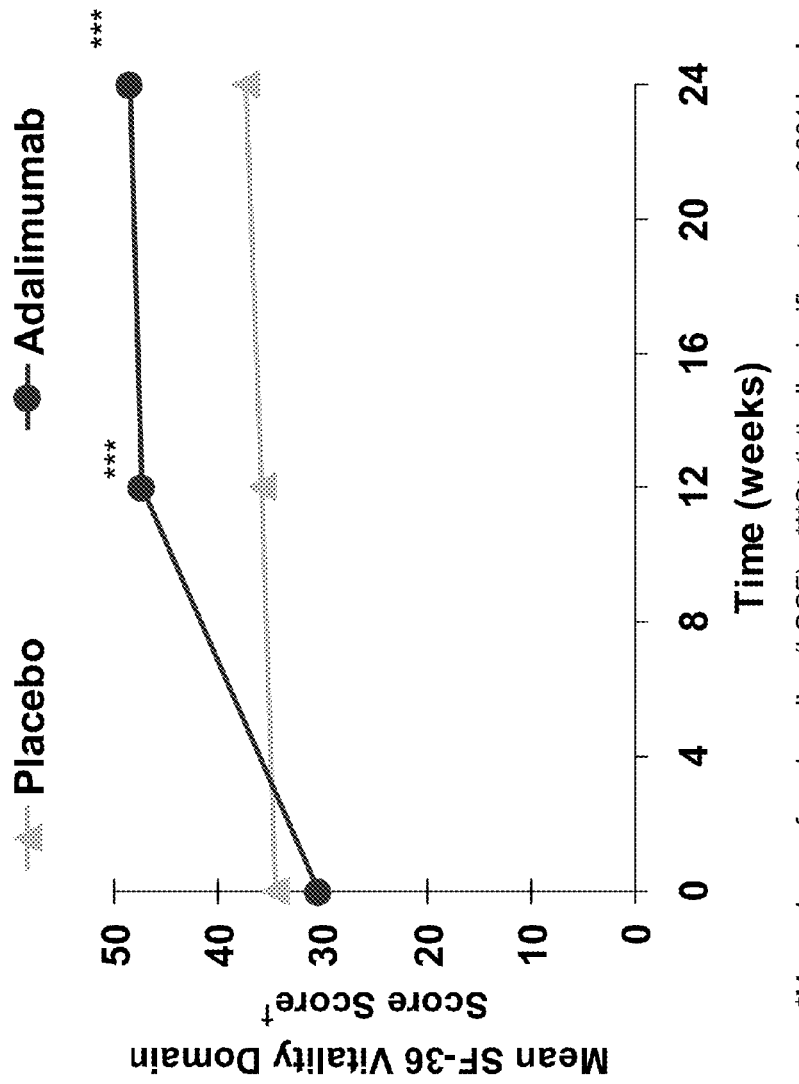
Figure 6: Mean SF-36 Vitality Domain Score by Treatment Group Over Time

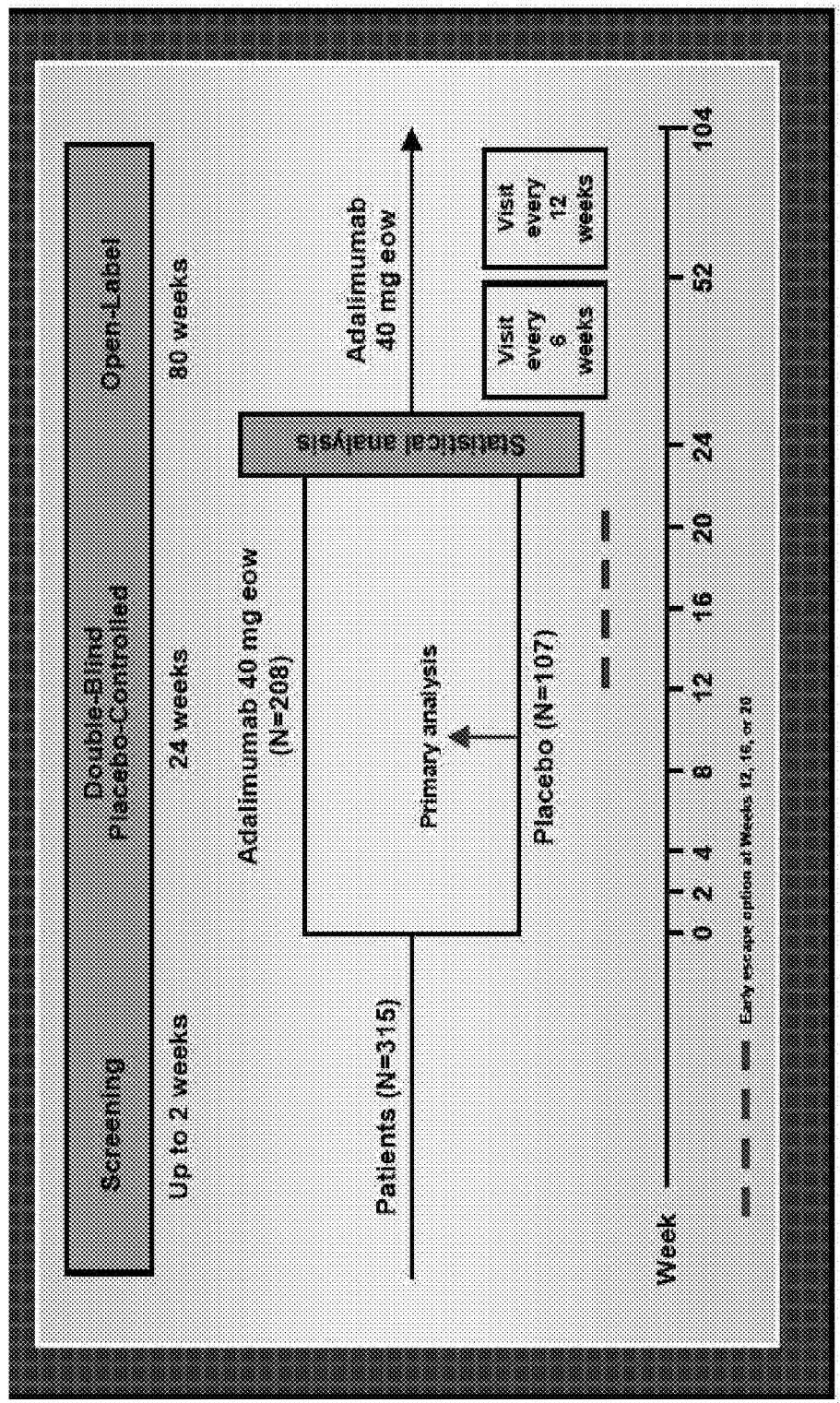
Figure 7: Study H Design

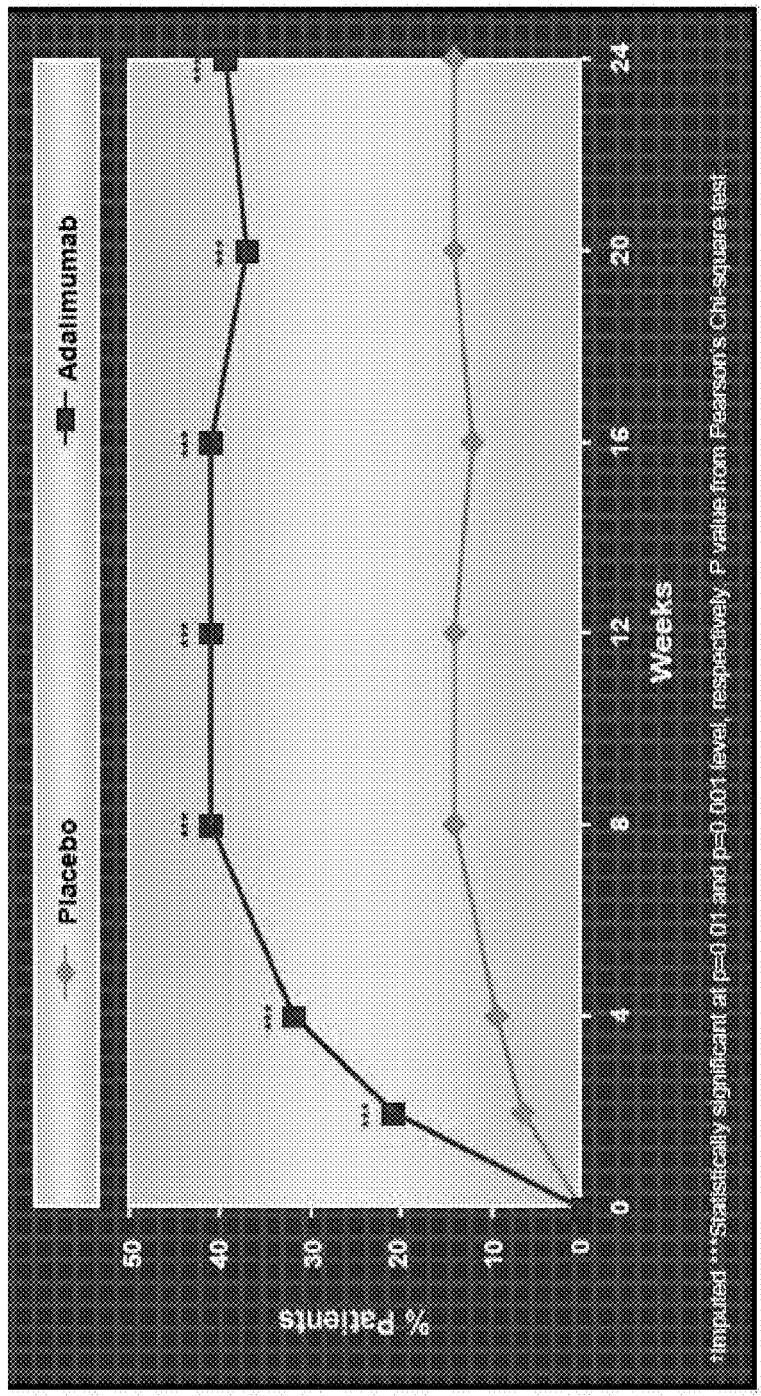
Figure 8: ASAS40† Response Over Time

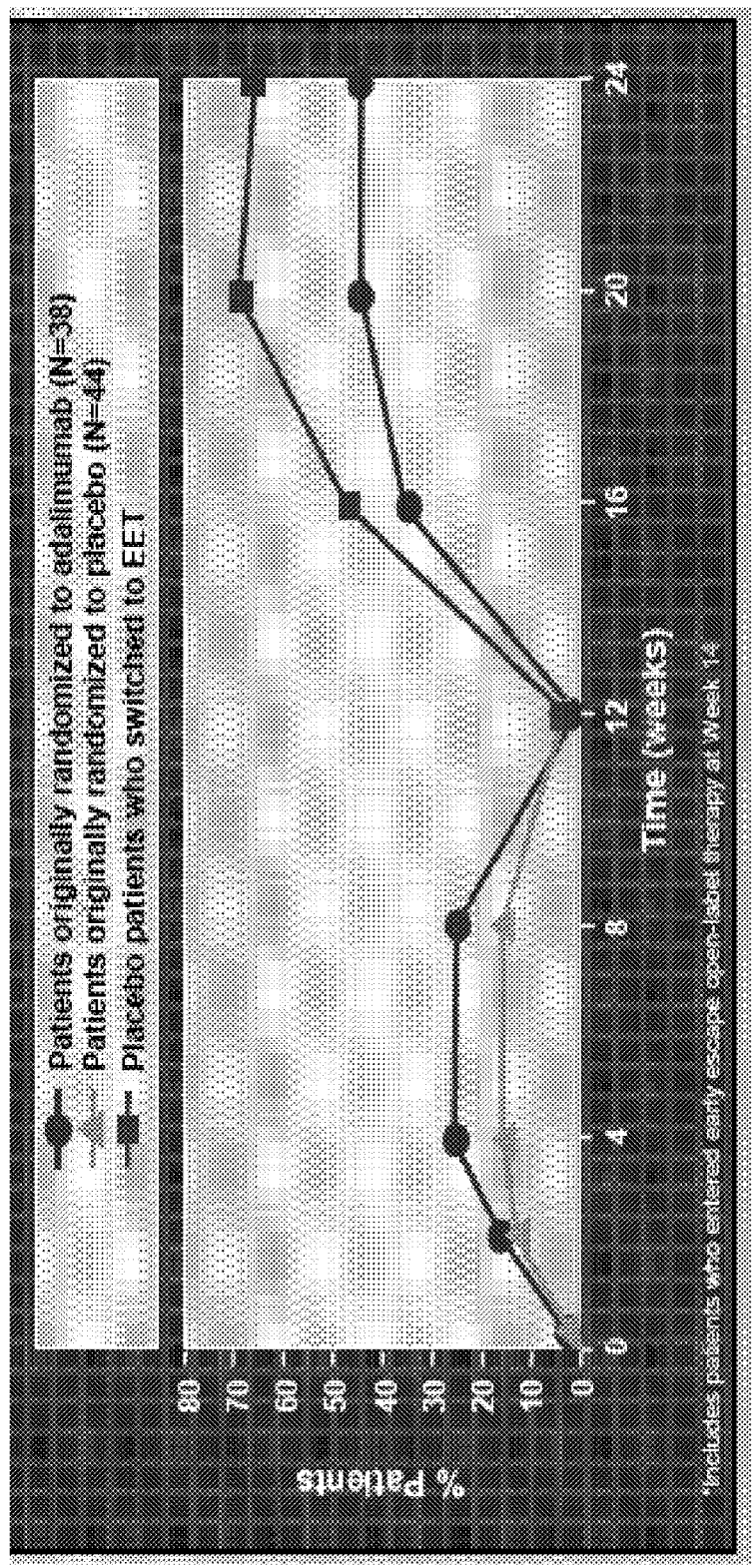
Figure 9: ASAS 20 Response for Those Patients Who Switched to EET at Week 12*

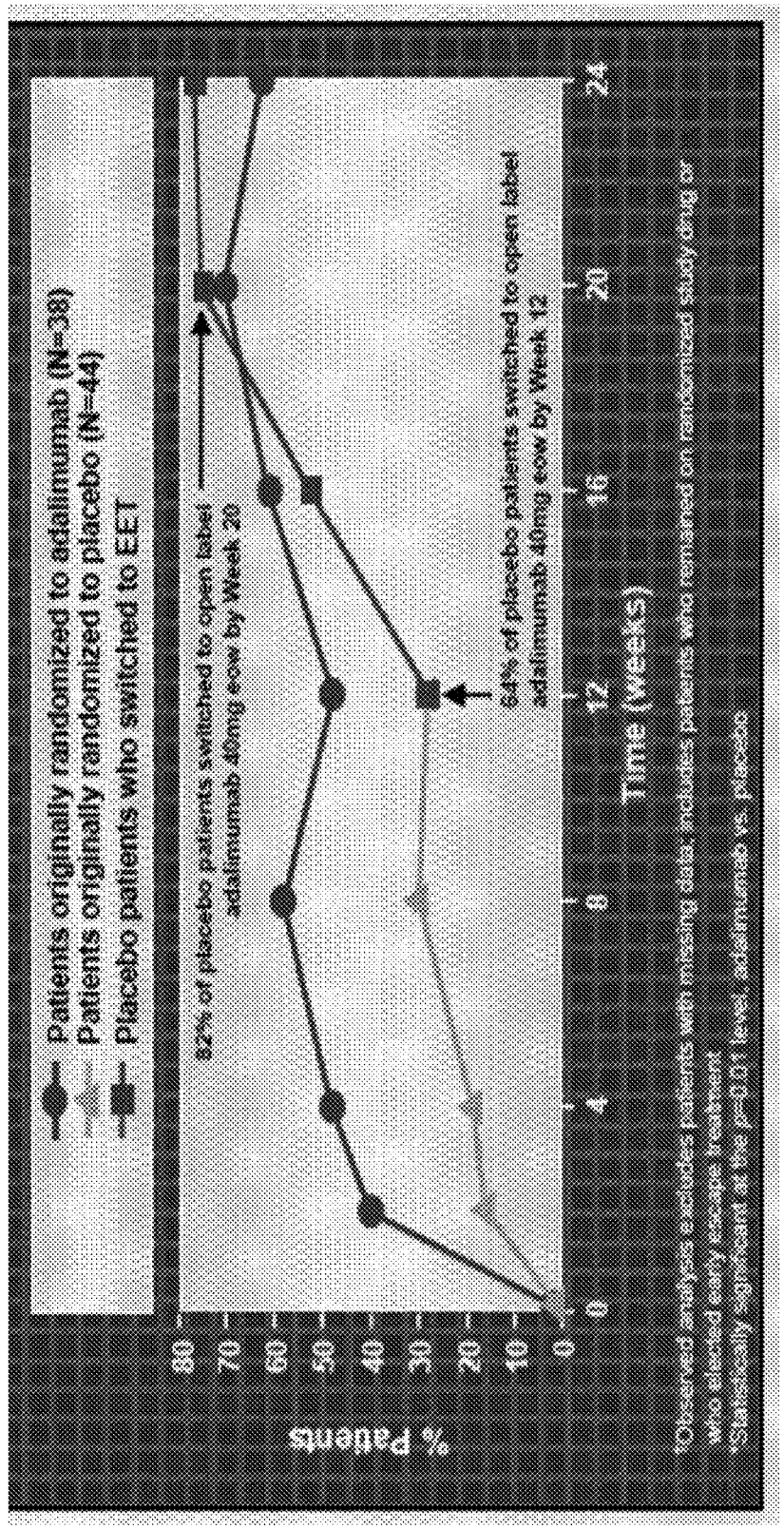
Figure 10: ASAS 20 Response Time Course--Observed†

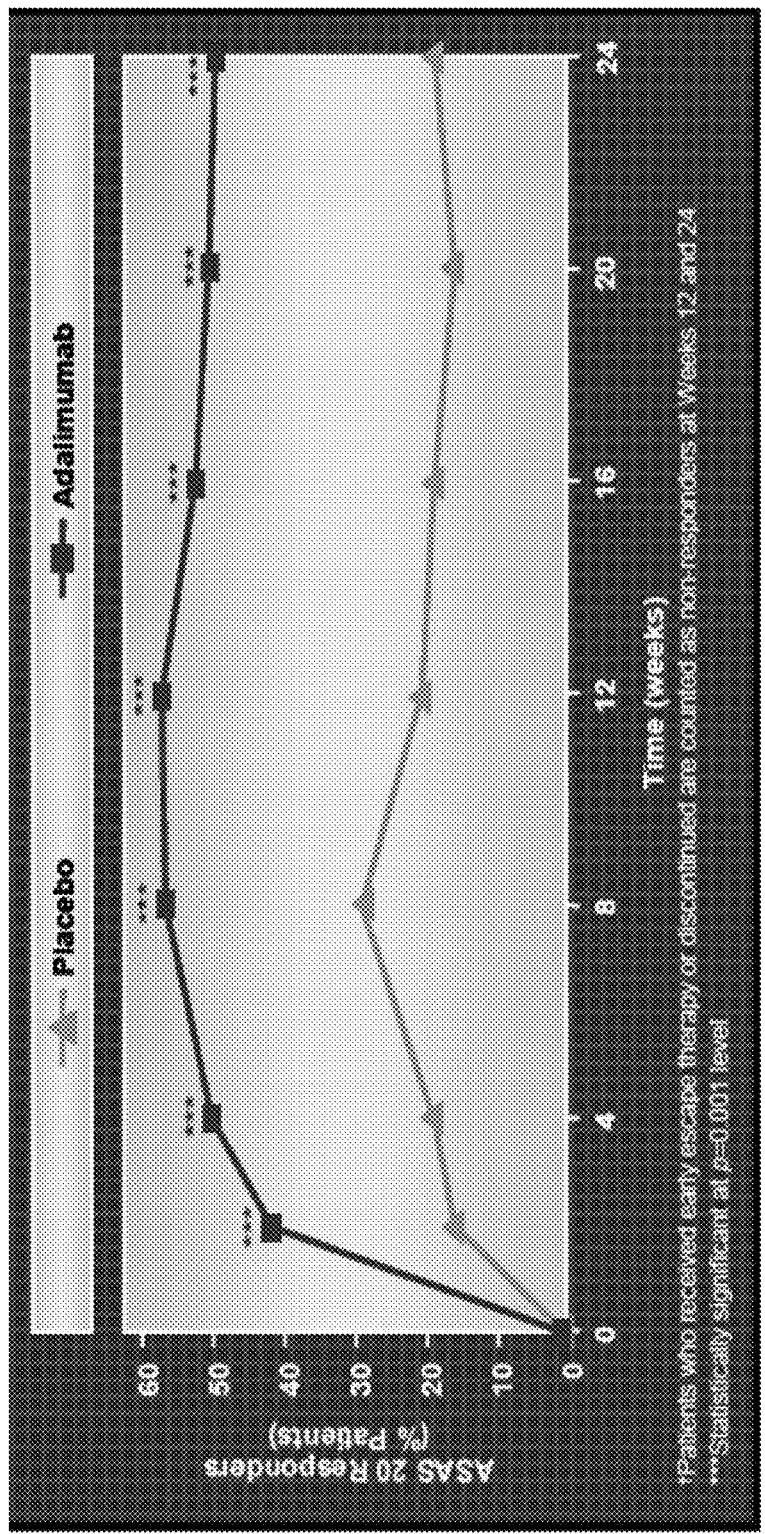
Figure 11: Time Course of ASAS 20--Imputed†

```
                        SEQUENCE LISTING

<160> NUMBER OF SEQ ID NOS: 37

<210> SEQ ID NO 1
<211> LENGTH: 107
<212> TYPE: PRT
<213> ORGANISM: Artificial
<220> FEATURE:
<223> OTHER INFORMATION: D2E7 light chain variable region

<400> SEQUENCE: 1

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Tyr
             20                  25                  30

Leu Ala Trp Tyr Gln Gln Lys Pro Gly Lys Ala Pro Lys Leu Leu Ile
         35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Arg Tyr Asn Arg Ala Pro Tyr
                 85                  90                  95

Thr Phe Gly Gln Gly Thr Lys Val Glu Ile Lys
            100                 105

<210> SEQ ID NO 2
<211> LENGTH: 121
<212> TYPE: PRT
<213> ORGANISM: Artificial
<220> FEATURE:
<223> OTHER INFORMATION: D2E7 heavy chain variable region

<400> SEQUENCE: 2

Glu Val Gln Leu Val Glu Ser Gly Gly Leu Val Gln Pro Gly Arg
  1               5                  10                  15

Ser Leu Arg Leu Ser Cys Ala Ala Ser Gly Phe Thr Phe Asp Asp Tyr
             20                  25                  30

Ala Met His Trp Val Arg Gln Ala Pro Gly Lys Gly Leu Glu Trp Val
         35                  40                  45

Ser Ala Ile Thr Trp Asn Ser Gly His Ile Asp Tyr Ala Asp Ser Val
 50                  55                  60

Glu Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
            115                 120

<210> SEQ ID NO 3
<211> LENGTH: 9
```

```
<212> TYPE: PRT
<213> ORGANISM: Artificial
<220> FEATURE:
<223> OTHER INFORMATION: D2E7 light chain variable region CDR3
<221> NAME/KEY: VARIANT
<222> LOCATION: 9
<223> OTHER INFORMATION: Xaa = Any Amino Acid

<400> SEQUENCE: 3

Gln Arg Tyr Asn Arg Ala Pro Tyr Xaa
 1               5

<210> SEQ ID NO 4
<211> LENGTH: 12
<212> TYPE: PRT
<213> ORGANISM: Artificial
<220> FEATURE:
<223> OTHER INFORMATION: D2E7 heavy chain variable region CDR3
<221> NAME/KEY: VARIANT
<222> LOCATION: 12
<223> OTHER INFORMATION: Xaa = Any Amino Acid

<400> SEQUENCE: 4

Val Ser Tyr Leu Ser Thr Ala Ser Ser Leu Asp Xaa
 1               5                  10

<210> SEQ ID NO 5
<211> LENGTH: 7
<212> TYPE: PRT
<213> ORGANISM: Artificial
<220> FEATURE:
<223> OTHER INFORMATION: D2E7 light chain variable region CDR2

<400> SEQUENCE: 5

Ala Ala Ser Thr Leu Gln Ser
 1               5

<210> SEQ ID NO 6
<211> LENGTH: 17
<212> TYPE: PRT
<213> ORGANISM: Artificial
<220> FEATURE:
<223> OTHER INFORMATION: D2E7 heavy chain variable region CDR2

<400> SEQUENCE: 6

Ala Ile Thr Trp Asn Ser Gly His Ile Asp Tyr Ala Asp Ser Val Glu
 1               5                  10                  15

Gly

<210> SEQ ID NO 7
<211> LENGTH: 11
<212> TYPE: PRT
<213> ORGANISM: Artificial
<220> FEATURE:
<223> OTHER INFORMATION: D2E7 light chain variable region CDR1

<400> SEQUENCE: 7

Arg Ala Ser Gln Gly Ile Arg Asn Tyr Leu Ala
 1               5                  10

<210> SEQ ID NO 8
<211> LENGTH: 5
<212> TYPE: PRT
<213> ORGANISM: Artificial
<220> FEATURE:
<223> OTHER INFORMATION: D2E7 heavy chain variable region CDR1

<400> SEQUENCE: 8
```

```
Asp Tyr Ala Met His
 1               5
```

<210> SEQ ID NO 9
<211> LENGTH: 107
<212> TYPE: PRT
<213> ORGANISM: Artificial
<220> FEATURE:
<223> OTHER INFORMATION: 2SD4 light chain variable region

<400> SEQUENCE: 9

```
Asp Ile Gln Met Thr Gln Ser Pro Ser Leu Ser Ala Ser Ile Gly
 1               5                  10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Tyr
                85                  90                  95

Ala Phe Gly Gln Gly Thr Lys Val Glu Ile Lys
            100                 105
```

<210> SEQ ID NO 10
<211> LENGTH: 121
<212> TYPE: PRT
<213> ORGANISM: Artificial
<220> FEATURE:
<223> OTHER INFORMATION: 2SD4 heavy chain variable region

<400> SEQUENCE: 10

```
Gln Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Asp Trp Val
        35                  40                  45

Ser Ala Ile Thr Trp Asn Ser Gly His Ile Asp Tyr Ala Asp Ser Val
    50                  55                  60

Glu Gly Arg Phe Ala Val Ser Arg Asp Asn Ala Lys Asn Ala Leu Tyr
65                  70                  75                  80

Leu Gln Met Asn Ser Leu Arg Pro Glu Asp Thr Ala Val Tyr Tyr Cys
                85                  90                  95

Thr Lys Ala Ser Tyr Leu Ser Thr Ser Ser Ser Leu Asp Asn Trp Gly
            100                 105                 110

Gln Gly Thr Leu Val Thr Val Ser Ser
        115                 120
```

<210> SEQ ID NO 11
<211> LENGTH: 9
<212> TYPE: PRT
<213> ORGANISM: Artificial
<220> FEATURE:
<223> OTHER INFORMATION: 2SD4 light chain variable region CDR3

<400> SEQUENCE: 11

```
Gln Lys Tyr Asn Ser Ala Pro Tyr Ala
  1               5

<210> SEQ ID NO 12
<211> LENGTH: 9
<212> TYPE: PRT
<213> ORGANISM: Artificial
<220> FEATURE:
<223> OTHER INFORMATION: EP B12  light chain variable region CDR3

<400> SEQUENCE: 12

Gln Lys Tyr Asn Arg Ala Pro Tyr Ala
  1               5

<210> SEQ ID NO 13
<211> LENGTH: 9
<212> TYPE: PRT
<213> ORGANISM: Artificial
<220> FEATURE:
<223> OTHER INFORMATION: VL10E4 light chain variable region CDR3

<400> SEQUENCE: 13

Gln Lys Tyr Gln Arg Ala Pro Tyr Thr
  1               5

<210> SEQ ID NO 14
<211> LENGTH: 9
<212> TYPE: PRT
<213> ORGANISM: Artificial
<220> FEATURE:
<223> OTHER INFORMATION: VL100A9 light chain variable region CDR3

<400> SEQUENCE: 14

Gln Lys Tyr Ser Ser Ala Pro Tyr Thr
  1               5

<210> SEQ ID NO 15
<211> LENGTH: 9
<212> TYPE: PRT
<213> ORGANISM: Artificial
<220> FEATURE:
<223> OTHER INFORMATION: VLL100D2 light chain variable region CDR3

<400> SEQUENCE: 15

Gln Lys Tyr Asn Ser Ala Pro Tyr Thr
  1               5

<210> SEQ ID NO 16
<211> LENGTH: 9
<212> TYPE: PRT
<213> ORGANISM: Artificial
<220> FEATURE:
<223> OTHER INFORMATION: VLL0F4 light chain variable region CDR3

<400> SEQUENCE: 16

Gln Lys Tyr Asn Arg Ala Pro Tyr Thr
  1               5

<210> SEQ ID NO 17
<211> LENGTH: 9
<212> TYPE: PRT
<213> ORGANISM: Artificial
<220> FEATURE:
<223> OTHER INFORMATION: LOE5 light chain variable region CDR3

<400> SEQUENCE: 17

Gln Lys Tyr Asn Ser Ala Pro Tyr Tyr
```

```
<210> SEQ ID NO 18
<211> LENGTH: 9
<212> TYPE: PRT
<213> ORGANISM: Artificial
<220> FEATURE:
<223> OTHER INFORMATION: VLLOG7 light chain variable region CDR3

<400> SEQUENCE: 18

Gln Lys Tyr Asn Ser Ala Pro Tyr Asn
1               5

<210> SEQ ID NO 19
<211> LENGTH: 9
<212> TYPE: PRT
<213> ORGANISM: Artificial
<220> FEATURE:
<223> OTHER INFORMATION: VLLOG9 light chain variable region CDR3

<400> SEQUENCE: 19

Gln Lys Tyr Thr Ser Ala Pro Tyr Thr
1               5

<210> SEQ ID NO 20
<211> LENGTH: 9
<212> TYPE: PRT
<213> ORGANISM: Artificial
<220> FEATURE:
<223> OTHER INFORMATION: VLLOH1 light chain variable region CDR3

<400> SEQUENCE: 20

Gln Lys Tyr Asn Arg Ala Pro Tyr Asn
1               5

<210> SEQ ID NO 21
<211> LENGTH: 9
<212> TYPE: PRT
<213> ORGANISM: Artificial
<220> FEATURE:
<223> OTHER INFORMATION: VLLOH10 light chain variable region CDR3

<400> SEQUENCE: 21

Gln Lys Tyr Asn Ser Ala Ala Tyr Ser
1               5

<210> SEQ ID NO 22
<211> LENGTH: 9
<212> TYPE: PRT
<213> ORGANISM: Artificial
<220> FEATURE:
<223> OTHER INFORMATION: VL1B7 light chain variable region CDR3

<400> SEQUENCE: 22

Gln Gln Tyr Asn Ser Ala Pro Asp Thr
1               5

<210> SEQ ID NO 23
<211> LENGTH: 9
<212> TYPE: PRT
<213> ORGANISM: Artificial
<220> FEATURE:
<223> OTHER INFORMATION: VL1C1 light chain variable region CDR3

<400> SEQUENCE: 23

Gln Lys Tyr Asn Ser Asp Pro Tyr Thr
1               5
```

```
<210> SEQ ID NO 24
<211> LENGTH: 9
<212> TYPE: PRT
<213> ORGANISM: Artificial
<220> FEATURE:
<223> OTHER INFORMATION: VL0.1F4 light chain variable region CDR3

<400> SEQUENCE: 24

Gln Lys Tyr Ile Ser Ala Pro Tyr Thr
 1               5

<210> SEQ ID NO 25
<211> LENGTH: 9
<212> TYPE: PRT
<213> ORGANISM: Artificial
<220> FEATURE:
<223> OTHER INFORMATION: VL0.1H8 light chain variable region CDR3

<400> SEQUENCE: 25

Gln Lys Tyr Asn Arg Pro Pro Tyr Thr
 1               5

<210> SEQ ID NO 26
<211> LENGTH: 9
<212> TYPE: PRT
<213> ORGANISM: Artificial
<220> FEATURE:
<223> OTHER INFORMATION: LOE7.A light chain variable region CDR3

<400> SEQUENCE: 26

Gln Arg Tyr Asn Arg Ala Pro Tyr Ala
 1               5

<210> SEQ ID NO 27
<211> LENGTH: 12
<212> TYPE: PRT
<213> ORGANISM: Artificial
<220> FEATURE:
<223> OTHER INFORMATION: 2SD4 heavy chain variable region CDR3

<400> SEQUENCE: 27

Ala Ser Tyr Leu Ser Thr Ser Ser Ser Leu Asp Asn
 1               5                   10

<210> SEQ ID NO 28
<211> LENGTH: 12
<212> TYPE: PRT
<213> ORGANISM: Artificial
<220> FEATURE:
<223> OTHER INFORMATION: VH1B11 heavy chain variable region CDR3

<400> SEQUENCE: 28

Ala Ser Tyr Leu Ser Thr Ser Ser Ser Leu Asp Lys
 1               5                   10

<210> SEQ ID NO 29
<211> LENGTH: 12
<212> TYPE: PRT
<213> ORGANISM: Artificial
<220> FEATURE:
<223> OTHER INFORMATION: VH1D8 heavy chain variable region CDR3

<400> SEQUENCE: 29

Ala Ser Tyr Leu Ser Thr Ser Ser Ser Leu Asp Tyr
 1               5                   10
```

```
<210> SEQ ID NO 30
<211> LENGTH: 12
<212> TYPE: PRT
<213> ORGANISM: Artificial
<220> FEATURE:
<223> OTHER INFORMATION: VH1A11 heavy chain variable region CDR3

<400> SEQUENCE: 30

Ala Ser Tyr Leu Ser Thr Ser Ser Ser Leu Asp Asp
1               5                   10

<210> SEQ ID NO 31
<211> LENGTH: 12
<212> TYPE: PRT
<213> ORGANISM: Artificial
<220> FEATURE:
<223> OTHER INFORMATION: VH1B12 heavy chain variable region CDR3

<400> SEQUENCE: 31

Ala Ser Tyr Leu Ser Thr Ser Phe Ser Leu Asp Tyr
1               5                   10

<210> SEQ ID NO 32
<211> LENGTH: 12
<212> TYPE: PRT
<213> ORGANISM: Artificial
<220> FEATURE:
<223> OTHER INFORMATION: VH1E4 heavy chain variable region CDR3

<400> SEQUENCE: 32

Ala Ser Tyr Leu Ser Thr Ser Ser Ser Leu His Tyr
1               5                   10

<210> SEQ ID NO 33
<211> LENGTH: 12
<212> TYPE: PRT
<213> ORGANISM: Artificial
<220> FEATURE:
<223> OTHER INFORMATION: VH1F6 heavy chain variable region CDR3

<400> SEQUENCE: 33

Ala Ser Phe Leu Ser Thr Ser Ser Ser Leu Glu Tyr
1               5                   10

<210> SEQ ID NO 34
<211> LENGTH: 12
<212> TYPE: PRT
<213> ORGANISM: Artificial
<220> FEATURE:
<223> OTHER INFORMATION: 3C-H2 heavy chain variable region CDR3

<400> SEQUENCE: 34

Ala Ser Tyr Leu Ser Thr Ala Ser Ser Leu Glu Tyr
1               5                   10

<210> SEQ ID NO 35
<211> LENGTH: 12
<212> TYPE: PRT
<213> ORGANISM: Artificial
<220> FEATURE:
<223> OTHER INFORMATION: VH1-D2.N heavy chain variable region CDR3

<400> SEQUENCE: 35

Val Ser Tyr Leu Ser Thr Ala Ser Ser Leu Asp Asn
1               5                   10
```

```
<210> SEQ ID NO 36
<211> LENGTH: 321
<212> TYPE: DNA
<213> ORGANISM: Artificial
<220> FEATURE:
<223> OTHER INFORMATION: D2E7 light chain variable region

<400> SEQUENCE: 36
gacatccaga tgacccagtc tccatcctcc ctgtctgcat ctgtagggga cagagtcacc      60
atcacttgtc gggcaagtca gggcatcaga aattacttag cctggtatca gcaaaaacca     120
gggaaagccc ctaagctcct gatctatgct gcatccactt tgcaatcagg ggtcccatct     180
cggttcagtg gcagtggatc tgggacagat ttcactctca ccatcagcag cctacagcct     240
gaagatgttg caacttatta ctgtcaaagg tataaccgtg caccgtatac ttttggccag     300
gggaccaagg tggaaatcaa a                                               321

<210> SEQ ID NO 37
<211> LENGTH: 363
<212> TYPE: DNA
<213> ORGANISM: Artificial
<220> FEATURE:
<223> OTHER INFORMATION: D2E7 heavy chain variable region

<400> SEQUENCE: 37
gaggtgcagc tggtggagtc tgggggaggc ttggtacagc ccggcaggtc cctgagactc      60
tcctgtgcgg cctctggatt cacctttgat gattatgcca tgcactgggt ccggcaagct     120
ccagggaagg gcctggaatg ggtctcagct atcacttgga atagtggtca catagactat     180
gcggactctg tggagggccg attcaccatc tccagagaca cgccaagaa ctccctgtat      240 ctgcaaatga acagtctgag agctgaggat acggccgtat attactgtgc gaaagtctcg     300
taccttagca ccgcgtcctc ccttgactat tggggccaag taccctggt caccgtctcg      360 agt                                                                    363
```

METHOD OF TREATING ANKYLOSING SPONDYLITIS

RELATED APPLICATIONS

This application is a continuation application of U.S. Non-Provisional patent application Ser. No. 11/811,355, filed on Jun. 8, 2007 which claims priority to U.S. Provisional Patent Application No. 60/812,312, filed on Jun. 8, 2006; U.S. Provisional Patent Application No. 60/857,352, filed on Nov. 6, 2006; and U.S. Provisional Patent Application No. 60/858,328, filed on Nov. 10, 2006 the entire contents of each of which are incorporated herein by reference.

BACKGROUND OF THE INVENTION

Ankylosing spondylitis (AS) is a chronic, progressive, inflammatory disease with considerable impact on patient functioning, well-being, and disability. The prevalence of AS has traditionally been estimated in the range of 0.1-1.9%, with more males affected than females (Sieper et al. Ann Rheum Dis 2001; 60:3-18; Silman & Hochberg Rheum Dis Clin North Am 1996; 22:737-49; Gran & Husby, Semin Arthritis Rheum 1993; 22(5):319-34.). Millions of people are affected by ankylosing spondylitis (AS). As a chronic disease of the axial skeleton and large peripheral joints, AS causes inflammatory back pain and stiffness and it is associated with other inflammatory diseases of the skin, eyes and intestines. AS is difficult to diagnose in its early stages and is often an overlooked cause of persistent back pain in young adults. In severe cases, AS may result in complete spinal fusion, causing extreme physical limitation. Thus, there remains a need for a safe and effective treatment for AS.

As the disease progresses, patients with AS experience pain, joint stiffness, and the eventual loss of spinal mobility. These clinical symptoms and subsequent disease progression result in functional limitations and impairment in health-related quality of life (HRQOL) (Dagfinrud et al. Ann Rheum Dis 2004:63:1605-10; Bostan et al. Rheumatol Int 2003; 23:121-6; Zink et al., J Rheumatol 2000; 27:613-22; Ward 1998, Rheum Dis Clin North Am 1998; 24:815-27) and work productivity (Boonen et al. Ann Rheum Dis 2002; 61:429-37; Boonen et al. J Rheumatol 2001; 28:1056-62).

No cure exists for AS. Generally, treatment includes trying to relieve pain and stiffness using medications such as non-steroidal anti-inflammatory drugs (NSAIDs), corticosteroids, and disease-modifying antirheumatic drugs (DMARDs). In recent years biologic response modifiers that inhibit TNF activity have become established therapies for AS.

SUMMARY OF THE INVENTION

Although TNFα inhibitors are effective at treating AS, there remains a need for a more effective treatment option for subjects suffering from AS, especially in improving the fatigue and pain associated with the disease and in treating subjects who have failed more conventional, i.e., DMARD or NSAIDs therapy. Thus, there also remains a need for improved methods and compositions that provide a safe and effective treatment of AS using TNFα inhibitors.

The instant invention provides improved methods and compositions for treating AS. The invention further provides a means for treating certain subpopulations of patients who have AS. The invention further provides a means by which the efficacy of a TNFα inhibitor for the treatment of AS can be determined. Each of the examples described herein describes methods and compositions which can be used to determine whether a TNFα inhibitor is effective for treating the given disorder, i.e. AS.

The invention provides a method of decreasing pain and fatigue in a subject having AS comprising administering a human TNFα antibody, or antigen-binding portion thereof, to the subject such that pain and fatigue are decreased. In one embodiment, the decrease in fatigue in the subject is determined by a score selected from the group consisting of FACIT-F, BASDAI, and SF-36. In one embodiment, the decrease in fatigue is determined by a decrease of at least about 1.9 in a BASDAI score of the subject. In one embodiment, the decrease in fatigue is determined by a decrease of at least about 2.0 in a BASDAI score of the subject.

The invention also provides a method of inducing partial remission of AS in a subject comprising administering a human TNFα antibody, or antigen-binding portion thereof, to the subject, such that partial remission of AS is induced.

The invention further provides a method of treating AS in a subject who has failed either DMARD therapy or NSAIDs therapy comprising administering a human TNFα antibody, or antigen-binding portion thereof, to the subject, such that AS is treated.

The invention includes methods for determining the efficacy of a TNFα inhibitor for treating ankylosing spondylitis (AS) in a subject comprising determining a partial remission rate of a patient population having AS and who was administered the TNFα inhibitor, wherein a partial remission rate of at least about 20% of the patient population indicates that the TNFα inhibitor is an effective TNFα inhibitor for the treatment of AS.

The invention further provides a method of determining the efficacy of a TNFα inhibitor for treating ankylosing spondylitis (AS) in a subject comprising determining a Bath Ankylosing Spondylitis Disease Activity Index (BASDAI) 20 response of a patient population having AS and who was administered the TNFα inhibitor, wherein a BASDAI 20 response in at least about 60% of the patient population indicates that the TNFα inhibitor is an effective TNFα inhibitor for the treatment of AS. In one embodiment, a BASDAI 20 response in at least about 70% of the patient population indicates that the TNFα inhibitor is an effective TNFα inhibitor for the treatment of AS. In one embodiment, a BASDAI 20 response in at least about 80% of the patient population indicates that the TNFα inhibitor is an effective TNFα inhibitor for the treatment of AS. In one embodiment, a BASDAI 20 response in at least about 85% of the patient population indicates that the TNFα inhibitor is an effective TNFα inhibitor for the treatment of AS.

The invention includes a method of determining the efficacy of a TNFα inhibitor for treating ankylosing spondylitis (AS) in a subject comprising determining a Bath Ankylosing Spondylitis Disease Activity Index (BASDAI) 50 response of a patient population having AS and who was administered the TNFα inhibitor, wherein a BASDAI 50 response in at least about 23% of the patient population indicates that the TNFα inhibitor is an effective TNFα inhibitor for the treatment of AS. In one embodiment, a BASDAI 50 response in at least about 30% of the patient population indicates that the TNFα inhibitor is an effective TNFα inhibitor for the treatment of AS. In one embodiment, a BASDAI 50 response in at least about 40% of the patient population indicates that the TNFα inhibitor is an effective TNFα inhibitor for the treatment of AS. In one embodiment, a BASDAI 50 response in at least about 50% of the patient population indicates that the TNFα inhibitor is an effective TNFα inhibitor for the treatment of AS. In one embodiment, a BASDAI 50 response in at least about 60% of the patient population indicates that the TNFα inhibitor is an effective TNFα inhibitor for the treatment of AS.

The invention further provides a method of determining the efficacy of a TNFα inhibitor for treating ankylosing spondylitis (AS) in a subject comprising determining a Bath Ankylosing Spondylitis Disease Activity Index (BASDAI) 70 response of a patient population having AS and who was administered the TNFα inhibitor, wherein a BASDAI 70 response in at least about 10% of the patient population indicates that the TNFα inhibitor is an effective TNFα inhibitor for the treatment of AS. The invention also includes a BASDAI 70 response in at least about 20% of the patient population indicates that the TNFα inhibitor is an effective TNFα inhibitor for the treatment of AS. In one embodiment, a BASDAI 70 response in at least about 30% of the patient population indicates that the TNFα inhibitor is an effective TNFα inhibitor for the treatment of AS. In one embodiment, a BASDAI 70 response in at least about 40% of the patient population indicates that the TNFα inhibitor is an effective TNFα inhibitor for the treatment of AS. In one embodiment, a BASDAI 70 response in at least about 45% of the patient population indicates that the TNFα inhibitor is an effective TNFα inhibitor for the treatment of AS.

The invention describes a method of determining the efficacy of a TNFα inhibitor for treating ankylosing spondylitis (AS) in a subject comprising determining a Assessment in Ankylosing Spondylitis (ASAS) 20 response of a patient population having AS and who was administered the TNFα inhibitor, wherein an ASAS20 response in at least about 27% of the patient population indicates that the TNFα inhibitor is an effective TNFα inhibitor for the treatment of AS. In one embodiment, an ASAS20 response in at least about 50% of the patient population indicates that the TNFα inhibitor is an effective TNFα inhibitor for the treatment of AS. In one embodiment, an ASAS20 response in at least about 55% of the patient population indicates that the TNFα inhibitor is an effective TNFα inhibitor for the treatment of AS. In one embodiment, an ASAS20 response in at least about 70% of the patient population indicates that the TNFα inhibitor is an effective TNFα inhibitor for the treatment of AS.

The invention provides a method of determining the efficacy of a TNFα inhibitor for treating ankylosing spondylitis (AS) in a subject comprising determining a Assessment in Ankylosing Spondylitis (ASAS) 40 response of a patient population having AS and who was administered the TNFα inhibitor, wherein an ASAS40 response in at least about 10% of the patient population indicates that the TNFα inhibitor is an effective TNFα inhibitor for the treatment of AS. In one embodiment, an ASAS40 response in at least about 20% of the patient population indicates that the TNFα inhibitor is an effective TNFα inhibitor for the treatment of AS. In one embodiment, an ASAS40 response in at least about 30% of the patient population indicates that the TNFα inhibitor is an effective TNFα inhibitor for the treatment of AS. In one embodiment, an ASAS40 response in at least about 45% of the patient population indicates that the TNFα inhibitor is an effective TNFα inhibitor for the treatment of AS in the subject.

The invention includes a method of determining the efficacy of a TNFα inhibitor for treating ankylosing spondylitis (AS) in a subject comprising determining a Assessment in Ankylosing Spondylitis (ASAS) 70 response of a patient population having AS and who was administered the TNFα inhibitor, wherein an ASAS70 response in at least about 5% of the patient population indicates that the TNFα inhibitor is an effective TNFα inhibitor for the treatment of AS. In one embodiment, an ASAS70 response in at least about 20% of the patient population indicates that the TNFα inhibitor is an effective TNFα inhibitor for the treatment of AS in the subject. In one embodiment, an ASAS70 response in at least about 23% of the patient population indicates that the TNFα inhibitor is an effective TNFα inhibitor for the treatment of AS in the subject. In one embodiment, an ASAS70 response in at least about 30% of the patient population indicates that the TNFα inhibitor is an effective TNFα inhibitor for the treatment of AS in the subject. In one embodiment, an ASAS70 response in at least about 40% of the patient population indicates that the TNFα inhibitor is an effective TNFα inhibitor for the treatment of AS in the subject.

In one embodiment, the invention further comprises administering the effective TNFα inhibitor to a subject to treat AS.

The invention also includes a method of treating AS in a subject comprising administering an effective TNFα inhibitor to the subject such that AS is treated, wherein the effective TNFα inhibitor was previously identified as resulting in a BASDAI 20 response in at least about 60% of a patient population having AS and who was administered the TNFα inhibitor.

The invention further provides a method of treating AS in a subject comprising administering an effective TNFα inhibitor to the subject such that AS is treated, wherein the effective TNFα inhibitor was previously identified as resulting in a BASDAI 50 response in at least about 23% of a patient population having AS and who was administered the TNFα inhibitor.

The invention provides a method of treating AS in a subject comprising administering an effective TNFα inhibitor to the subject such that AS is treated, wherein the effective TNFα inhibitor was previously identified as resulting in a BASDAI 70 response in at least about 10% of a patient population having AS and who was administered the TNFα inhibitor.

The invention also provides a method of treating AS in a subject comprising administering an effective TNFα inhibitor to the subject such that AS is treated, wherein the effective TNFα inhibitor was previously identified as resulting in an ASAS20 response in at least about 50% of a patient population having AS who was administered the TNFα inhibitor.

The invention includes a method of treating AS in a subject comprising administering an effective human TNFα antibody, or antigen-binding portion thereof, to the subject, wherein the effective human TNFα antibody, or antigen-binding portion thereof, was previously identified as achieving an ASAS50 response in at least about 39% of a patient population having AS who was administered the human TNFα antibody, or antigen-binding portion thereof.

The invention also includes a method of treating AS in a subject comprising administering an effective human TNFα antibody, or antigen-binding portion thereof, to the subject, wherein the effective human TNFα antibody, or antigen-binding portion thereof, was previously identified as achieving an ASAS70 response in at least about 5% of a patient population having AS who was administered the human TNFα antibody, or antigen-binding portion thereof.

The invention provides a method for monitoring the effectiveness of a TNFα inhibitor for the treatment of fatigue in a human subject having AS comprising administering the TNFα inhibitor to the subject; and determining the effectiveness of the TNFα inhibitor using a baseline FACIT-fatigue score and a FACIT-fatigue score following administration of the TNFα inhibitor, wherein either a change of at least about 7 for the FACIT-fatigue score indicates that the TNFα inhibitor is effective at reducing fatigue in a subject having AS.

The invention includes a method of testing the effectiveness of a TNFα inhibitor for decreasing fatigue in a patient having AS, comprising comparing a pre-determined FACIT-fatigue score following treatment of the patient with the TNFα inhibitor, with a pre-determined FACIT-fatigue baseline score, wherein a change of at least about 7 indicates the TNFα inhibitor is effective for decreasing fatigue in a patient having AS.

The invention includes a method of achieving partial remission of a patient having AS comprising administering to the patient a TNFα inhibitor.

The invention provides a method for monitoring the effectiveness of a TNFα inhibitor for the treatment of ankylosing spondylitis (AS) in a human subject comprising using a mean baseline AS Quality of Life Questionnaire (ASQoL) of a patient population having AS and a mean ASQoL score of the patient population following administration of the TNFα inhibitor, wherein a mean decrease in the ASQoL score of at least about 3 indicates that the TNFα inhibitor is effective at treating AS. In one embodiment, the TNFα inhibitor has already been administered to the pre-selected patient population.

The invention also provides a method for monitoring the effectiveness of a TNFα inhibitor for the treatment of ankylosing spondylitis (AS) in a human subject comprising using a mean baseline Maastricht AS Enthesitis Score (MASES) of a patient population having AS and a mean MASES score of the patient population following administration of the TNFα inhibitor, wherein a mean decrease in the MASES score of at least about 2 indicates that the TNFα inhibitor is effective at treating AS. In one embodiment, the TNFα inhibitor has already been administered to the pre-selected patient population.

The invention also provides a method of testing the effectiveness of a TNFα inhibitor for the treatment of ankylosing spondylitis (AS) comprising using a mean baseline BASDAI score of a preselected patient population having AS and a mean BASDAI score of the patient population following administration of the TNFα inhibitor, wherein a BASDAI20 response rate in at least about 70% of the patient population indicates the TNFα inhibitor is effective for the treatment of AS.

The invention further provides a method of testing the effectiveness of a TNFα inhibitor for the treatment of ankylosing spondylitis (AS) comprising using a mean baseline BASDAI score of a preselected patient population having AS and a mean BASDAI score of the patient population following administration of the TNFα inhibitor, wherein a BASDAI70 response rate in at least about 25% of the patient population indicates the TNFα inhibitor is effective for the treatment of AS.

In one embodiment, the patient population has a mean BASDAI of about 6.6.

In another embodiment, the TNFα inhibitor is selected from the group consisting of a TNFα antibody, or an antigen-binding portion thereof, a TNF fusion protein, or a recombinant TNF binding protein.

In another embodiment, the TNF fusion protein is etanercept.

In still another embodiment, the TNFα antibody, or antigen-binding portion thereof, is selected from the group consisting of a chimeric antibody, a humanized antibody, and a multivalent antibody. In one embodiment, the TNFα antibody, or antigen-binding portion thereof, is a human antibody.

In one embodiment, the TNFα antibody, or antigen-binding portion thereof, is an isolated human antibody that dissociates from human TNFα with a $K_d$ of $1 \times 10^{-8}$ M or less and a $K_{off}$ rate constant of $1 \times 10^{-3}$ s$^{-1}$ or less, both determined by surface plasmon resonance, and neutralizes human TNFα cytotoxicity in a standard in vitro L929 assay with an $IC_{50}$ of $1 \times 10^{-7}$ M or less.

In another embodiment, the TNFα antibody is an isolated human antibody, or antigen-binding portion thereof, with the following characteristics:

a) dissociates from human TNFα with a $K_{off}$ rate constant of $1 \times 10^{-3}$ s$^{-1}$ or less, as determined by surface plasmon resonance;

b) has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9;

c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12.

In another embodiment, the TNFα antibody is an isolated human antibody, or an antigen binding portion thereof, with a light chain variable region (LCVR) comprising the amino acid sequence of SEQ ID NO: 1 and a heavy chain variable region (HCVR) comprising the amino acid sequence of SEQ ID NO: 2.

In one embodiment, the human TNFα antibody, or antigen-binding portion thereof, is adalimumab.

In one embodiment, the TNFα antibody, or antigen-binding portion thereof, is a 40 mg dose.

In another embodiment, the TNFα antibody, or antigen-binding portion thereof, is administered subcutaneously.

In still another embodiment, the TNFα antibody, or antigen-binding portion thereof, is infliximab or golimumab.

BRIEF DESCRIPTION OF THE DRAWINGS

FIG. 1 graphically depicts the improvement of BASDAI20, 50 and 70 after 2, 12 and 52 weeks of treatment with adalimumab.

FIG. 2 shows the improvement of ASAS20, 40 and 70 criteria after 2, 12 and 52 weeks of treatment with adalimumab.

FIG. 3 describes an overview of the Canadian AS study design. The dashed line indicates the early escape option at Weeks 22, 16, and 20.

FIG. 4 shows the change in mean FACIT-Fatigue score by treatment group over time.

FIG. 5 shows the change in mean BASDAI-fatigue item score by treatment group over time.

FIG. 6 shows the mean SF-36 vitality domain score by treatment group over time.

FIG. 7 outlines the Study H design. The dashed line indicates the early escape option at Weeks 22, 16, and 20.

FIG. 8 graphically depicts the ASA40 response through Week 24. *** Statistically significant at p=0.001 level, wherein the p value is from Pearson's Chi-square test. ASAS40 values are imputed.

FIG. 9 depicts the ASA20 response for those patients who switched to EET at Week 12 of the Canadian AS study. Data includes patients who entered early-escape open-label therapy at Week 14.

FIG. 10 depicts the ASAS20 response time course observed in patients from the Canadian AS study. Observed analysis excludes patients with missing data, but includes patients who remained on randomized study drug or who elected early escape treatment. A statistically significant difference was present between adalimumab and placebo treatment groups at the p=0.01 level.

FIG. 11 graphically depicts the time course of ASAS 20 (Imputed) in patients enrolled in Study H. Patients who received early escape therapy or discontinued are counted as non-responders at Weeks 12 and 24. ***Statistically significant at p=0.001 level.

DETAILED DESCRIPTION OF THE INVENTION

I. Definitions

The term "human TNFα" (abbreviated herein as hTNFα, or simply hTNF), as used herein, is intended to refer to a human cytokine that exists as a 17 kD secreted form and a 26 kD membrane associated form, the biologically active form of which is composed of a trimer of noncovalently bound 17 kD molecules. The structure of hTNFα is described further in, for example, Pennica, D., et al. (1984) Nature 312:724-729; Davis, J. M., et al. (1987) Biochemistry 26:1322-1326; and Jones, E. Y., et al. (1989) Nature 338:225-228. The term human TNFα is intended to include recombinant human TNFα (rhTNFα), which can be prepared by standard recombinant expression methods or purchased commercially (R & D Systems, Catalog No. 210-TA, Minneapolis, Minn.). TNFα is also referred to as TNF.

The term "TNFα inhibitor" includes agents which interfere with TNFα activity. The term also includes each of the anti-TNFα human antibodies and antibody portions described herein as well as those described in U.S. Pat. Nos. 6,090,382; 6,258,562; 6,509,015, and in U.S. patent application Ser. Nos. 09/801,185 and 10/302,356. In one embodiment, the TNFα inhibitor used in the invention is an anti-TNFα antibody, or a fragment thereof, including infliximab (Remicade®, Johnson and Johnson; described in U.S. Pat. No. 5,656,272, incorporated by reference herein), CDP571 (a humanized monoclonal anti-TNF-alpha IgG4 antibody), CDP 870 (a humanized monoclonal anti-TNF-alpha antibody fragment), an anti-TNF dAb (Peptech), CNTO 148 (golimumab; Medarex and Centocor, see WO 02/12502), and adalimumab (HUMIRA® Abbott Laboratories, a human anti-TNF mAb, described in U.S. Pat. No. 6,090,382 as D2E7). Additional TNF antibodies which may be used in the invention are described in U.S. Pat. Nos. 6,593,458; 6,498,237; 6,451,983; and 6,448,380, each of which is incorporated by reference herein. In another embodiment, the TNFα inhibitor is a TNF fusion protein, e.g., etanercept (Enbrel®, Amgen; described in WO 91/03553 and WO 09/406,476, incorporated by reference herein). In another embodiment, the TNFα inhibitor is a recombinant TNF binding protein (r-TBP-I) (Serono).

The term "antibody", as used herein, is intended to refer to immunoglobulin molecules comprised of four polypeptide chains, two heavy (H) chains and two light (L) chains interconnected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The antibodies of the invention are described in further detail in U.S. Pat. Nos. 6,090,382; 6,258,562; and 6,509,015, each of which is incorporated herein by reference in its entirety.

The term "antigen-binding portion" or "antigen-binding fragment" of an antibody (or simply "antibody portion"), as used herein, refers to one or more fragments of an antibody that retain the ability to specifically bind to an antigen (e.g., hTNFα). It has been shown that the antigen-binding function of an antibody can be performed by fragments of a full-length antibody. Binding fragments include Fab, Fab', F(ab')$_2$, Fabc, Fv, single chains, and single-chain antibodies. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) Nature 341:544-546), which consists of a VH or VL domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger et al. (1993) Proc. Natl. Acad. Sci. USA 90:6444-6448; Poljak et al. (1994) Structure 2:1121-1123). The antibody portions of the invention are described in further detail in U.S. Pat. Nos. 6,090, 382, 6,258,562, 6,509,015, each of which is incorporated herein by reference in its entirety.

Still further, an antibody or antigen-binding portion thereof may be part of a larger immunoadhesion molecules, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101) and use of a cysteine residue, a marker peptide and a C-terminal polyhistidine tag to make bivalent and biotinylated scFv molecules (Kipriyanov, S. M., et al. (1994) Mol. Immunol. 31:1047-1058). Antibody portions, such as Fab and F(ab)$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

A "conservative amino acid substitution", as used herein, is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

"Chimeric antibodies" refers to antibodies wherein one portion of each of the amino acid sequences of heavy and light chains is homologous to corresponding sequences in antibodies derived from a particular species or belonging to a particular class, while the remaining segment of the chains is homologous to corresponding sequences from another species. In one embodiment, the invention features a chimeric antibody or antigen-binding fragment, in which the variable regions of both light and heavy chains mimics the variable regions of antibodies derived from one species of mammals, while the constant portions are homologous to the sequences in antibodies derived from another species. In a preferred embodiment of the invention, chimeric antibodies are made by grafting CDRs from a mouse antibody onto the framework regions of a human antibody.

"Humanized antibodies" refer to antibodies which comprise at least one chain comprising variable region framework residues substantially from a human antibody chain (referred to as the acceptor immunoglobulin or antibody) and at least one complementarity determining region (CDR) substantially from a non-human-antibody (e.g., mouse). In addition to the grafting of the CDRs, humanized antibodies typically undergo further alterations in order to improve affinity and/or immunogenicity.

The term "multivalent antibody" refers to an antibody comprising more than one antigen recognition site. For example, a "bivalent" antibody has two antigen recognition sites, whereas a "tetravalent" antibody has four antigen recognition sites. The terms "monospecific", "bispecific", "trispecific", "tetraspecific", etc. refer to the number of different antigen recognition site specificities (as opposed to the number of antigen recognition sites) present in a multivalent antibody. For example, a "monospecific" antibody's antigen recognition sites all bind the same epitope. A "bispecific" or "dual specific" antibody has at least one antigen recognition site that binds a first epitope and at least one antigen recognition site that binds a second epitope that is different from the first epitope. A "multivalent monospecific" antibody has multiple antigen recognition sites that all bind the same epitope. A "multivalent bispecific" antibody has multiple antigen recognition sites, some number of which bind a first epitope and some number of which bind a second epitope that is different from the first epitope The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) *Nucl. Acids Res.* 20:6287) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

Such chimeric, humanized, human, and dual specific antibodies can be produced by recombinant DNA techniques known in the art, for example using methods described in PCT International Application No. PCT/US86/02269; European Patent Application No. 184,187; European Patent Application No. 171,496; European Patent Application No. 173,494; PCT International Publication No. WO 86/01533; U.S. Pat. No. 4,816,567; European Patent Application No. 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Cancer Res.* 47:999-1005; Wood et al. (1985) *Nature* 314:446-449; Shaw et al. (1988) *J. Natl. Cancer Inst.* 80:1553-1559); Morrison (1985) *Science* 229:1202-1207; Oi et al. (1986) *BioTechniques* 4:214; U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060, Queen et al., *Proc. Natl. Acad. Sci. USA* 86:10029-10033 (1989), U.S. Pat. No. 5,530,101, U.S. Pat. No. 5,585,089, U.S. Pat. No. 5,693,761, U.S. Pat. No. 5,693,762, Selick et al., WO 90/07861, and Winter, U.S. Pat. No. 5,225,539.

An "isolated antibody", as used herein, is intended to refer to an antibody that is substantially free of other antibodies having different antigenic specificities (e.g., an isolated antibody that specifically binds hTNFα is substantially free of antibodies that specifically bind antigens other than hTNFα). An isolated antibody that specifically binds hTNFα may, however, have cross-reactivity to other antigens, such as TNFα molecules from other species. Moreover, an isolated antibody may be substantially free of other cellular material and/or chemicals.

A "neutralizing antibody", as used herein (or an "antibody that neutralized hTNFα activity"), is intended to refer to an antibody whose binding to hTNFα results in inhibition of the biological activity of hTNFα. This inhibition of the biological activity of hTNFα can be assessed by measuring one or more indicators of hTNFα biological activity, such as hTNFα-induced cytotoxicity (either in vitro or in vivo), hTNFα-induced cellular activation and hTNFα binding to hTNFα receptors. These indicators of hTNFα biological activity can be assessed by one or more of several standard in vitro or in vivo assays known in the art (see U.S. Pat. No. 6,090,382).

Preferably, the ability of an antibody to neutralize hTNFα activity is assessed by inhibition of hTNFα-induced cytotoxicity of L929 cells. As an additional or alternative parameter of hTNFα activity, the ability of an antibody to inhibit hTNFα-induced expression of ELAM-1 on HUVEC, as a measure of hTNFα-induced cellular activation, can be assessed.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Example 1 of U.S. Pat. No. 6,258,562 and Jönsson et al. (1993) *Ann. Biol. Clin.* 51:19; Jönsson et al. (1991) *Biotechniques* 11:620-627; Johnsson et al. (1995) *J. Mol. Recognit.* 8:125; and Johnnson et al. (1991) *Anal. Biochem.* 198:268.

The term "$K_{off}$", as used herein, is intended to refer to the off rate constant for dissociation of an antibody from the antibody/antigen complex.

The term "$K_d$", as used herein, is intended to refer to the dissociation constant of a particular antibody-antigen interaction.

The term "$IC_{50}$" as used herein, is intended to refer to the concentration of the inhibitor required to inhibit the biological endpoint of interest, e.g., neutralize cytotoxicity activity.

The term "dose," as used herein, refers to an amount of TNFα inhibitor which is administered to a subject.

The term "dosing", as used herein, refers to the administration of a substance (e.g., an anti-TNFα antibody) to achieve a therapeutic objective (e.g., treatment of ankylosing spondylitis (AS)).

A "dosing regimen" describes a treatment schedule for a TNFα inhibitor, e.g., a treatment schedule over a prolonged period of time and/or throughout the course of treatment, e.g. administering a first dose of a TNFα inhibitor at week 0 followed by a second dose of a TNFα inhibitor on a biweekly dosing regimen.

The terms "biweekly dosing regimen", "biweekly dosing", and "biweekly administration", as used herein, refer to the time course of administering a substance (e.g., an anti-TNFα antibody) to a subject to achieve a therapeutic objective, e.g., throughout the course of treatment. The biweekly dosing regimen is not intended to include a weekly dosing regimen. Preferably, the substance is administered every 9-19 days, more preferably, every 11-17 days, even more preferably, every 13-15 days, and most preferably, every 14 days. In one embodiment, the biweekly dosing regimen is initiated in a subject at week 0 of treatment. In one embodiment, biweekly dosing includes a dosing regimen wherein doses of a TNFα inhibitor are administered to a subject every other week beginning at week 0. In one embodiment, biweekly dosing includes a dosing regimen where doses of a TNFα inhibitor are administered to a subject every other week consecutively for a given time period, e.g., 4 weeks, 8 weeks, 16, weeks, 24 weeks, etc. Biweekly dosing methods are also described in US 20030235585, incorporated by reference herein.

The term "combination" as in the phrase "a first agent in combination with a second agent" includes co-administration of a first agent and a second agent, which for example may be dissolved or intermixed in the same pharmaceutically acceptable carrier, or administration of a first agent, followed by the second agent, or administration of the second agent, followed by the first agent. The present invention, therefore, includes methods of combination therapeutic treatment and combination pharmaceutical compositions. In one embodiment, a TNFα antibody is administered in combination with methotrexate for the treatment of ankylosing spondylitis.

The term "concomitant" as in the phrase "concomitant therapeutic treatment" includes administering an agent in the presence of a second agent. A concomitant therapeutic treatment method includes methods in which the first, second, third, or additional agents are co-administered. A concomitant therapeutic treatment method also includes methods in which the first or additional agents are administered in the presence of a second or additional agents, wherein the second or additional agents, for example, may have been previously administered. A concomitant therapeutic treatment method may be executed step-wise by different actors. For example, one actor may administer to a subject a first agent and a second actor may to administer to the subject a second agent, and the administering steps may be executed at the same time, or nearly the same time, or at distant times, so long as the first agent (and additional agents) are after administration in the presence of the second agent (and additional agents). The actor and the subject may be the same entity (e.g., human).

The term "combination therapy", as used herein, refers to the administration of two or more therapeutic substances, e.g., an anti-TNFα antibody and another drug. The other drug(s) may be administered concomitant with, prior to, or following the administration of an anti-TNFα antibody.

The term "treatment," as used within the context of the present invention, is meant to include therapeutic treatment, as well as prophylactic or suppressive measures, for the treatment of ankylosing spondylitis. For example, the term treatment may include administration of a TNFα inhibitor prior to or following the onset of ankylosing spondylitis thereby preventing or removing signs of the disease or disorder. As another example, administration of a TNFα inhibitor after clinical manifestation of ankylosing spondylitis to combat the symptoms and/or complications and disorders associated with ankylosing spondylitis comprises "treatment" of the disease. Further, administration of the agent after onset and after clinical symptoms and/or complications have developed where administration affects clinical parameters of the disease or disorder and perhaps amelioration of the disease, comprises "treatment" of the ankylosing spondylitis.

Those "in need of treatment" include mammals, such as humans, already having AS, including those in which the disease or disorder is to be prevented.

The invention provides improved uses and compositions for treating ankylosing spondylitis with a TNFα inhibitor, e.g., a human TNFα antibody, or an antigen-binding portion thereof. Compositions and articles of manufacture, including kits, relating to the methods and uses for treating ankylosing spondylitis are also contemplated as part of the invention. Various aspects of the invention are described in further detail herein.

II. TNF Inhibitors

A TNFα inhibitor which is used in the methods and compositions of the invention includes any agent which interferes with TNFα activity. In a preferred embodiment, the TNFα inhibitor can neutralize TNFα activity, particularly detrimental TNFα activity which is associated with ankylosing spondylitis, and related complications and symptoms.

In one embodiment, the TNFα inhibitor used in the invention is an TNFα antibody (also referred to herein as a TNFα antibody), or an antigen-binding fragment thereof, including chimeric, humanized, and human antibodies. Examples of TNFα antibodies which may be used in the invention include, but not limited to, infliximab (Remicade®, Johnson and Johnson; described in U.S. Pat. No. 5,656,272, incorporated by reference herein), CDP571 (a humanized monoclonal anti-TNF-alpha IgG4 antibody), CDP 870 (a humanized monoclonal anti-TNF-alpha antibody fragment), an anti-TNF dAb (Peptech), CNTO 148 (golimumab; Medarex and Centocor, see WO 02/12502), and adalimumab (HUMIRA® Abbott Laboratories, a human anti-TNF mAb, described in U.S. Pat. No. 6,090,382 as D2E7). Additional TNF antibodies which may be used in the invention are described in U.S. Pat. Nos. 6,593,458; 6,498,237; 6,451,983; and 6,448,380, each of which is incorporated by reference herein.

Other examples of TNFα inhibitors which may be used in the methods and compositions of the invention include etanercept (Enbrel, described in WO 91/03553 and WO 09/406,476), soluble TNF receptor Type I, a pegylated soluble TNF receptor Type I (PEGs TNF-R1), p55TNFR1gG (Lenercept), and recombinant TNF binding protein (r-TBP-I) (Serono).

In one embodiment, the term "TNFα inhibitor" excludes infliximab. In one embodiment, the term "TNFα inhibitor" excludes adalimumab. In another embodiment, the term "TNFα inhibitor" excludes adalimumab and infliximab.

In one embodiment, the term "TNFα inhibitor" excludes etanercept, and, optionally, adalimumab, infliximab, or adalimumab and infliximab.

In one embodiment, the term "TNFα antibody" excludes infliximab. In one embodiment, the term "TNFα antibody" excludes adalimumab. In another embodiment, the term "TNFα antibody" excludes adalimumab and infliximab.

In one embodiment, the invention features uses and composition for treating or determining the efficacy of a TNFα inhibitor for the treatment of ankylosing spondylitis, wherein the TNFα antibody is an isolated human antibody, or antigen-binding portion thereof, that binds to human TNFα with high affinity and a low off rate, and also has a high neutralizing capacity. Preferably, the human antibodies used in the invention are recombinant, neutralizing human anti-hTNFα antibodies. The most preferred recombinant, neutralizing antibody of the invention is referred to herein as D2E7, also referred to as HUMIRA® or adalimumab (the amino acid sequence of the D2E7 VL region is shown in SEQ ID NO: 1; the amino acid sequence of the D2E7 VH region is shown in SEQ ID NO: 2). The properties of D2E7 (adalimumab/HUMIRA®) have been described in Salfeld et al., U.S. Pat. Nos. 6,090,382, 6,258,562, and 6,509,015, which are each incorporated by reference herein. The methods of the invention may also be performed using chimeric and humanized murine anti-hTNFα antibodies which have undergone clinical testing for treatment of rheumatoid arthritis (see e.g., Elliott, M. J., et al. (1994) *Lancet* 344:1125-1127; Elliot, M. J., et al. (1994) *Lancet* 344:1105-1110; Rankin, E. C., et al. (1995) *Br. J. Rheumatol.* 34:334-342).

In one embodiment, the method of the invention includes determining the efficacy of a TNFα inhibitor, including human antibodies and antibody portions with equivalent properties to D2E7, such as high affinity binding to hTNFα with low dissociation kinetics and high neutralizing capacity, for the treatment of ankylosing spondylitis. In one embodiment, the invention provides treatment with an isolated human antibody, or an antigen-binding portion thereof, that dissociates from human TNFα with a $K_d$ of $1 \times 10^{-8}$ M or less and a $K_{off}$ rate constant of $1 \times 10^{-3}$ s$^{-1}$ or less, both determined by surface plasmon resonance, and neutralizes human TNFα cytotoxicity in a standard in vitro L929 assay with an $IC_{50}$ of $1 \times 10^{-7}$ M or less. More preferably, the isolated human antibody, or antigen-binding portion thereof, dissociates from human TNFα with a $K_{off}$ of $5 \times 10^{-4}$ s$^{-1}$ or less, or even more preferably, with a $K_{off}$ of $1 \times 10^{-4}$ s$^{-1}$ or less. More preferably, the isolated human antibody, or antigen-binding portion thereof, neutralizes human TNFα cytotoxicity in a standard in vitro L929 assay with an $IC_{50}$ of $1 \times 10^{-8}$ M or less, even more preferably with an $IC_{50}$ of $1 \times 10^{-9}$ M or less and still more preferably with an $IC_{50}$ of $1 \times 10^{-10}$ M or less. In a preferred embodiment, the antibody is an isolated human recombinant antibody, or an antigen-binding portion thereof.

It is well known in the art that antibody heavy and light chain CDR3 domains play an important role in the binding specificity/affinity of an antibody for an antigen. Accordingly, in another aspect, the invention pertains to treating AS by administering human antibodies that have slow dissociation kinetics for association with hTNFα and that have light and heavy chain CDR3 domains that structurally are identical to or related to those of D2E7. Position 9 of the D2E7 VL CDR3 can be occupied by Ala or Thr without substantially affecting the $K_{off}$. Accordingly, a consensus motif for the D2E7 VL CDR3 comprises the amino acid sequence: Q-R-Y-N-R-A-P-Y-(T/A) (SEQ ID NO: 3). Additionally, position 12 of the D2E7 VH CDR3 can be occupied by Tyr or Asn, without substantially affecting the $K_{off}$. Accordingly, a consensus motif for the D2E7 VH CDR3 comprises the amino acid sequence: V-S-Y-L-S-T-A-S-S-L-D-(Y/N) (SEQ ID NO: 4). Moreover, as demonstrated in Example 2 of U.S. Pat. No. 6,090,382, the CDR3 domain of the D2E7 heavy and light chains is amenable to substitution with a single alanine residue (at position 1, 4, 5, 7 or 8 within the VL CDR3 or at position 2, 3, 4, 5, 6, 8, 9, 10 or 11 within the VH CDR3) without substantially affecting the $K_{off}$. Still further, the skilled artisan will appreciate that, given the amenability of the D2E7 VL and VH CDR3 domains to substitutions by alanine, substitution of other amino acids within the CDR3 domains may be possible while still retaining the low off rate constant of the antibody, in particular substitutions with conservative amino acids. Preferably, no more than one to five conservative amino acid substitutions are made within the D2E7 VL and/or VH CDR3 domains. More preferably, no more than one to three conservative amino acid substitutions are made within the D2E7 VL and/or VH CDR3 domains. Additionally, conservative amino acid substitutions should not be made at amino acid positions critical for binding to hTNFα. Positions 2 and 5 of the D2E7 VL CDR3 and positions 1 and 7 of the D2E7 VH CDR3 appear to be critical for interaction with hTNFα and thus, conservative amino acid substitutions preferably are not made at these positions (although an alanine substitution at position 5 of the D2E7 VL CDR3 is acceptable, as described above) (see U.S. Pat. No. 6,090,382).

Accordingly, in another embodiment, the antibody or antigen-binding portion thereof preferably contains the following characteristics:

a) dissociates from human TNFα with a $K_{off}$ rate constant of $1 \times 10^{-3}$ s$^{-1}$ or less, as determined by surface plasmon resonance;

b) has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9;

c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12.

More preferably, the antibody, or antigen-binding portion thereof, dissociates from human TNFα with a $K_{off}$ of $5 \times 10^{-4}$ $s^{-1}$ or less. Even more preferably, the antibody, or antigen-binding portion thereof, dissociates from human TNFα with a $K_{off}$ of $1 \times 10^{-4}$ $s^{-1}$ or less.

In yet another embodiment, the antibody or antigen-binding portion thereof preferably contains a light chain variable region (LCVR) having a CDR3 domain comprising the amino acid sequence of SEQ ID NO: 3, or modified from SEQ ID NO: 3 by a single alanine substitution at position 1, 4, 5, 7 or 8, and with a heavy chain variable region (HCVR) having a CDR3 domain comprising the amino acid sequence of SEQ ID NO: 4, or modified from SEQ ID NO: 4 by a single alanine substitution at position 2, 3, 4, 5, 6, 8, 9, 10 or 11. Preferably, the LCVR further has a CDR2 domain comprising the amino acid sequence of SEQ ID NO: 5 (i.e., the D2E7 VL CDR2) and the HCVR further has a CDR2 domain comprising the amino acid sequence of SEQ ID NO: 6 (i.e., the D2E7 VH CDR2). Even more preferably, the LCVR further has CDR1 domain comprising the amino acid sequence of SEQ ID NO: 7 (i.e., the D2E7 VL CDR1) and the HCVR has a CDR1 domain comprising the amino acid sequence of SEQ ID NO: 8 (i.e., the D2E7 VH CDR1). The framework regions for VL preferably are from the $V_{\kappa}I$ human germline family, more preferably from the A20 human germline Vk gene and most preferably from the D2E7 VL framework sequences shown in FIGS. 1A and 1B of U.S. Pat. No. 6,090,382. The framework regions for VH preferably are from the $V_{H}3$ human germline family, more preferably from the DP-31 human germline VH gene and most preferably from the D2E7 VH framework sequences shown in FIGS. 2A and 2B of U.S. Pat. No. 6,090,382.

Accordingly, in another embodiment, the antibody or antigen-binding portion thereof preferably contains a light chain variable region (LCVR) comprising the amino acid sequence of SEQ ID NO: 1 (i.e., the D2E7 VL) and a heavy chain variable region (HCVR) comprising the amino acid sequence of SEQ ID NO: 2 (i.e., the D2E7 VH). In certain embodiments, the antibody comprises a heavy chain constant region, such as an IgG1, IgG2, IgG3, IgG4, IgA, IgE, IgM or IgD constant region. Preferably, the heavy chain constant region is an IgG1 heavy chain constant region or an IgG4 heavy chain constant region. Furthermore, the antibody can comprise a light chain constant region, either a kappa light chain constant region or a lambda light chain constant region. Preferably, the antibody comprises a kappa light chain constant region. Alternatively, the antibody portion can be, for example, a Fab fragment or a single chain Fv fragment.

In still other embodiments, the invention includes uses of an isolated human antibody, or an antigen-binding portions thereof, containing D2E7-related VL and VH CDR3 domains. For example, antibodies, or antigen-binding portions thereof, with a light chain variable region (LCVR) having a CDR3 domain comprising an amino acid sequence selected from the group consisting of SEQ ID NO: 3, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25 and SEQ ID NO: 26 or with a heavy chain variable region (HCVR) having a CDR3 domain comprising an amino acid sequence selected from the group consisting of SEQ ID NO: 4, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34 and SEQ ID NO: 35.

The TNFα antibody used in the methods and compositions of the invention may be modified for improved treatment of ankylosing spondylitis. In some embodiments, the TNFα antibody or antigen binding fragments thereof, is chemically modified to provide a desired effect. For example, pegylation of antibodies and antibody fragments of the invention may be carried out by any of the pegylation reactions known in the art, as described, for example, in the following references: *Focus on Growth Factors* 3:4-10 (1992); EP 0 154 316; and EP 0 401 384 (each of which is incorporated by reference herein in its entirety). Preferably, the pegylation is carried out via an acylation reaction or an alkylation reaction with a reactive polyethylene glycol molecule (or an analogous reactive water-soluble polymer). A preferred water-soluble polymer for pegylation of the antibodies and antibody fragments of the invention is polyethylene glycol (PEG). As used herein, "polyethylene glycol" is meant to encompass any of the forms of PEG that have been used to derivatize other proteins, such as mono (C1—C10) alkoxy- or aryloxy-polyethylene glycol.

Methods for preparing pegylated antibodies and antibody fragments of the invention will generally comprise the steps of (a) reacting the antibody or antibody fragment with polyethylene glycol, such as a reactive ester or aldehyde derivative of PEG, under conditions whereby the antibody or antibody fragment becomes attached to one or more PEG groups, and (b) obtaining the reaction products. It will be apparent to one of ordinary skill in the art to select the optimal reaction conditions or the acylation reactions based on known parameters and the desired result.

Pegylated antibodies and antibody fragments may generally be used to treat ankylosing spondylitis by administration of the TNFα antibodies and antibody fragments described herein. Generally the pegylated antibodies and antibody fragments have increased half-life, as compared to the nonpegylated antibodies and antibody fragments. The pegylated antibodies and antibody fragments may be employed alone, together, or in combination with other pharmaceutical compositions.

In yet another embodiment of the invention, TNFα antibodies or fragments thereof can be altered wherein the constant region of the antibody is modified to reduce at least one constant region-mediated biological effector function relative to an unmodified antibody. To modify an antibody of the invention such that it exhibits reduced binding to the Fc receptor, the immunoglobulin constant region segment of the antibody can be mutated at particular regions necessary for Fc receptor (FcR) interactions (see e.g., Canfield, S. M. and S. L. Morrison (1991) *J. Exp. Med.* 173:1483-1491; and Lund, J. et al. (1991) *J. of Immunol.* 147:2657-2662). Reduction in FcR binding ability of the antibody may also reduce other effector functions which rely on FcR interactions, such as opsonization and phagocytosis and antigen-dependent cellular cytotoxicity.

An antibody or antibody portion used in the methods of the invention can be derivatized or linked to another functional molecule (e.g., another peptide or protein). Accordingly, the antibodies and antibody portions of the invention are intended to include derivatized and otherwise modified forms of the human anti-hTNFα antibodies described herein, including immunoadhesion molecules. For example, an antibody or antibody portion of the invention can be functionally linked (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate associate of the antibody or antibody portion with another molecule (such as a streptavidin core region or a polyhistidine tag).

One type of derivatized antibody is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which an antibody or antibody portion of the invention may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with biotin, and detected through indirect measurement of avidin or streptavidin binding.

An antibody, or antibody portion, used in the methods and compositions of the invention, can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and, preferably, secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Sambrook, Fritsch and Maniatis (eds), *Molecular Cloning; A Laboratory Manual, Second Edition*, Cold Spring Harbor, N.Y., (1989), Ausubel, F. M. et al. (eds.) *Current Protocols in Molecular Biology*, Greene Publishing Associates, (1989) and in U.S. Pat. No. 4,816,397 by Boss et al.

To express adalimumab (D2E7) or an adalimumab (D2E7)-related antibody, DNA fragments encoding the light and heavy chain variable regions are first obtained. These DNAs can be obtained by amplification and modification of germline light and heavy chain variable sequences using the polymerase chain reaction (PCR). Germline DNA sequences for human heavy and light chain variable region genes are known in the art (see e.g., the "Vbase" human germline sequence database; see also Kabat, E. A., et al. (1991) *Sequences of Proteins of Immunological Interest, Fifth Edition*, U.S. Department of Health and Human Services, NIH Publication No. 91-3242; Tomlinson, I. M., et al. (1992) "The Repertoire of Human Germline $V_H$ Sequences Reveals about Fifty Groups of $V_H$ Segments with Different Hypervariable Loops" *J. Mol. Biol.* 227:776-798; and Cox, J. P. L. et al. (1994) "A Directory of Human Germ-line $V_{78}$ Segments Reveals a Strong Bias in their Usage" *Eur. J. Immunol.* 24:827-836; the contents of each of which are expressly incorporated herein by reference). To obtain a DNA fragment encoding the heavy chain variable region of D2E7, or a D2E7-related antibody, a member of the $V_H3$ family of human germline VH genes is amplified by standard PCR. Most preferably, the DP-31 VH germline sequence is amplified. To obtain a DNA fragment encoding the light chain variable region of D2E7, or a D2E7-related antibody, a member of the $V_\kappa I$ family of human germline VL genes is amplified by standard PCR. Most preferably, the A20 VL germline sequence is amplified. PCR primers suitable for use in amplifying the DP-31 germline VH and A20 germline VL sequences can be designed based on the nucleotide sequences disclosed in the references cited supra, using standard methods.

Once the germline VH and VL fragments are obtained, these sequences can be mutated to encode the D2E7 or D2E7-related amino acid sequences disclosed herein. The amino acid sequences encoded by the germline VH and VL DNA sequences are first compared to the D2E7 or D2E7-related VH and VL amino acid sequences to identify amino acid residues in the D2E7 or D2E7-related sequence that differ from germline. Then, the appropriate nucleotides of the germline DNA sequences are mutated such that the mutated germline sequence encodes the D2E7 or D2E7-related amino acid sequence, using the genetic code to determine which nucleotide changes should be made. Mutagenesis of the germline sequences is carried out by standard methods, such as PCR-mediated mutagenesis (in which the mutated nucleotides are incorporated into the PCR primers such that the PCR product contains the mutations) or site-directed mutagenesis.

Moreover, it should be noted that if the "germline" sequences obtained by PCR amplification encode amino acid differences in the framework regions from the true germline configuration (i.e., differences in the amplified sequence as compared to the true germline sequence, for example as a result of somatic mutation), it may be desirable to change these amino acid differences back to the true germline sequences (i.e., "backmutation" of framework residues to the germline configuration).

Once DNA fragments encoding D2E7 or D2E7-related VH and VL segments are obtained (by amplification and mutagenesis of germline VH and VL genes, as described above), these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al. (1991) *Sequences of Proteins of Immunological Interest, Fifth Edition*, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) *Sequences of Proteins of Immunological Interest, Fifth Edition*, U.S. Department of Health and Human Services, NIH Publication No. 91-3242) and DNA fragments encompassing these regions can be obtained by standard PCR amplification. The light chain constant region can be a kappa or lambda constant region, but most preferably is a kappa constant region.

To create a scFv gene, the VH- and VL-encoding DNA fragments are operatively linked to another fragment encoding a flexible linker, e.g., encoding the amino acid sequence $(Gly_4-Ser)_3$, such that the VH and VL sequences can be expressed as a contiguous single-chain protein, with the VL and VH regions joined by the flexible linker (see e.g., Bird et al. (1988) *Science* 242:423-426; Huston et al. (1988) *Proc. Natl. Acad. Sci. USA* 85:5879-5883; McCafferty et al., *Nature* (1990) 348:552-554).

To express the antibodies, or antibody portions used in the invention, DNAs encoding partial or full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). Prior to insertion of the D2E7 or D2E7-related light or heavy chain sequences, the expression vector may already carry antibody constant region sequences. For example, one approach to converting the D2E7 or D2E7-related VH and VL sequences to full-length antibody genes is to insert them into expression vectors already encoding heavy chain constant and light chain constant regions, respectively, such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel; *Gene Expression Technology: Methods in Enzymology* 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see e.g., U.S. Pat. No. 5,168,062 by Stinski, U.S. Pat. No. 4,510,245 by Bell et al. and U.S. Pat. No. 4,968,615 by Schaffner et al.

In addition to the antibody chain genes and regulatory sequences, the recombinant expression vectors used in the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399, 216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr⁻ host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) *Immunology Today* 6:12-13).

Preferred mammalian host cells for expressing the recombinant antibodies of the invention include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce portions of intact antibodies, such as Fab fragments or scFv molecules. It is understood that variations on the above procedure are within the scope of the present invention. For example, it may be desirable to transfect a host cell with DNA encoding either the light chain or the heavy chain (but not both) of an antibody of this invention. Recombinant DNA technology may also be used to remove some or all of the DNA encoding either or both of the light and heavy chains that is not necessary for binding to hTNFα. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than hTNFα by crosslinking an antibody of the invention to a second antibody by standard chemical crosslinking methods.

In a preferred system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are culture to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium.

In view of the foregoing, nucleic acid, vector and host cell compositions that can be used for recombinant expression of the antibodies and antibody portions used in the invention include nucleic acids, and vectors comprising said nucleic acids, comprising the human TNFα antibody adalimumab (D2E7). The nucleotide sequence encoding the D2E7 light chain variable region is shown in SEQ ID NO: 36. The CDR1 domain of the LCVR encompasses nucleotides 70-102, the CDR2 domain encompasses nucleotides 148-168 and the CDR3 domain encompasses nucleotides 265-291. The nucleotide sequence encoding the D2E7 heavy chain variable region is shown in SEQ ID NO: 37. The CDR1 domain of the HCVR encompasses nucleotides 91-105, the CDR2 domain encompasses nucleotides 148-198 and the CDR3 domain encompasses nucleotides 295-330. It will be appreciated by the skilled artisan that nucleotide sequences encoding D2E7-related antibodies, or portions thereof (e.g., a CDR domain, such as a CDR3 domain), can be derived from the nucleotide sequences encoding the D2E7 LCVR and HCVR using the genetic code and standard molecular biology techniques.

Recombinant human antibodies of the invention in addition to D2E7 or an antigen binding portion thereof, or D2E7-related antibodies disclosed herein can be isolated by screening of a recombinant combinatorial antibody library, preferably a scFv phage display library, prepared using human VL and VH cDNAs prepared from mRNA derived from human lymphocytes. Methodologies for preparing and screening such libraries are known in the art. In addition to commercially available kits for generating phage display libraries (e.g., the Pharmacia *Recombinant Phage Antibody System*, catalog no. 27-9400-01; and the Stratagene SurfZAP™ phage display kit, catalog no. 240612), examples of methods and reagents particularly amenable for use in generating and screening antibody display libraries can be found in, for example, Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) *Bio/Technology* 9:1370-1372; Hay et al. (1992) *Hum Antibod Hybridomas* 3:81-65; Huse et al. (1989) *Science* 246:1275-1281; McCafferty et al., *Nature* (1990) 348:552-554; Griffiths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrard et al. (1991) *Bio/Technology* 9:1373-1377; Hoogenboom et al. (1991) *Nuc Acid Res* 19:4133-4137; and Barbas et al. (1991) *PNAS* 88:7978-7982.

In a preferred embodiment, to isolate human antibodies with high affinity and a low off rate constant for hTNFα, a murine anti-hTNFα antibody having high affinity and a low off rate constant for hTNFα (e.g., MAK 195, the hybridoma for which has deposit number ECACC 87 050801) is first used to select human heavy and light chain sequences having similar binding activity toward hTNFα, using the epitope imprinting methods described in Hoogenboom et al., PCT Publication No. WO 93/06213. The antibody libraries used in this method are preferably scFv libraries prepared and screened as described in McCafferty et al., PCT Publication No. WO 92/01047, McCafferty et al., *Nature* (1990) 348:552-554; and Griffiths et al., (1993) *EMBO J.* 12:725-734. The scFv antibody libraries preferably are screened using recombinant human TNFα as the antigen.

Once initial human VL and VH segments are selected, "mix and match" experiments, in which different pairs of the initially selected VL and VH segments are screened for hTNFα binding, are performed to select preferred VL/VH pair combinations. Additionally, to further improve the affinity and/or lower the off rate constant for hTNFα binding, the VL and VH segments of the preferred VL/VH pair(s) can be randomly mutated, preferably within the CDR3 region of VH and/or VL, in a process analogous to the in vivo somatic mutation process responsible for affinity maturation of antibodies during a natural immune response. This in vitro affinity maturation can be accomplished by amplifying VH and VL regions using PCR primers complimentary to the VH CDR3 or VL CDR3, respectively, which primers have been "spiked" with a random mixture of the four nucleotide bases at certain positions such that the resultant PCR products encode VH and VL segments into which random mutations have been introduced into the VH and/or VL CDR3 regions. These randomly mutated VH and VL segments can be rescreened for binding to hTNFα and sequences that exhibit high affinity and a low off rate for hTNFα binding can be selected.

Following screening and isolation of an anti-hTNFα antibody of the invention from a recombinant immunoglobulin display library, nucleic acid encoding the selected antibody can be recovered from the display package (e.g., from the phage genome) and subcloned into other expression vectors by standard recombinant DNA techniques. If desired, the nucleic acid can be further manipulated to create other antibody forms of the invention (e.g., linked to nucleic acid encoding additional immunoglobulin domains, such as additional constant regions). To express a recombinant human antibody isolated by screening of a combinatorial library, the DNA encoding the antibody is cloned into a recombinant expression vector and introduced into a mammalian host cells, as described in further detail in above.

Methods of isolating human neutralizing antibodies with high affinity and a low off rate constant for hTNFα are described in U.S. Pat. Nos. 6,090,382, 6,258,562, and 6,509,015, each of which is incorporated by reference herein.

Antibodies, antibody-portions, and other TNFα inhibitors for use in the methods of the invention, can be incorporated into pharmaceutical compositions suitable for administration to a subject. Typically, the pharmaceutical composition comprises an antibody, antibody portion, or other TNFα inhibitor, and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it is preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody, antibody portion, or other TNFα inhibitor.

The compositions for use in the methods and compositions of the invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies or other TNFα inhibitors. The preferred mode of administration is parenteral (e.g., intravenous, subcutaneous, intraperitoneal, intramuscular). In a preferred embodiment, the antibody or other TNFα inhibitor is administered by intravenous infusion or injection. In another preferred embodiment, the antibody or other TNFα inhibitor is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody, antibody portion, or other TNFα inhibitor) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In one embodiment, the invention includes pharmaceutical compositions comprising an effective TNFα inhibitor and a pharmaceutically acceptable carrier, wherein the effective TNFα inhibitor may be used to treat ankylosing spondylitis.

In one embodiment, the antibody or antibody portion for use in the methods of the invention is incorporated into a pharmaceutical formulation as described in PCT/IB03/04502 and U.S. Appln. No. 20040033228, incorporated by reference herein. This formulation includes a concentration 50 mg/ml of the antibody D2E7 (adalimumab), wherein one pre-filled syringe contains 40 mg of antibody for subcutaneous injection.

The antibodies, antibody-portions, and other TNFα inhibitors of the present invention can be administered by a variety of methods known in the art, although for many therapeutic applications, the preferred route/mode of administration is parenteral, e.g., subcutaneous injection. In another embodiment, administration is via intravenous injection or infusion.

As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, Robinson, ed., Dekker, Inc., New York, 1978.

In one embodiment, the TNFα antibodies and inhibitors used in the invention are delivered to a subject subcutaneously. In one embodiment, the subject administers the TNFα inhibitor, including, but not limited to, TNFα antibody, or antigen-binding portion thereof, to himself/herself.

The TNFα antibodies and inhibitors used in the invention may also be administered in the form of protein crystal formulations which include a combination of protein crystals encapsulated within a polymeric carrier to form coated particles. The coated particles of the protein crystal formulation may have a spherical morphology and be microspheres of up to 500 micro meters in diameter or they may have some other morphology and be microparticulates. The enhanced concentration of protein crystals allows the antibody of the invention to be delivered subcutaneously. In one embodiment, the TNFα antibodies of the invention are delivered via a protein delivery system, wherein one or more of a protein crystal formulation or composition, is administered to a subject with a TNFα-related disorder. Compositions and methods of preparing stabilized formulations of whole antibody crystals or antibody fragment crystals are also described in WO 02/072636, which is incorporated by reference herein. In one embodiment, a formulation comprising the crystallized antibody fragments described in PCT/IB03/04502 and U.S. Appln. No. 20040033228, incorporated by reference herein, are used to treat ankylosing spondylitis using the treatment methods of the invention.

In certain embodiments, an antibody, antibody portion, or other TNFα inhibitor of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Supplementary active compounds can also be incorporated into the compositions. In certain embodiments, an antibody or antibody portion for use in the methods of the invention is coformulated with and/or coadministered with one or more additional therapeutic agents, including an ankylosing spondylitis inhibitor or antagonist. For example, an anti-hTNFα antibody or antibody portion of the invention may be coformulated and/or coadministered with one or more additional antibodies that bind other targets associated with TNFα related disorders (e.g., antibodies that bind other cytokines or that bind cell surface molecules), one or more cytokines, soluble TNFα receptor (see e.g., PCT Publication No. WO 94/06476) and/or one or more chemical agents that inhibit hTNFα production or activity (such as cyclohexane-ylidene derivatives as described in PCT Publication No. WO 93/19751) or any combination thereof. Furthermore, one or more antibodies of the invention may be used in combination with two or more of the foregoing therapeutic agents. Such combination therapies may advantageously utilize lower dosages of the administered therapeutic agents, thus avoiding possible side effects, complications or low level of response by the patient associated with the various monotherapies.

The pharmaceutical compositions of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody, antibody portion, or other TNFα inhibitor may vary according to factors such as the disease state, age, sex, and weight of the individual, and the ability of the antibody, antibody portion, other TNFα inhibitor to elicit a desired response in the individual. A therapeutically effective amount is also one in which any toxic or detrimental effects of the antibody, antibody portion, or other TNFα inhibitor are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Additional description regarding methods and uses of the invention comprising administration of a TNFα inhibitor are described in Part III of this specification, as well as the below examples.

The invention also pertains to packaged pharmaceutical compositions or kits for administering the anti-TNF antibodies of the invention for the treatment of ankylosing spondylitis. In one embodiment of the invention, the kit comprises a TNFα inhibitor, such as an antibody and instructions for administration of the TNFα inhibitor for treatment of ankylosing spondylitis. The instructions may describe how, e.g., subcutaneously, and when, e.g., at week 0, week 2, week 4, etc., the different doses of TNFα inhibitor shall be administered to a subject for treatment.

Another aspect of the invention pertains to kits containing a pharmaceutical composition comprising a TNFα inhibitor, such as an antibody, and a pharmaceutically acceptable carrier and one or more pharmaceutical compositions each comprising an additional therapeutic agent useful for treating ankylosing spondylitis, and a pharmaceutically acceptable carrier. Alternatively, the kit comprises a single pharmaceutical composition comprising an anti-TNFα antibody, one or more drugs useful for treating ankylosing spondylitis, and a pharmaceutically acceptable carrier. The instructions may describe how, e.g., subcutaneously, and when, e.g., at week 0, week 2, week 4, etc., the different doses of TNFα inhibitor and/or the additional therapeutic agent shall be administered to a subject for treatment.

The kit may contain instructions for dosing of the pharmaceutical compositions for the treatment of ankylosing spondylitis. Additional description regarding articles of manufacture of the invention are described in subsection III.

The package or kit alternatively can contain the TNFα inhibitor and it can be promoted for use, either within the package or through accompanying information, for the uses or treatment of the disorders described herein. The packaged pharmaceuticals or kits further can include a second agent (as described herein) packaged with or copromoted with instructions for using the second agent with a first agent (as described herein).

IIII. Uses and Compositions for Treating Ankylosing Spondylitis

Ankylosing spondylitis (AS) is a chronic rheumatic disease. The sacroiliac joints are affected and, to a varying degree, the spinal column. The disease may also involve the peripheral joints and extra-articular structures. Patients commonly experience pain, morning stiffness and disability, all which generally increase with duration of disease. Systemic features, such as anorexia and fatigue may also occur. In late disease, some patients develop acute anterior uveitis, cardiovascular or pulmonary problems. Men are more commonly affected than women, and, as with other sponylarthritides, AS is associated with positivity for the HLA-B27 gene.

In one embodiment, the invention provides a method for treating ankylosing spondylitis in a subject. The invention also provides a method for achieving partial remission of a subject having AS by administering a TNFα inhibitor.

In one embodiment, treatment of AS is achieved by administering a TNFα inhibitor to a subject in accordance with a biweekly dosing regimen. Biweekly dosing regimens can be used to treat disorders in which TNFα activity is detrimental, and are further described in U.S. application Ser. No. 10/163, 657 (US 20030235585), incorporated by reference herein. The TNFα inhibitor, including a TNFα antibody, or an antigen-binding portion thereof, may be administered to the subject on a biweekly dosing regimen for treatment of AS. In one embodiment, biweekly dosing includes a dosing regimen wherein doses of a TNFα inhibitor are administered to a subject every other week beginning at week 0. In one embodiment, biweekly dosing includes a dosing regimen where doses of a TNFα inhibitor are administered to a subject every other week consecutively for a given time period, e.g., 4 weeks, 8 weeks, 16, weeks, 24 weeks, etc. Biweekly dosing is preferably administered parenterally, including subcutaneously.

In one embodiment, the human TNFα antibody, or an antigen-binding portion thereof, is administered in a dose of about 40 mg. In one embodiment, the human TNFα antibody, or an antigen-binding portion thereof, is adalimumab.

The invention provides a method of decreasing pain and fatigue in a subject having AS comprising administering a human TNFα antibody, or antigen-binding portion thereof, to the subject such that pain and fatigue are decreased. The invention also includes use of a human TNFα antibody, or antigen-binding portion thereof, in the manufacture of a medicament for the treatment of pain and fatigue in a subject having AS.

The invention also provides methods for improving AS in a subject based on indices used to measure the disease state. In one embodiment, the invention provides a method for decreasing the decrease in fatigue is determined by a decrease of at least about 1.9 in a BASDAI score of the subject. In one embodiment, the decrease in fatigue is determined by a decrease of at least about 2.0 in a BASDAI score of the subject. Alternatively, improvements in fatigue in a subject having AS may be determined using the FACIT-F score, e.g., a meach change in FACIT score of about 7-8 following treatment of the subject with a TNFα inhibitor.

The invention also includes a method of inducing partial remission of AS in a subject comprising administering a human TNFα antibody, or antigen-binding portion thereof, to the subject, such that partial remission of AS is induced. The invention provides a use of a human TNFα antibody, or antigen-binding portion thereof, in the manufacture of a medicament for inducing partial remission of AS in a subject. In one embodiment, the subject has a value of less than 20 on a scale of 0-100 in all four ASAS domains.

The invention provides uses and methods for treating certain subpopulations of AS patients with a TNFα inhibitor. Also included in the invention are methods for determining whether a TNFα inhibitor, e.g., a TNFα antibody, or antigen-binding portion thereof, is effective for treating a certain subpopulation of AS patients. Thus, the invention also includes a method of treating a subject who is a member of a subpopulation of AS patients with a TNFα inhibitor which has been identified as being an effective TNFα inhibitor for the treatment of the given subpopulation. In one embodiment, the methods of treatment described herein may be used to treat AS subjects who have failed prior therapy with conventional drugs used to treat AS. Examples of such conventional therapy include DMARD therapy and NSAIDs therapy. Failure on a prior therapy can be measured using any of the indices described herein, e.g., failure to achieve an ASAS20 response.

In one embodiment, treatment of AS is achieved by administering a human TNFα antibody, or an antigen-binding portion thereof, to a subject having AS, wherein the human TNFα antibody, or an antigen-binding portion thereof, is administered on a biweekly dosing regimen.

Methods of treatment described herein may include administration of a TNFα inhibitor to a subject to achieve a therapeutic goal, e.g., improvement in ASAS domains, induction of partial remission, ASAS20, ASAS40, ASAS50, ASAS70 response, ASAS5/6 response, improvement in BASDAI score, BASDAI20 response, BASDAI50 response, BASDAI 70 response Also included in the scope of the invention are uses of a TNFα inhibitor in the manufacture of a medicament to achieve a therapeutic goal, e.g., improvement in ASAS domains, induction of partial remission, ASAS20, ASAS40, ASAS50, ASAS70 response, ASAS5/6 response, improvement in BASDAI score, BASDAI20 response, BASDAI50 response, BASDAI 70 response. Thus, where methods are described herein, it is also intended to be part of this invention that the use of the TNFα inhibitor in the manufacture of a medicament for the purpose of the method is also considered within the scope of the invention. Likewise, where a use of a TNFα inhibitor in the manufacture of a medicament for the purpose of achieving a therapeutic goal is described, methods of treatment resulting in the therapeutic goal are also intended to be part of the invention.

In one embodiment, the invention provides a method of treating AS in a subject comprising administering a human TNFα antibody, or antigen-binding portion thereof, e.g., adalimumab, to the subject at week 0 on a biweekly dosing regimen. In one embodiment, the human TNFα antibody, or antigen-binding portion thereof, is administered subcutaneously. In one embodiment, AS is treated by administering a human TNFα antibody, or antigen-binding portion thereof, on biweekly dosing regimen for a minimum time period, e.g., at least about 12 weeks, at least about 20, or at least about 24.

Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

Dosage regimens described herein may be adjusted to provide the optimum desired response, e.g., attaining partial remission of AS, in consideration of the teachings herein. It is to be noted that dosage values may vary with the type and severity of AS. It is to be further understood that for any particular subject, specific dosage regimens may be adjusted over time according to the teachings of the specification and the individual need and the professional judgment of the person administering or supervising the administration of the compositions, and that dosage amounts and ranges set forth herein are exemplary only and are not intended to limit the scope or practice of the claimed invention.

Articles of Manufacture

The invention also provides a packaged pharmaceutical composition wherein the TNFα inhibitor, e.g., TNFα antibody, is packaged within a kit or an article of manufacture. The kit or article of manufacture of the invention contains materials useful for the treatment, including induction and/or remission, prevention and/or diagnosis of AS. The kit or article of manufacture comprises a container and a label or package insert or printed material on or associated with the container which provides information regarding use of the TNFα inhibitor, e.g., a TNFα antibody, for the treatment of AS.

A kit or an article of manufacture refers to a packaged product comprising components with which to administer a TNFα inhibitor for treatment of AS. The kit preferably comprises a box or container that holds the components of the kit. The box or container is affixed with a label or a Food and Drug Administration approved label, including a protocol for administering the TNFα inhibitor. The box or container holds components of the invention which are preferably contained within plastic, polyethylene, polypropylene, ethylene, or propylene vessels. The vessels can be capped-tubes or bottles. The kit can also include instructions for administering the TNFα antibody of the invention. In one embodiment the kit of the invention includes the formulation comprising the human antibody adalimumab (or D2E7), as described in PCT/IB03/04502 and U.S. application Ser. No. 10/222,140, incorporated by reference herein.

The term "package insert" is used to refer to instructions customarily included in commercial packages of therapeutic products, that contain information about the indications, usage, dosage, administration, contraindications and/or warnings concerning the use of such therapeutic products.

Suitable containers for the TNFα inhibitor, e.g., a TNFα antibody, include, for example, bottles, vials, syringes, pens, etc. The containers may be formed from a variety of materials such as glass or plastic. The container holds a composition which is by itself or when combined with another composition effective for treating, preventing and/or diagnosing the condition and may have a sterile access port.

In one embodiment, the article of manufacture comprises a TNFα inhibitor, e.g., a TNFα antibody, and a label which indicates to a subject who will be administering the TNFα inhibitor about using the TNFα inhibitor for the treatment of AS. The label may be anywhere within or on the article of manufacture. In one embodiment, the article of manufacture comprises a container, such as a box, which comprises the TNFα inhibitor and a package insert or label providing information pertaining to use of the TNFα inhibitor for the treatment of AS. In another embodiment, the information is printed on a label which is on the outside of the article of manufacture, in a position which is visible to prospective purchasers.

In one embodiment, the package insert of the invention informs a reader, including a subject, e.g., a purchaser, who will be administering the TNFα inhibitor for treatment, that the TNFα inhibitor, e.g., a TNFα antibody such as adalimumab, is an indicated treatment of AS, including of moderately to severely active disease in adult patients.

In one embodiment, the article of manufacture of the invention comprises a human TNFα antibody, or antigen-binding portion thereof, and a package insert comprising instructions for administering the human TNFα antibody, or antigen-binding portion thereof, to a human subject for the treatment of adults with moderate to severe active ankylosing spondylitis who have had an inadequate response to conventional therapy.

The package insert may describe certain patient populations who may respond favorably to the TNFα inhibitor within the article of manufacture. For example, the package insert may indicate that the TNFα antibody, e.g., adalimumab, may be used to treat AS in patients who have had an inadequate response to conventional therapy, e.g., DMARD or NSAID therapy. In one embodiment, the invention provides an article of manufacture comprising a human TNFα antibody, or antigen-binding portion thereof, and a package insert which indicates that the human TNFα antibody, or antigen-binding portion thereof, is indicated for the treatment of adults with moderate to severe active ankylosing spondylitis who have had an inadequate response to conventional therapy.

In one embodiment, the package insert of the invention describes certain therapeutic benefits of the TNFα antibody, e.g., adalimumab, including specific symptoms of AS which may be reduced by using the TNFα antibody, e.g., adalimumab. It should be noted that the package insert may also contain information pertaining to other disorders which are treatable using the TNFα antibody, e.g., adalimumab.

In another embodiment, the package insert of the invention describes the dose and administration of adalimumab, for the treatment of AS. The label may indicate that the recommended dose for the treatment of AS with adalimumab is 40 mg administered every other week. In one embodiment, the package insert of the invention indicates that adalimumab is administered by subcutaneous injection.

The package insert of the invention may also provide information to subjects who will be receiving adalimumab regarding combination uses for both safety and efficacy purposes. The package insert of the invention may contain warnings and precautions regarding the use of the TNFα inhibitor, e.g., a TNFα antibody such as adalimumab.

The label of the invention may further contain information regarding the use of the TNFα inhibitor, e.g., a TNFα antibody such as adalimumab, in clinical studies for AS. In one embodiment, the label of the invention describes the studies described herein as the Examples, either as a whole or in portion.

In one embodiment of the invention, the kit comprises a TNFα inhibitor, such as an antibody, an second pharmaceutical composition comprising an additional therapeutic agent, and instructions for administration of both agents for the treatment of AS. The instructions may describe how, e.g., subcutaneously, and when, e.g., at week 0, week 2, and biweekly thereafter, doses of TNFα antibody and/or the additional therapeutic agent shall be administered to a subject for treatment.

Another aspect of the invention pertains to kits containing a pharmaceutical composition comprising an anti-TNFα antibody and a pharmaceutically acceptable carrier and one or more additional pharmaceutical compositions each comprising a drug useful for treating a TNFα related disorder and a pharmaceutically acceptable carrier. Alternatively, the kit comprises a single pharmaceutical composition comprising an anti-TNFα antibody, one or more drugs useful for treating a TNFα related disorder and a pharmaceutically acceptable carrier. The kits further contain instructions for dosing of the pharmaceutical compositions for the treatment of a TNFα related disorder.

The package or kit alternatively may contain the TNFα inhibitor and it may be promoted for use, either within the package or through accompanying information, for the uses or treatment of the disorders described herein. The packaged pharmaceuticals or kits further can include a second agent (as described herein) packaged with or copromoted with instructions for using the second agent with a first agent (as described herein).

Additional Therapeutic Agents

Methods, uses, and compositions of the invention also include combinations of TNFα inhibitors, including antibodies, and other therapeutic agents. TNFα inhibitors, including antibodies, or antigen binding portions thereof, can be used alone or in combination with additional agents to treat AS. It should be understood that antibodies, or antigen binding portion thereof, can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the antibody of the present invention. The additional agent also can be an agent that imparts a beneficial attribute to the therapeutic composition e.g., an agent which affects the viscosity of the composition.

It should further be understood that the combinations which are to be included within this invention are those combinations useful for their intended purpose. The agents set forth below are illustrative for purposes and not intended to be limited. The combinations, which are part of this invention, can be the antibodies of the present invention and at least one additional agent selected from the lists below. The combination can also include more than one additional agent, e.g., two or three additional agents if the combination is such that the formed composition can perform its intended function.

TNFα inhibitors described herein may be used in combination with additional therapeutic agents such as a Disease Modifying Anti-Rheumatic Drug (DMARD) or a Nonsteroidal Antiinflammatory Drug (NSAID) or a steroid or any combination thereof. Preferred examples of a DMARD are hydroxychloroquine, leflunomide, methotrexate, parenteral gold, oral gold and sulfasalazine. Preferred examples of non-steroidal anti-inflammatory drug(s) also referred to as NSAIDS include drugs like ibuprofen. Other preferred combinations are corticosteroids including prednisolone; the well known side effects of steroid use can be reduced or even eliminated by tapering the steroid dose required when treating patients in combination with the anti-TNFα antibodies of this invention. Non-limiting examples of therapeutic agents for rheumatoid arthritis with which an antibody, or antibody portion, of the invention can be combined include the following: cytokine suppressive anti-inflammatory drug(s) (CSAIDs); antibodies to or antagonists of other human cytokines or growth factors, for example, TNF, LT, IL-1, IL-2, IL-3, IL-4, IL-5, IL-6, IL-7, IL-8, IL-15, IL-16, IL-18, IL-21, IL-23, interferons, EMAP-II, GM-CSF, FGF, and PDGF. Antibodies of the invention, or antigen binding portions thereof, can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L).

Preferred combinations of therapeutic agents may interfere at different points in the autoimmune and subsequent inflammatory cascade; preferred examples include TNF antagonists/inhibitors such as soluble p55 or p75 TNF receptors, derivatives, thereof, (p75TNFR1gG (Enbrel™) or p55TNFR1gG (Lenercept), chimeric, humanized or human TNF antibodies, or a fragment thereof, including infliximab (Remicade®, Johnson and Johnson; described in U.S. Pat. No. 5,656,272, incorporated by reference herein), CDP571 (a humanized monoclonal anti-TNF-alpha IgG4 antibody), CDP 870 (a humanized monoclonal anti-TNF-alpha antibody fragment), an anti-TNF dAb (Peptech), CNTO 148 (golimumab; Medarex and Centocor, see WO 02/12502), and adalimumab (Humira® Abbott Laboratories, a human anti-TNF mAb, described in U.S. Pat. No. 6,090,382 as D2E7). Additional TNF antibodies which can be used in the invention are described in U.S. Pat. Nos. 6,593,458; 6,498,237; 6,451,983; and 6,448,380, each of which is incorporated by reference herein. Other combinations including TNFα converting enzyme (TACE) inhibitors; IL-1 inhibitors (Interleukin-1-converting enzyme inhibitors, IL-1RA etc.) may be effective for the same reason. Other combinations include the IL-6 antibody tocilizumab (Actemra). Other preferred combinations include Interleukin 11. Yet another preferred combination are other key players of the autoimmune response which may act parallel to, dependent on or in concert with TNFα function; especially preferred are IL-18 antagonists including IL-18 antibodies or soluble IL-18 receptors, or IL-18 binding proteins. It has been shown that TNFα and IL-18 have overlapping but distinct functions and a combination of antagonists to both may be most effective. Yet another preferred combination are non-depleting anti-CD4 inhibitors. Yet other preferred combinations include antagonists of the co-stimulatory pathway CD80 (B7.1) or CD86 (B7.2) including antibodies, soluble receptors or antagonistic ligands.

The TNFα inhibitors, including antibodies, or antigen binding portions thereof, used in the invention may also be combined with agents, such as methotrexate, 6-MP, azathioprine sulphasalazine, mesalazine, olsalazine chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signaling by proinflammatory cytokines such as TNFα or IL-1 (e.g. IRAK, NIK, IKK, p38 or MAP kinase inhibitors), IL-1β converting enzyme inhibitors, TNFα converting enzyme (TACE) inhibitors, T-cell signalling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors and the derivatives p75TNFRIgG (Enbrel™ and p55TNFRIgG (Lenercept)), sIL-1R1, sIL-1R11, sIL-6R), antiinflammatory cytokines (e.g. IL-4, IL-10, IL-11, IL-13 and TGFβ), tocilizumab (Actemra), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone hcl, hydrocodone bitartrate/apap, diclofenac sodium/misoprostol, fentanyl, anakinra, human recombinant, tramadol hcl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline hcl, sulfadiazine, oxycodone hcl/acetaminophen, olopatadine hcl, misoprostol, naproxen sodium, omeprazole, cyclophosphamide, rituximab, IL-1 TRAP, MRA, CTLA4-IG, IL-18 BP, anti-IL-18, Anti-IL15, BIRB-796, SCIO-469, VX-702, AMG-548, VX-740, Roflumilast, IC-485, CDC-801, and Mesopram. Preferred combinations include methotrexate or leflunomide and in moderate or severe AS cases, cyclosporine.

Non-limiting examples of therapeutic agents for AS with which TNFα inhibitor, such as an antibody, or antibody portion, can be combined include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, efalizumab.

Non-limiting examples of therapeutic agents for Ankylosing Spondylitis with which an antibody, or antibody portion, of the invention can be combined include the following: ibuprofen, diclofenac and misoprostol, naproxen, meloxicam, indomethacin, diclofenac, celecoxib, rofecoxib, Sulfasalazine, Methotrexate, azathioprine, minocyclin, prednisone, etanercept, infliximab. In one embodiment, the methods of the invention include the combination of a TNFα inhibitor and methotrexate.

IV. Efficacy of TNFα Inhibitor

The invention also provides methods for determining whether a TNFα inhibitor is effective at treating AS in a subject. Such methods may be used to determine the efficacy of a TNFα inhibitor, including those which are unknown or unconfirmed to have such efficacy. Using the methods described herein, effective TNFα inhibitors may be determined or confirmed, and, subsequently, used in the method of treating AS.

Methods of determining efficacy of a TNFα inhibitor for treating ankylosing spondylitis (AS) in a subject include any means known in the art. The clinical course of AS is measured by using any number of instruments to evaluate various AS symptoms. Some of the commonly used scales include the Assessment in Ankylosing Spondylitis (ASAS), the Bath Ankylosing Spondylitis Disease Activity Index (BASDAI) (Garrett et al. (1994) *J Rheumatol* 21:2286), the Bath Ankylosing Spondylitis Metrology Index (BASMI) (Jenkinson et al. (1994) *J Rheumatol* 21:1694), and the Bath Ankylosing Spondylitis Functional Index (BASFI) (Calin et al. (1994) *J Rheumatol* 21:2281). These indices can be used to monitor a patient over time and to determine improvement. Each of these scales is described further below, as well as in the examples:

Criteria for Measuring the Clinical Course of AS

1. The Assessment in Ankylosing Spondylitis (ASAS20) is the primary endpoint in the pivotal Phase 3 AS studies. A ≥20% improvement and absolute improvement of ≥10 units (scale of 0-100) in ≥3 of 4 domains: Subject Global Assessment, Pain, Function, and Inflammation. There must be an absence of deterioration in the potential remaining domain (deterioration is defined as a change for the worse of ≥20% and a net worsening of ≥10 units (scale of 0-100).

2. The Bath Ankylosing Spondylitis Disease Activity Index (BASDAI) can be used to evaluate the level of disease activity in a patient with AS. BASDAI focuses upon signs and symptoms of the inflammatory aspects of AS, nocturnal and total back pain, the patient's global assessment and actual physical measurements of spinal mobility such as the Schober's test, chest expansion score and occiput to wall measurement. BASDAI measures disease activity on the basis of six questions relating to fatigue, spinal pain, peripheral arthritis, enthesitis (inflammation at the points where tendons/ligaments/joint capsule enter the bone), and morning stiffness. These questions are answered on a 10-cm horizontal visual analog scale measuring severity of fatigue, spinal and peripheral joint pain, localized tenderness, and morning stiffness (both qualitative and quantitative). The final BASDAI score has a range of 0 to 10.

3. The Bath Ankylosing Spondylitis Functional Index (BASFI) measures the physical function impairment caused by AS, and is a self-assessment instrument that consists of 8 specific questions regarding function in AS, and 2 questions reflecting the patient's ability to cope with everyday life. Each question is answered on a 10-cm horizontal visual analog scale, the mean of which gives the BASFI score (0-10).

4. The Bath Ankylosing Spondylitis Metrology Index (BASMI) consists of 5 simple clinical measurements that provide a composite index and define disease status in AS. Analysis of metrology (20 measurements) identified these 5 measurements as most accurately reflecting axial status: cervical rotation, tragus to wall distance, lateral flexion, modified Schober's test, and intermalleolar distance. The BASMI is quick (7 minutes), reproducible, and sensitive to change across the entire spectrum of disease. The BASMI index comprises 5 measures of hip and spinal mobility in AS. The five BASMI measures, scaled 0 (mild) to 10 (severe), include tragus to wall distance, cervical rotation, lumbar flexion, lumbar side flexion, and intermolleolar distance.

Combinations of the above-mentioned criteria may also used to evaluate patients. In addition, other indices such as FACIT-F or the ability of the TNFα inhibitor to induce partial remission can be used to determine disease activity in AS patients.

The invention provides methods for determining whether a TNFα inhibitor is effective at treating AS in a subject. Such methods may be used to determine the efficacy of a TNFα inhibitor, including those which are unknown or unconfirmed to have such efficacy. Using the methods described herein, effective TNFα inhibitors may be determined or confirmed, and, subsequently, used in the method of treating AS.

In one embodiment, the invention provides a method for determining efficacy using a Bath Ankylosing Spondylitis Disease Activity Index (BASDAI) 20 response. The invention includes a method of determining the efficacy of a TNFα inhibitor for treating ankylosing spondylitis (AS) in a subject comprising determining a Bath Ankylosing Spondylitis Disease Activity Index (BASDAI) 20 response of a patient population having AS and who was administered the TNFα inhibitor, wherein an BASDAI 20 response in at least about 60% of the patient population indicates that the TNFα inhibitor is an effective TNFα inhibitor for the treatment of AS in a subject.

The invention further provides a method of treating AS in a subject comprising administering an effective TNFα inhibitor to the subject such that AS is treated, wherein the effective TNFα inhibitor was previously identified as resulting in a BASDAI 20 response in at least about 60% of a patient population having AS and who was administered the TNFα inhibitor. In one embodiment, the effective TNFα inhibitor was previously identified as resulting in a BASDAI 20 response in at least about 65% of a patient population having AS and who was administered the TNFα inhibitor. In one embodiment, the effective TNFα inhibitor was previously identified as resulting in a BASDAI 20 response in at least about 70% of a patient population having AS and who was administered the TNFα inhibitor. In one embodiment, the effective TNFα inhibitor was previously identified as resulting in a BASDAI 20 response in at least about 75% of a patient population having AS and who was administered the TNFα inhibitor. In one embodiment, the effective TNFα inhibitor was previously identified as resulting in a BASDAI 20 response in at least about 80% of a patient population having AS and who was administered the TNFα inhibitor. In one embodiment, the effective TNFα inhibitor was previously identified as resulting in a BASDAI 20 response in at least about 85% of a patient population having AS and who was administered the TNFα inhibitor. In one embodiment, an BASDAI 20 response in at least about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, of the patient population indicates that the TNFα inhibitor is an effective TNF inhibitor for the treatment of AS in the subject.

The invention also includes a method of determining the efficacy of a TNFα inhibitor for treating ankylosing spondylitis (AS) in a subject comprising determining a Bath Ankylosing Spondylitis Disease Activity Index (BASDAI) 50 response of a patient population having AS and who was administered the TNFα inhibitor, wherein an BASDAI 50 response in at least about 65% of the patient population indicates that the TNFα inhibitor is an effective TNFα inhibitor for the treatment of AS in the subject. In one embodiment, an BASDAI 50 response in at least about 23%, at least about 30%, at least about 35%, at least about 40%, at least about 45%, at least about 50%, at least about 55%, or at least about 60%, of the patient population indicates that the TNFα inhibitor is an effective TNF inhibitor for the treatment of AS in the subject. In one embodiment, an BASDAI 50 response in at least about 23%, 24%, 25%, 26%, 27%, 28%, 29%, 30%, 31%, 32%, 33%, 34%. 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60% of the patient population indicates that the TNFa inhibitor is an effective TNF inhibitor for the treatment of AS in the subject.

The invention further provides a method of determining the efficacy of a TNFα inhibitor for treating ankylosing spondylitis (AS) in a subject comprising determining a Bath Ankylosing Spondylitis Disease Activity Index (BASDAI) 70 response of a patient population having AS and who was administered the TNFα inhibitor, wherein an BASDAI 70 response in at least about 10% of the patient population indicates that the TNFα inhibitor is an effective TNFα inhibitor for the treatment of AS in the subject. In one embodiment, an BASDAI 50 response in at least about 15%, at least about 20%, at least about 25%, at least about 30%, at least about 35%, at least about 40%, at least about 45%, of the patient population indicates that the TNFα inhibitor is an effective TNF inhibitor for the treatment of AS in the subject. In one embodiment, an BASDAI 50 response in at least about 23%, 24%, 25%, 26%, 27%, 28%, 29%, 30%, 31%, 32%, 33%, 34%. 35%, 36%, 37%, 38%, 39%, 40%, 41%, 42%, 43%, 44%, 45%, of the patient population indicates that the TNFa inhibitor is an effective TNF inhibitor for the treatment of AS in the subject.

The invention provides a method of treating AS in a subject comprising administering an effective TNFα inhibitor to the subject such that AS is treated, wherein the effective TNFα inhibitor was previously identified as resulting in an ASAS20 response in at least about 61% of a patient population having AS who was administered the TNFα inhibitor. In one embodiment, an ASAS20 response in at least about 27%, at least about 30%, at least about 35%, at least about 40%, at least about 45%, at least about 50%, at least about 55%, at least about 60%, at least about 65%, or at least about 70% of the patient population indicates that the TNFα inhibitor is an effective TNFα inhibitor for the treatment of AS in the subject. In one embodiment, an ASAS20 response in at least about 27%, 28%, 29%, 30%, 31%, 32%, 33%, 34%. 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, or 73% of the patient population indicates that the TNFα inhibitor is an effective TNFα inhibitor for the treatment of AS in the subject The invention also includes a method of determining the efficacy of a TNFα inhibitor for treating ankylosing spondylitis (AS) in a subject comprising determining a Assessment in Ankylosing Spondylitis (ASAS) response of a patient population having AS and who was administered the TNFα inhibitor, wherein an ASAS40 response in at least about 39% of the patient population indicates that the TNFα inhibitor is an effective TNFα inhibitor for the treatment of AS in the subject. In one embodiment, an ASAS40 response in at least about 40% of the patient population indicates that the TNFα inhibitor is an effective TNFα inhibitor for the treatment of AS in the subject. In one embodiment, an ASAS40 response in at least about 41% of the patient population indicates that the TNFα inhibitor is an effective TNFα inhibitor for the treatment of AS in the subject.

The invention also includes a method of determining the efficacy of a TNFα inhibitor for treating ankylosing spondylitis (AS) in a subject comprising determining a Assessment in Ankylosing Spondylitis (ASAS) response of a patient population having AS and who was administered the TNFα inhibitor, wherein an ASAS50 response in at least about 39% of the patient population indicates that the TNFα inhibitor is an effective TNFα inhibitor for the treatment of AS in the subject. In one embodiment, an ASAS50 response in at least about 40% of the patient population indicates that the TNFα inhibitor is an effective TNFα inhibitor for the treatment of AS in the subject.

The invention also includes a method of determining the efficacy of a human TNFα antibody or for treating ankylosing spondylitis (AS) in a subject comprising determining a Assessment in Ankylosing Spondylitis (ASAS) 70 response of a patient population having AS and who was administered the human TNFα antibody, or antigen-binding portion thereof, wherein an ASAS70 response in at least about 5% of the patient population indicates that the human TNFα antibody, or antigen-binding portion thereof, is an effective human TNFα antibody, or antigen-binding portion thereof, for the treatment of AS in the subject. In one embodiment, an ASAS70 response in at least about 20% of the patient population indicates that the human TNFα antibody, or antigen-binding portion thereof, is an effective human TNFα antibody, or antigen-binding portion thereof, for the treatment of AS in the subject. In one embodiment, an ASAS70 response in at least about 25% of the patient population indicates that the human TNFα antibody, or antigen-binding portion thereof, is an effective human TNFα antibody, or antigen-binding portion thereof, for the treatment of AS in the subject. In one embodiment, an ASAS70 response in at least about 30% of the patient population indicates that the human TNFα antibody, or antigen-binding portion thereof, is an effective human TNFα antibody, or antigen-binding portion thereof, for the treatment of AS in the subject. In one embodiment, an ASAS70 response in at least about 40% of the patient population indicates that the human TNFα antibody, or antigen-binding portion thereof, is an effective human TNFα antibody, or antigen-binding portion thereof, for the treatment of AS in the subject. In one embodiment, an ASAS70 response in at least about 5%, at least about 20%, at least about 24%, or at least about 40% of the patient population indicates that the TNFα inhibitor is an effective TNFα inhibitor for the treatment of AS in the subject. In one embodiment, an ASAS70 response in at least about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%. 35%, 36%, 37%, 38%, 39%, or 40% of the patient population indicates that the TNFα inhibitor is an effective TNFα inhibitor for the treatment of AS in the subject.

Numbers intermediate to any percentages recited herein, including those in the Examples, e.g., 61%, 62%, 63%. 64%, 65%, 66%, 67%, 68%, 69%, are also intended to be part of this invention. Ranges of values using a combination of any of the above recited values as upper and/or lower limits are intended to be included in the scope of the invention The invention may also include further comprising administering the effective human TNFα antibody, or antigen-binding portion thereof, described herein to a subject to treat AS.

Also encompassed in the invention is a method of treatment comprising administering a TNFα inhibitor shown to be efficacious according to the methods described herein and in the Examples. In one embodiment, the methods of the invention comprise administering the TNFα inhibitor to the subjects of a patient population and determining the efficacy of the TNFα inhibitor by determining changes, improvements, measurements, etc., using AS indices known in the art, in the patient population in comparison to the Examples set forth below. For example, the invention further provides a method of treating AS in a subject comprising administering an effective TNFα inhibitor to the subject such that AS is treated, wherein the effective TNFα inhibitor was previously identified as resulting in a BASDAI 50 response in at least about 60% of a patient population having AS and who was administered the TNFα inhibitor.

It should be noted that the Examples provided herein represent different methods of determining the efficacy of a TNFα inhibitor, such as a human TNFα antibody, or antigen-binding portion thereof. As such, data and results described in the Examples section which shows efficacy of a TNFα inhibitor, e.g., ability to treat AS, are included in the methods of determining efficacy of the invention.

Time points for determining efficacy will be understood by those of skill in the art to depend on the type of efficacy being determined, e.g., induction of partial remission. In one embodiment, measurements in scores, e.g., an improvement in the ASAS20 response, may be measured against a subject's baseline score. Generally, a baseline refers to a measurement or score of a patient before treatment, i.e. week 0. Other time points may also be included as a starting point in determining efficacy, however.

Patient populations described in the methods of the invention are generally selected based on common characteristics, such as, but not limited to, subjects diagnosed with AS. Such a patient population would be appropriate, for example, for determining the efficacy of the TNFα inhibitor for inducing partial remission in AS in the given patient population. In one embodiment, the patient population is an adult population.

In one embodiment, the methods of the invention for determining whether a TNFα inhibitor is an effective TNFα inhibitor, include determining changes, improvements, measurements, etc., in AS using appropriate indices described herein, e.g., ASAS responses, BASDAI, from a patient population who has already been administered the TNFα inhibitor. Such a patient population may be pre-selected according to common characteristics, e.g., AS, and may have already been given the TNFα inhibitor. Administration of the TNFα inhibitor may or may not be performed by the same person of ordinary skill who is determining the efficacy of the TNFα inhibitor in accordance with the teachings of the specification.

Methods of the invention relating to determining efficacy, i.e., determining whether a TNFα inhibitor is an effective TNFα inhibitor, may also be applied to specific patient populations within the overall patient population who together have specific, common characteristics, i.e., a subpopulation. In addition, while the above methods are described in terms of patient populations, methods of efficacy described herein may also be applied to individual subjects.

The Examples and discoveries described herein are representative of a TNFα inhibitor, i.e., adalimumab, which is effective for treating AS, including reducing pain and fatigue and inducing partial remission of AS. As such, the studies and results described in the Examples section herein may be used as a guideline for determining the efficacy of a TNFα inhibitor, i.e., whether a TNFα inhibitor is an effective TNFα inhibitor for the treatment of AS. In one embodiment, methods of determining efficacy described herein may be used to determine whether a TNFα inhibitor is bioequivalent to another TNFα inhibitor.

The present invention is further illustrated by the following examples which should not be construed as limiting in any way.

EXAMPLES

Example 1

Adalimumab in the Treatment of Active Ankylosing Spondylitis

Results of an Open-Label, 52-Week Trial

Tumor necrosis factor (TNF) antagonists infliximab and etanercept have shown efficacy in the treatment of ankylosing spondylitis (AS). Adalimumab (Abbott Laboratories) is a fully human, anti-TNF monoclonal antibody that reduces the signs and symptoms and progression of disease of rheumatoid arthritis and has been evaluated in AS over 20 weeks.

The objective of this study was to examine the potential therapeutic effects of adalimumab in NSAID-refractory AS patients who were treated for 52 weeks (Ann Rheum Dis 2005; 64(Suppl III):316). To further this objective, fifteen patients were enrolled (patient characteristics are detailed in Table 1). All patients suffered from spinal pain, and 4 patients also had peripheral arthritis. Adalimumab 40 mg was administered subcutaneously every other week (eow). Clinical outcome assessments included disease activity (BASDAI), function (BASFI), metrology (BASMI), patient's and physician's global and nocturnal assessments of pain (NRS), peripheral joint assessment, Maastricht enthesitis score, quality of life (SF-36), and C-reactive protein (CRP). The primary endpoint of this study was improvement of disease activity (BASDAI 50%) at Week 12. Outcome parameters are listed in Table 2.

TABLE 1

| Patient Characteristics. | |
|---|---|
| Number of patients (n) | 15 |
| Male/female (n) | 9/6 |
| Mean age, years (range) | 40 (19-55) |
| Mean disease duration, years (range) | 11 (2-33) |
| HLA-B27 positive | 86% |
| Mean BASDAI (range) | 6.6 (4.7-8.5) |
| Patients with joint involvement (n) | 4 |

TABLE 2

| Outcome Parameters. | | | | |
|---|---|---|---|---|
| | Baseline | Week 2 | Week 12 | Week 52 |
| BASFI | 6.3 | 5.1 | 4.3 | 3.7 |
| BASMI | 4.5 | 3.8 | 3.9 | 3.4 |
| General Pain | 7.4 | 5.1 | 4.1 | 3.4 |
| Nocturnal Pain | 7.3 | 4.7 | 4.0 | 3.2 |
| Patient's global | 7.3 | 5.0 | 4.3 | 3.1 |

Thirteen patients completed the 52-week therapy. One patient withdrew after 8 weeks for personal reasons; and the other patient withdrew because of inefficacy and remitting minor infections at Week 28.

At Week 52, the BASDAI showed a significant improvement (see FIG. 1). For example, at 52 weeks, over 75% of patients treated with adalimumab had achieved a BASDAI20 response, about 60% had achieved a BASDAI50 response, and more than 45% had achieved a BASDAI70 response.

Similar levels of improvement were achieved in applying the Assessment of Ankylosing Spondylitis (ASAS) working group improvement criteria (see FIG. 2). At 52 weeks, about 73% of patients treated with adalimumab had achieved an ASAS20 response, about 70% achieved an ASAS40 response, and about 40% achieved an ASAS70 response.

In addition, the CRP, BASFI, patient's and physician's global assessments, general and nocturnal assessments of pain (NRS), BASMI, morning stiffness (BASDAI Question 4 and 5) and the Physical Component Summary (PCS) of SF-36 improved significantly. Adalimumab was well-tolerated, and no serious infections occurred during the study. In this open-label study, adalimumab showed significant and sustained improvement of spinal symptoms in active AS over 1 year.

Example 2

Adalimumab Reduces Fatigue in Patients with Active Ankylosing Spondylitis (AS)

Fatigue, defined as enduring, subjective sensation of generalized tiredness or exhaustion, has been increasingly recognized as an important outcome measure in AS (Dagfinrud et al. *Arth Rheum* 2005; 53(1):5-11; Jones S D et al. *J Rheumatol* 1996; 23(3):487-90; Haywood H L et al. *Rheumatol* 2002; 41:1295-1302; Ward M M. *Arth Care Res* 1999; 12:247-55; Van Tubergen et al. *Arth Rheum* 2002; 27(1):8-16). It has been reported that 65% of people living with AS describe fatigue as a major symptom from time to time (Jones S D et al. *J Rheumatol* 1996; 23(3):487-90). The objective of this study was to evaluate the impact of adalimumab therapy (a TNF antagonist) on fatigue in active AS patients.

Overview

This phase III, double-blind, randomized, placebo-controlled trial was conducted at 11 sites in Canada (study design is shown in FIG. 3). The study enrolled active AS patients with an inadequate response to at least one NSAID. The study included a 24-week study period of 40 mg adalimumab subcutaneous (sc) injection every other week (eow) or placebo. There was an early escape option to open label 40 mg adalimumab sc eow at Weeks 12, 16, or 20. Patients completed a questionnaire on disease activity (BASDAI [Bath Ankylosing Spondylitis Disease Activity Index]). Fatigue was assessed by patient self-reported questionnaires, including FACIT-Fatigue, BASDAI Fatigue item, and SF-36 Vitality domain.

Instruments for Fatigue Assessments

FACIT-Fatigue is a widely used measure of fatigue in chronic illnesses. This measure contains 13 items pertaining to the past 7 days to be rated on a 5-point Likert scale. Scores range from 0-52, with higher scores representing less fatigue. A 3-point or more change is considered clinically meaningful (Cella et al. *Cancer* 2002; 94:528-538; and Cella et al. *J Clin Oncol* 2003; 21:366). FACIT-Fatigue was administered at Baseline and at Weeks 2, 12, and 24.

The BASDAI scale is widely used in clinical studies to evaluate AS disease activity. The BASDAI is a six-item measure of disease activity and includes questions on fatigue, spinal pain, peripheral arthritis, enthesitis, and duration and severity of morning stiffness. The BASDAI scale has six items pertaining to the past 7 days on a 10-cm visual analog scale (VAS). Fatigue is the first item on the BASDAI scale, asking the subject to rate "overall degree of tiredness" during the past 7 days on a 10-cm VAS. BASDAI Fatigue Item scores range from 0-10, with lower scores representing less fatigue. BASDAI was administered at Baseline and at Weeks 2, 4, 8, 12, 16, 20, and 24

SF-36 is a widely applied instrument for measuring health status, and consists of 8 domains: physical function, bodily pain, role limitations-physical, general health, vitality, social function, role limitations-emotional, and mental health. The Vitality domain has four items to measure energy level and fatigue. SF-36 has a 4-week recall period, and domain scores range from 0-100, with higher scores reflecting better health status. A 5-10 point change in domain scores is considered clinically meaningful (Kosinski M et al. *Arth Rheum* 2000; 7:1478-1487). SF-36 also contains 2 summary scores, the mental component summary (MCS) and the physical component summary (PCS); a 2.5-5 point change in summary scores is considered clinically meaningful (Kosinski M et al. *Arth Rheum* 2000; 7:1478-1487). SF-36 was administered at Baseline and at Weeks 12 and 24.

Patient disposition at Week 24 is shown in Table 3. Baseline demographics and disease activity are shown in Table 4. Patient-Reported Fatigue and Health-Related Quality of Life (HRQL) Scores at Baseline are shown in Table 5.

TABLE 3

Patient Disposition at Week 24

|  | Placebo (N = 44) n (%) | Adalimumab 40 mg eow (N = 38) n (%) |
|---|---|---|
| Subjects Randomized | 44 | 38 |
| Subjects Treated | 44 | 38 |
| Subjects Completing Week 24 | 44 (100) | 38 (100) |
| Prematurely terminated at Week 24 | 2 (4.5) | 0 |
| AE | 0 | 0 |
| Withdrew consent | 1 (2.3) | 0 |
| Lost to follow-up | 0 | 0 |
| Other | 1 (2.3) | 0 |

TABLE 4

Baseline Demographics and Disease Activity

|  | Placebo (N = 107) n (%) | Adalimumab 40 mg eow (N = 208) n (%) | p-value |
|---|---|---|---|
| Age (years) | 43.4 | 41.7 | 0.220a |
| Sex (males) | 79 (73.8) | 157 (75.5) | 0.784b |
| Race (Whites) | 99 (92.5) | 202 (97.1) | 0.050, b |
| Weight (kg) | 79.8 | 81.9 | 0.320 |
| HLA-B27 positive | 85 (79.4) | 163 (78.4) | 0.960b |
| Duration of AS (years) | 10.0 | 11.3 | 0.261a |
| BASDAI score | 6.3 | 6.3 | 0.633a |

TABLE 5

Patient-Reported Fatigue and Health-Related Quality of Life (HRQL) Score at Baseline*

|  | Placebo (N = 44) | Adalimumab 40 mg eow (N = 38) | p-value |
|---|---|---|---|
| FACIT-Fatigue | 23.6 (+9.9) | 24.4 (+10.8) | 0.770 |
| BASDAI Fatigue Item | 6.9 (+1.9) | 6.3 (+2.3) | 0.357 |
| SF-36 Vitality Domain | 34.6 (+18.4) | 30.4 (+17.9) | 0.325 |
| SF-36 PCS | 32.8 (+7.3) | 32.9 (+8.3) | 0.868 |
| SF-36 MCS | 41.6 (+10.0) | 42.8 (+9.5) | 0.517 |

*Mean + standard deviation

Data from the study is shown below. Patients with active AS experienced fatigue symptom and impairment in physical functioning at Baseline. Compared with placebo, adalimumab treatment demonstrated statistically significant improvement in disease activity (as measured by BASDAI, see Table 6)).

TABLE 6

Change from Baseline to Weeks 12 and 24
in Disease Activity-BASDAI Score

Mean change in BASDAI score*

|  | Placebo | Adalimumab |
|---|---|---|
| Week 12 | −0.51 | −2.04** |
| Week 24 | −0.37 | −1.99** |

*Mean change from baseline (LOCF).
**Statistically significant at p ≤ 0.01 level, p-value for difference between therapies from ANCOVA.

After 12 and 24 weeks of adalimumab therapy, patients reported statistically significant and clinically meaningful improvements in fatigue symptom and functioning compared with placebo (FACIT-Fatigue scores for the two treatment groups are shown in Table 7 and FIG. 4).

TABLE 7

Change from Baseline to Weeks 12 and 24 in FACIT-Fatigue Score

Mean change in FACIT-Fatigue score†

|  | Placebo | Adalimumab |
|---|---|---|
| Week 12 | 1.7 | 7.0** |
| Week 24 | 2.5 | 7.8* |

†Mean change from baseline (LOCF).
*, **Statistically significant at p ≤ 0.05 and p ≤ 0.01 levels, respectively.
Minimum Important Difference = 3
Cella et al. *Cancer* 2002; 94:528-538
Cella et al. *J Clin Oncol* 2003; 21:366-373.

A statistically significant difference in BASDAI Fatigue Item Score was seen between the placebo and adalimumab treatment groups at Weeks 12 and 24, as shown in Table 8 and FIG. 5.

TABLE 8

Change from Baseline to Weeks 12 and 24 in
BASDAI Fatigue Item Score

Mean change in BASDAI-Fatigue score†

|  | Placebo | Adalimumab |
|---|---|---|
| Week 12 | −0.5 | −1.7** |
| Week 24 | −0.5 | −1.9** |

†Mean change from baseline (LOCF).
**Statistically significant at p ≤ 0.01 level, respectively.

Statistically significant improvements were also seen in the adalimumab treatment group compared with placebo in the SF-36 Vitality Domain Score (Table 9 and FIG. 6), the SF-36 PCS Score (Table 10), and the SF-36 MCS Score (Table 11).

TABLE 9

Change from Baseline to Weeks 12 and 24 in
SF-36 Vitality Domain Score

Mean change in SF-36 Vitality Domain Score†

|  | Placebo | Adalimumab |
|---|---|---|
| Week 12 | 1.3 | 17 |
| Week 24 | 2.8 | 18.1 |

†Mean change from baseline (LOCF).
Minimum Important Difference = 10
Kosinski M et al. *Arth Rheum* 2000; 7:1478-1487.

TABLE 10

Change from Baseline in Weeks 12 and 24
in SF-36 PCS Score

Mean change in SF-36 PCS Score†

|  | Placebo | Adalimumab |
|---|---|---|
| Week 12 | 0.9 | 7.8*** |
| Week 24 | 1.1 | 6.1*** |

†Mean change from baseline (LOCF).
***Statistically significant at p ≤ 0.001 level.
Minimum Important Difference = 3
Kosinski M et al. *Arth Rheum* 2000; 7:1478-1487.

TABLE 11

Change from Baseline in Weeks 12 and 24
in SF-36 MCS Score

SF-36 MCS Score†

|  | Placebo | Adalimumab |
|---|---|---|
| Week 12 | 0.0 | 5.4 |
| Week 24 | 1.1 | 6.1 |

†Mean change from baseline (LOCF).
Minimum Important Difference = 3
Kosinski M et al. *Arth Rheum* 2000; 7:1478-1487.

In conclusion, these results show that adalimumab treatment may reduce fatigue and improve functioning in AS patients.

Example 3

Major Clinical Response and Partial Remission in Ankylosing Spondylitis Subjects Treated with Adalimumab Study H Ankylosing Spondylitis (AS) is a common inflammatory rheumatic disease that produces progressive spinal stiffness and restriction of mobility. Tumor necrosis factor (TNF) is thought to play a major role in the pathogenesis of AS. No trial of a disease-modifying antirheumatic drug (DMARD) has yielded consistent positive results for the treatment of AS.

Adalimumab is a fully human monoclonal antibody targeting TNF, currently approved for the treatment of rheumatoid arthritis and psoriatic arthritis in the US and Europe, and currently pending approval from the FDA and EMEA for AS. The objective of the study described herein was to investigate the ability of adalimumab to effect a major clinical response and partial remission in subjects with ankylosing spondylitis. Partial remission is defined as a value of <20 on a 0-100 VAS scale in each of the 4 ASAS domains: Pain (Total Back Pain

[TBP]), Function (Bath AS Functional Index [BASFI], Patient's Global Assessment (PGA) of disease activity, and Inflammation (Bath AS Disease Activity Index [BASDAI] questions 5 and 6).

Study H was a phase III, randomized, placebo-controlled, double-blind, multi-center study designed to assess the efficacy and safety of adalimumab in the treatment of active AS in subjects who had an inadequate response, or were intolerant to, treatment with at least one nonsteroidal anti-inflammatory drug (NSAID). Patients may have also had inadequate response to at least one DMARD. Thus, the study included subjects who had failed previous conventional therapy for AS.

Study H was a 2-year study in which subjects were randomized in a 2:1 ratio to receive either 40 mg subcutaneous (sc) doses of adalimumab or placebo every other week (eow). After the initial 24-week blinded period, patients had the option to participate in a subsequent 80-week open label extension. The study design of Study H is outlined in FIG. 7. Subjects who failed to achieve an Assessment in Ankylosing Spondylitis (ASAS) 20 response at or after Week 12 were eligible for open-label early escape therapy (EET) with adalimumab 40 mg sc eow. Subjects receiving early escape therapy were treated as nonresponders at all subsequent visits. All patients were assessed at Weeks 2, 4, 8, 12, 16, 20, and 24.

Patient inclusion criteria were inadequate response to at least one NSAID, and active AS, defined by fulfillment of at least 2 of the following 3 criteria: Bath AS Disease Activity Index (BASDAI) score ≥4, Visual Analog Scale (VAS) score for Total Back Pain (TBP)≥4, and morning stiffness ≥1 hour. Primary outcome measures were assessed at Weeks 12 and 24. Primary outcome measures include ASAS Partial Remission Criteria (value of <20 on a 0-100 scale in each of the 4 ASAS20 domains [Patient Global Assessment, Total Back Pain, Bath AS Functional Index, Bath AS Disease Activity Index questions 5 and 6]), and Major Clinical Response. ASAS40 and ASAS 5/6 outcomes have both been considered as candidate measures for determining Major Clinical Response. ASAS40 criteria represent a 40% improvement in 5 of 6 domains, without a 20% worsening in the sixth domain. ASAS 5/6 criteria represent a 20% improvement in 5 of 6 domains, without a 20% worsening in the sixth domain. Domains include: pain (TBP), function (BASFI), patient's Global Assessment (PGA) of disease activity, inflammation (BASDAI questions 5 & 6), spinal mobility (Bath AS Metrology Index [BASMI]), and C-reactive protein (CRP).

Results

A total of 315 subjects (adalimumab, n=208; placebo, n=107) were enrolled. Baseline characteristics were similar between subjects in each treatment arm. Baseline demographics are shown in Table 12, and the disposition of subjects enrolled in the study is shown in Table 13.

TABLE 12

Baseline Demographics

|  | Placebo (N = 107) n (%) | Adalimumab 40 mg eow (N = 208) n (%) |
|---|---|---|
| Mean Age (years) | 43.4 | 41.7 |
| Sex (males) | 79 (73.8) | 157 (75.5) |
| Race (Whites) | 99 (92.5) | 202 (97.1) |
| Mean Weight (kg) | 79.7 | 81.9 |
| HLA-B27 (positive) | 85 (79.4) | 163 (78.4) |
| Mean Duration of AS (years) | 10.0 | 11.3 |

TABLE 13

Disposition of Subjects

|  | Placebo (%) | Adalimumab 40 mg eow N (%) |
|---|---|---|
| Subjects Randomized | 107 | 208 |
| Subjects Treated | 107 | 208 |
| Subjects Completing Week 12 | 103 (96.3) | 204 (98.1) |
| Subjects Completing Week 24 | 101 (94.4) | 195 (93.8) |
| Prematurely Terminated at Week 12 | 4 (3.7) | 4 (1.9) |
| AE | 2 (1.9) | 2 (1.0) |
| Withdrew Consent | 0 | 2 (1.0) |
| Lost to Follow Up | 1 (0.9) | 0 |
| Other | 2 (1.9) | 2 (1.0) |
| Prematurely Terminated at Week 24 | 6 (5.6) | 13 (6.3) |
| AE | 2 (1.9) | 5 (2.4) |
| Withdrew Consent | 1 (0.9) | 5 (2.4) |
| Lost to Follow Up | 1 (0.9) | 2 (1.0) |
| Other | 4 (3.7) | 4 (1.9) |

The number of subjects who met the ASAS partial remission criteria was significantly ($p \leq 0.001$) higher for the adalimumab group vs. placebo group at Week 12 (20.7% vs. 3.7%) and at Week 24 (22.1% vs. 5.6%). Adalimumab vs. placebo subjects who met the ASAS5/6 criteria were 48.6% vs. 13.1% ($p \leq 0.001$) at Week 12, and 44.7% vs. 12.1% ($p \leq 0.001$) at Week 24, respectively. The percentage of ASAS40 responders in adalimumab patients was statistically significantly higher compared to placebo responders at Week 12 (40.9% vs. 14.0%) and at Week 24 (39.4% vs. 14.0%), respectively ($p \leq 0.001$, difference between therapies from ANCOVA calculated using Pearson's Chi-square test). The onset of improvement was rapid and sustained, as shown in FIG. 8 (ASAS40 response), as an improvement was seen within 2 weeks of administration of adalimumab.

Adverse events (AE), serious AEs, and severe AEs were comparable between both groups, as shown in Table 14. One serious infectious AE was present in the placebo group. The adalimumab group had no incidence of death, malignant neoplasm, or serious infectious AE.

TABLE 14

Treatment-emergent Adverse Events (AEs) Through Week 24[†]

| Patients with: | Placebo (N = 107) n (%) | Adalimumab 40 mg eow (N = 208) n (%) |
|---|---|---|
| Any AE | 66 (61.7) | 163 (78.4)** |
| Serious AE | 3 (2.8) | 6 (2.9) |
| Severe AE | 4 (3.7) | 6 (2.9) |
| AE leading to discontinuation of study drug | 2 (1.9) | 4 (1.9) |
| AE at least possibly drug-related | 18 (16.8) | 74 (35.6)*** |
| Infectious AE | 24 (22.4) | 70 (33.7) |
| Serious infectious AE | 1 (0.9) | 0 (0.0) |
| Drug hypersensitivity reaction | 1 (0.9) | 1 (0.4) |

[†]During administration of blinded study medication.
, *Statistically significant at the $p = 0.01$ and $p = 0.001$ levels, respectively.

Conclusions

Treatment with adalimumab was able to induce both a major clinical response and partial remission over a 24-week period in subjects with AS. Adalimumab was generally safe and well-tolerated. Furthermore, response rates to adalimumab were rapid, as ASAS40 response rates improved within the first 2 weeks of treatment.

Example 4

Efficacy of Adalimumab in Active Ankylosing Spondylitis (AS)

Results of the Canadian AS Study

Ankylosing spondylitis (AS) is a common inflammatory rheumatic disease that produces progressive spinal stiffness and restriction of mobility. Tumor necrosis factor (TNF) is thought to play a major role in the pathogenesis of AS. No established disease-modifying antirheumatic drug (DMARD) is presently available for the treatment of AS. The purpose of the study described herein was to evaluate the efficacy and safety of adalimumab vs. placebo in patients with active AS.

A 2-year, randomized, placebo-controlled, double-blind, Phase III trial was conducted at 11 sites in Canada. Patients with active AS who had an inadequate response to at least one NSAID or DMARD were eligible to enroll. The study design is outlined in FIG. 3. Patients were randomized to receive either placebo or adalimumab 40 mg subcutaneously (sc) every other week (eow) during an initial 24-week, double-blind period. Patient inclusion criteria were as follows: patients were ≥18 years old, patients had inadequate response to at least one NSAID, and patients had active AS, defined by fulfillment of at least 2 of the following 3 criteria: BASDAI (Bath Ankylosing Spondylitis Disease Activity Index) score ≥4, Visual Analog Scale (VAS) score for Total Back Pain ≥4, morning stiffness ≥1 hour. Patient exclusion criteria included the following: previously received anti-TNF treatment, radiological evidence of total spinal ankylosis (bamboo spine), use of previous DMARD within 4 weeks of Baseline (other than methotrexate, sulfasalazine, or hydroxychloroquine), intra-articular joint injection with corticosteroids within 4 weeks of Baseline, and use of other biologics or investigational therapy within 6 weeks of Baseline. Patients not achieving an ASAS20 (ASsessment in Ankylosing Spondylitis 20) response (calculated by the site) after 12 weeks were eligible, per the protocol, for early escape therapy (EET) of open-label 40 mg adalimumab eow. Any patient receiving EET was treated as a nonresponder at all subsequent visits in the statistical analysis.

Primary endpoints of the study were as follows: ASAS20 at Week 12, ASAS International Working Group Criteria, pain (Total Back Pain [TBP]), function (Bath AS Functional Index [BASFI]), Patient's Global Assessment (PGA) of disease activity, and inflammation (BASDAI questions 5 & 6). Secondary endpoints were ASAS20 at Week 24, BASDAI 20/50/70 at 12 and 24 weeks, ASAS50 and ASAS70 responses at 12 and 24 weeks, and PGA of disease activity at 12 and 24 weeks.

Results

A total of 82 patients (44 placebo, 38 adalimumab) were enrolled. 80 (98%) patients completed the 24-week period. The 2 patients who did not complete the 24-week period were from the placebo group. The 2 withdrawals from the 24 week period were not related to adverse events. At Week 12, 28 patients randomized to placebo and 20 patients randomized to adalimumab entered the EET group (64% vs. 53%, respectively). At Week 20, 36 patients randomized to placebo and 23 patients randomized to adalimumab entered the EET group (82% vs. 61%, respectively). Baseline characteristics were similar between treatment groups, as shown in Table 15.

TABLE 15

Baseline Demographics

|  | Placebo (N = 44) | Adalimumab 40 mg eow (N = 38) |
|---|---|---|
| Mean age (years) | 40.0 | 41.9 |
| Race (% Caucasian) | 42 (95.5) | 37 (97.4) |
| Sex (% male) | 36 (81.8) | 29 (76.3) |
| Mean weight (kg) | 78.2 | 76.1 |
| Mean Duration of AS (years) | 12.1 | 14.5 |

The number of DMARDs at Baseline was likewise similar among treatment groups, as shown in Table 16.

TABLE 16

DMARDs at Baseline

|  | Placebo (N = 44) | Adalimumab 40 mg eow (N = 38) |
|---|---|---|
| Baseline DMARD use† | 9 (20.5) | 6 (15.8) |
| Methotrexate† | 4 (9.1) | 4 (10.5) |
| Dose (mg/week)* | 18.8 ± 894 | 2000 ± 0 |
| Sulfasalazine† | 5 (11.4) | 3 (7.9) |
| Dose (mg/day)* | 2400 ± 894 | 2000 ± 0 |
| Leflunomide† | 0 | 0 |
| Hydroxychloroquine† | 3 (6.8) | 0 |

The ASAS20 response was higher in adalimumab (47%) vs. placebo (27%) at Week 12. The number of patients achieving ASAS50 and ASAS70 responses at Week 12 was statistically significantly higher for adalimumab patients compared to placebo patients (data is shown in Table 17).

TABLE 17

ASAS20/50/70 Scores at Week 12†

|  | % of Patients | | |
|---|---|---|---|
|  | ASAS20 | ASAS50 | ASAS70 |
| Placebo | 27.3 | 6.8 | 2.3 |
| Adalimumab | 47.4 | 39.5*** | 21.1* |

†Imputed.
*, ***Statistically significant at p = 0.05 and 0.001 levels, respectively.

Additionally, the ASAS20 response for adalimumab vs. placebo was rapid and was statistically significant (p≤0.01) at Weeks 2, 4, 8, 16, and 20. Adalimumab patients showed significantly greater improvement in TBP, BASFI, PGA and Inflammation scores at Week 12 than did placebo patients (data is shown in Table 18).

TABLE 18

TBP, BASFI, PGA, and Inflammation Scores at Week 12†

|  | % Change from Baseline | | | |
|---|---|---|---|---|
|  | TBP | BASFI | PGA | Inflammation |
| Placebo | −8.1 | 0.5 | −5.0 | −6.0 |
| Adalimumab | −40.5** | −29.6** | −36.1** | −39.1* |

†Imputed.
*, **Statistically significant at p = 0.05 and 0.01 levels, respectively.

At Week 12, EET was chosen by 64% of placebo and 53% of adalimumab patients, and by 82% and 61% of patients, respectively, at Week 20. The observed ASAS20 responses at Week 24 in patients initially randomized to adalimumab and placebo were 60% and 73%, respectively. Response to EET was rapid and sustained in the placebo group. The ASAS20 response for those patients who switched to EET at Week 12 is shown in FIG. 9. Five adalimumab patients with an ASAS20 response at Week 8 had been assessed as nonresponders at Week 12 and were switched to open-label therapy. Four of these 5 had regained an ASAS20 response at Week 16 and maintained it through Week 24. The observed ASAS20 response time course is shown in FIG. 10.

Both groups had comparable incidence of adverse events (AEs), with none of these leading to discontinuation of the study drug. Adalimumab patients had more infectious AEs (14 [37%] vs. 8 [18%] placebo patients; mostly upper respiratory infections). There was no significant difference in serious adverse events (SAEs) between groups and no deaths occurred. Treatment-emergent adverse events (AEs) through Week 24 of the study are shown in Table 19, and adverse events with ≥5% incidence through week 24 are shown in Table 20.

TABLE 19

Treatment-Emergent Adverse Events (AEs) Through Week 24

|  | Placebo (N = 44) n (%) | Adalimumab 40 mg eow (N = 38) n (%) |
|---|---|---|
| Any AE | 30 (68.2) | 33 (86.8) |
| Serious AE | 0 (0.0) | 1 (2.6) |
| Severe AE | 3 (6.8) | 4 (10.5) |
| AE leading to discontinuation of study drug | 0 (0.0) | 0 (0.0) |
| AE at least possibly drug-related | 13 (29.5) | 12 (31.6) |
| Infectious AE | 8 (18.2) | 14 (36.8) |
| Serious infectious AE | 0 (0.0) | 1 (2.6) |

TABLE 20

Adverse Events ≥5% Incidence Through Week 24

|  | Placebo (N = 44) n (%) | Adalimumab 40 mg eow (N = 38) n (%) |
|---|---|---|
| Nasopharyngitis | 5 (11.4) | 7 (18.4) |
| Headache | 3 (6.8) | 5 (13.2) |
| Upper respiratory tract infection | 1 (2.3) | 5 (13.2) |
| Arthralgia | 5 (11.4) | 4 (10.5) |
| Injection site reaction | 4 (9.1) | 3 (7.9) |
| Dizziness | 2 (4.5) | 2 (5.3) |

Conclusions

Adalimumab was efficacious in reducing the signs and symptoms of active AS and was generally well-tolerated. The possibility of early escape therapy influenced the results beyond Week 8.

Example 5

Adalimumab Improves Health-Related Quality of Life in Patients with Active Ankylosing Spondylitis Study H Ankylosing Spondylitis (AS) is a common inflammatory disease that produces spinal stiffness and restriction of mobility. The clinical symptoms and subsequent disease progression of AS may result in functional limitations and impairment in HRQL. Tumor necrosis factor (TNF) has been reported to play a major role in the pathogenesis of AS. Adalimumab is a fully human monoclonal antibody targeting TNF, currently approved for the treatment of rheumatoid arthritis and psoriatic arthritis in the US and Europe. Adalimumab is currently pending approval from the FDA and EMEA for AS. Study H was a phase III, randomized, placebo-controlled, double-blind, multi-center study designed to assess the efficacy and safety of adalimumab in the treatment of active AS in subjects who had an inadequate response, or were intolerant to, treatment with at least one nonsteroidal anti-inflammatory drug (NSAID); patients may have had an inadequate response to at least one DMARD (disease modifying anti-rheumatic drug). The objective of the study described herein was to assess the effect of adalimumab in improving function and HRQOL in patients with active AS who were treated with adalimumab in Study H.

Subjects were randomized to either adalimumab 40 mg every other week or placebo for 24 weeks (study design for Study H is outlined in FIG. 7). An early escape option to open label 40 mg adalimumab sc eow was available at Week 12, or 16, or 20. Disease activity was evaluated using the Bath Ankylosing Spondylitis Disease Activity Index (BASDAI) patient-reported questionnaire. Assessment in AS (ASAS) 20 criteria was the primary efficacy measure. Functioning and HRQL were assessed by patient-reported questionnaires, including Bath AS Functional Index (BASFI), SF-36 (Short Form-36) and Ankylosing Spondylitis Quality of Life Questionnaire (ASQoL). Patient-reported questionnaires utilized in this study are described in greater detail below.

The BASDAI is a six-item measure of disease activity and includes questions on fatigue, spinal pain, peripheral arthritis, enthesitis, and duration and severity of morning stiffness. It is a well-established instrument widely used in clinical studies to evaluate AS disease activity. Items are related to the past 7 days and are answered on a 10 cm visual analogue scale (VAS), with score ranges from 0 (none) to 10 (very severe). Instrument was administered at Baseline, and at Weeks 2, 4, 8, 12, 16, 20 and 24.

The BASFI is a set of 10 questions designed to determine the degree of functional limitation in those with AS. Items are related to the past 7 days and are answered on a 10 cm visual analogue scale (VAS). The score ranges from 0 to 100, with lower scores reflecting less function limitation. Instrument was administered at Baseline, and at Weeks 2, 4, 8, 12, 16, 20 and 24.

SF-36 is a widely applied instrument for measuring health status and consists of 8 domains: physical function, bodily pain, role limitations-physical, general health, vitality, social function, role limitations-emotional, and mental health. The Recall period is 4 weeks, and domain scores range from 0-100, with higher scores reflecting better health status. A 5-10 point change in domain scores is considered clinically meaningful (Kosinski M et al. *Arth Rheum* 2000; 7:1478-1487). SF-36 also contains 2 summary scores, the mental Component summary (MCS) and the physical component summary (PCS); a 2.5-5 point change in summary scores is considered clinically meaningful (Kosinski M et al. *Arth Rheum* 2000; 7:1478-1487). This instrument was administered at Baseline, and at Weeks 12 and 24.

The ASQoL is a disease-specific instrument designed to measure HRQL in subjects with AS, developed on a needs-based model. Subjects are asked to answer 18 yes/no items concerning the impact of AS "at this moment". The ASQoL has a total score ranging from 0 to 18, with lower scores representing better AS-specific quality of life. The instrument has good reliability and construct validity across several different AS populations (Doward L C, et al. Ann Rheum Dis 2003; 62:20-26; Haywood K L, et al J Rheumatol 2003; 30:764-773; van Tubergen A et al. Arthritis Rheum 2002; 47:8-16; Marzo-Ortega H, et al. Arthritis Rheum 2001; 44(9): 2112-2117). The pre-specified minimum important difference (MID) has been suggested to be a change of 1-2 points, 10% of the total score (Haywood K L, et al J Rheumatol 2003; 30:764-773; Haywood K L, et al. Rheum 2002; 41:1295-1302). Assessments were made at Baseline and at Weeks 2, 12, and 24.

Results

A total of 315 subjects (adalimumab, N=208; placebo, N=107) were enrolled. The disposition of subjects and study completion rates are shown above in Table 13. At baseline, adalimumab and placebo arms had comparable demographic and disease characteristics, SF-36 (PCS, MCS), and ASQoL scores, as shown in Table 12 above. Functioning and HRQoL assessment at baseline is shown in Table 21. Baseline SF-36 PCS scores (placebo 31.7, adalimumab 33.1) were almost 20 points lower than the U.S. general population norm (50.0), indicating a substantial impairment of physical health status, while baseline mental health status measured by SF-36 MCS scores (placebo 44.7, adalimumab 43.5) were close to the population norm.

TABLE 21

Functioning and HRQoL Assessment at Baseline

|  | Placebo (N = 107) | Adalimumab 40 mg eow (N = 208) | p-value[†] |
|---|---|---|---|
| SF-36 PCS | 31.8 | 32.9 | 0.519 |
| ASQoL | 10.6 | 10.2 | 0.343 |
| SF-36 MCS | 44.4 | 43.4 | 0.407 |
| SF-36 Subscales |  |  | 0.495 |
| Physical Function | 45.5 | 47.9 | 0.524 |
| Role-Physical | 19.9 | 20.5 | 0.214 |
| Social Function | 53.4 | 57.2 | 0.323 |
| General Health | 41.0 | 43.4 | 0.491 |
| Bodily Pain | 29.8 | 31.7 | 0.544 |
| Vitality | 34.0 | 32.6 | 0.491 |
| Role-Emotional | 56.8 | 53.2 | 0.701 |
| Mental Health | 62.5 | 61.3 | 0.567 |
| BSDAI Fatigue | 6.7 | 6.5 | 0.846 |

*Unadjusted means
[†]Differences between treatment groups were assessed using analysis of variance with treatment group and baseline scores as covariates At week 12 and 24, adalimumab treatment demonstrated statistically significant ASAS20 response (the primary efficacy measurement) compared with placebo, and the onset of improvement by adalimumab was rapid and sustained (data is shown in FIG. 11). At Week 12, adalimumab patients showed statistically significantly greater improvement in SF-36 PCS scores than did placebo patients. These statistically significant improvements increased through Week 24. Change in SF-36 PCS scores for adalimumab patients well exceeded the MID value and suggested a sustained clinically important improvement; placebo groups did not achieve the MID for SF-36 PCS scores. The proportion of patients who achieved the MID in SF-36 PCS scores was statistically significant in adalimumab vs. placebo at 12 weeks (65.0 vs. 37.6, respectively, $p \leq 0.001$) and 24 weeks (67.3 vs. 39.6, respectively, $p \leq 0.001$) (data is shown in Table 22). Neither the adalimumab group nor the placebo group experienced any significant change in MCS scores at Week 12 or Week 24. The proportion of patients that achieved the MID in change of MCS scores was similar in both the adalimumab and placebo groups.

TABLE 22

Change from Baseline in SF-36 PCS Scores at 12 Weeks and 24 Weeks

|  | Mean Change from Baseline[†] | |
|---|---|---|
|  | Placebo | Adalimumab |
| Week 12 | 1.6 | 6.9*** |
| Week 24 | 1.9 | 7.4*** |

[†]LOCF
Minimum Important Difference = 3 (Kosinski M et al. Arth Rheum 2000; 7:1478-1487).
***Statistically significant at p = 0.001 level. p-value for difference between therapies from ANCOVA.

At both Weeks 12 and 24, patients treated with adalimumab showed statistically significant improvement in 7 out of the 8 subscales compared with those treated with placebo, including the 4 subscales that are most closely related to the SF-36 PCS (Physical Functioning, Role-Physical, Bodily Pain, and General Health) and 3 of the 4 subscales that are most closely related to the SF-36 MCS (Vitality, Social Functioning, and Role-Emotional) (12-Week data is shown in Table 23, 24-Week data is shown in Table 24). The differences at Weeks 12 and 24 are also considered to be clinically meaningful, based on the MID of 5-10 point change scores.

TABLE 23

Change from Baseline in SF-36 Domain Scores at 12 Weeks[†]

|  | Mean Change | |
|---|---|---|
|  | Placebo | Adalimumab |
| Physical Functioning | 3 | 11.8*** |
| Role-Physical | 7.9 | 25.3*** |
| Social Functioning | 6.3 | 8.7* |
| General Health | 1.4 | 8*** |
| Bodily Pain | 6.7 | 19.2*** |
| Vitality | 6.4 | 13.1** |
| Role-Emotional | 3.2 | 14.7* |
| Mental Health | 4.3 | 4.6 |

[†]LOCF unadjusted means
Differences between treatment groups were assessed using an analysis of covariance with treatment group and baseline scores as covariates.
*, , and * are statistically significant at the $p < 0.05$, $p < 0.01$, and $p < 0.001$ levels, respectively.

TABLE 24

Change from Baseline in SF-36 Domain Scores at 24 Weeks[†]

|  | Mean Change | |
|---|---|---|
|  | Placebo | Adalimumab |
| Physical Functioning | 4.2 | 13.2*** |
| Role-Physical | 9.2 | 27.6*** |
| Social Functioning | 6.5 | 12.2*** |
| General Health | 1.2 | 8.8*** |
| Bodily Pain | 7.1 | 20.7*** |
| Vitality | 5.6 | 14.7*** |
| Role-Emotional | 3.5 | 15.9* |
| Mental Health | 4.7 | 5.9 |

[†]LOCF unadjusted means
Differences between treatment groups were assessed using an analysis of covariance with treatment group and baseline scores as covariates.
*, , and * are statistically significant at the $p < 0.05$, $p < 0.01$, and $p < 0.001$ levels, respectively.

More adalimumab patients experienced a statistically significant improvement in BASFI compared with placebo patients at Week 12 and Week 24 (data is shown in Table 25).

TABLE 25

Change from Baseline in BASFI
Scores at 12 Weeks and 24 Weeks[†]

| | Mean Change at Baseline[‡] | |
|---|---|---|
| | Placebo | Adalimumab |
| Week 12 | −5.05 | −17.46*** |
| Week 24 | −5.16 | −18.7*** |

[†]LOCF
[‡]unadjusted means
***Statistically significant at the pp < 0.001, placebo vs. adalimumab.
p-value for differences between therapies from an ANCOVA with therapy and baseline values as a covariate.

At Week 12 and Week 24, adalimumab patients showed greater improvement in overall HRQL as measured by ASQoL scores when compared to placebo patients (data is shown in Table 26). The change in ASQoL scores exceeded the prior MID value and suggested a sustained clinically important improvement. The proportion of adalimumab patients that achieved the MID in ASQoL score was statistically significantly higher than the proportion of placebo patients. The proportion of patients who achieved the MID in ASQoL scores was statistically significant in adalimumab vs. placebo at 12 weeks (59.1 vs. 42.1, respectively, p<0.01) and 24 weeks (65.4 vs. 42.1, respectively, p<0.001).

TABLE 26

Change from Baseline in ASQoL
Scores at 12 Weeks and 24 Weeks[†]

| | Mean Change at Baseline[‡] | |
|---|---|---|
| | Placebo | Adalimumab |
| Week 12 | −1.0 | −3.1*** |
| Week 24 | −1.1 | −3.6*** |

[†]LOCF
[‡]unadjusted means
Minimum Important Difference = −2 (Haywood K.L. et al. J. Rheumatol. 2003; 30:764-773; Haywood K.L. et al. Rheum. 2002; 41:1295-1302).
***Statistically significant at the p = 0.001 level, p-value assessed using analysis of variance within treatment group and baseline scores as covariates.

Conclusions

These results suggest that adalimumab therapy may improve physical health status and overall HRQL in AS patients. After 12 and 24 weeks of adalimumab therapy, patients reported statistically significant and clinically meaningful improvements in physical functioning as measured by SF-36 PCS and BASFI compared with placebo. At 12 and 24 weeks, patients treated with adalimumab reported statistically significant and clinically meaningful improvements in overall HRQL as measured by ASQoL compared with those treated with placebo.

Example 6

Adalimumab Therapy Results in Significant Reduction of Signs and Symptoms in Subjects with Ankylosing Spondylitis The aim of the following study (Study II) was to assess the efficacy and safety of adalimumab in the treatment of AS. The study design of Study H is outlined in FIG. 7, and included a double-blind placebo-controlled 24 week study followed by a continuous open label study (shown in FIG. 7). Details regarding Study H are also provided in the above examples referencing this study, as well as below.

Inclusion criteria were the following: ≥18 years of age; AS based on modified New York criteria; inadequate response to ≥1 NSAID; and active AS, as diagnosed by 2 of the 3 following symptoms: Bath AS Disease Activity Index (BASDAI) score ≥4; Visual Analog Scale (VAS) score for Total Back Pain (TBP) ≥4; and Morning stiffness ≥1 hour. Patients not achieving an ASAS 20 response after 12 weeks were eligible for early escape therapy (EET) of open-label 40 mg adalimumab eow. Any patient receiving EET was treated as a nonresponder at all subsequent visits in the statistical analysis.

The primary endpoint for monitoring reduction of signs and symptoms was ASAS 20 at Week 12. Major secondary endpoints were ASAS 40, ASAS 5/6, and ASAS Partial Remission Criteria. Outcome measures were assessed at Weeks 12 and 24.

ASAS20 improvement criteria included assessment of patient global, pain, function, and inflammation, and required an improvement of ≥20% and ≥1 unit in at least 3 of these domains, without a worsening of ≥20% and ≥1 unit in the remaining domain (see Anderson et al. (2001) Arthritis Rheum 44:1876-1886).

ASAS 40 improvement criteria included an assessment of the same four domains as for ASAS20, and required an improvement of ≥40% and ≥2 units in at least 3 domains, with no worsening at all in the remaining domain (see Brandt et al. (2004) Ann Rheum 63:1438-1444).

ASAS 5/6 improvement criteria included an improvement of ≥20% in at least 5 of the following 6 domains: patient global, pain, function, inflammation, CRP, and spinal mobility (see Brandt et al. (2004) Ann Rheum 63:1438-1444).

ASAS partial remission criteria include a value of <2 units in all four of the following domains: patient global, pain, function, and inflammation (see Anderson et al. (2001) Arthritis Rheum 44:1876-1886).

Baseline demographics are shown in Table 12 above, and concomitant diseases or symptoms present at baseline are shown in Table 27.

TABLE 27

Concomitant Diseases or Symptoms at Baseline

| | Placebo<br>(N = 107)<br>n (%) | Adalimumab<br>40 mg eow<br>(N = 208)<br>n (%) |
|---|---|---|
| History of inflammatory bowel disease[†] | 6 (5.6) | 21 (10.1) |
| Peripheral arthritis[‡] | 44 (44.1) | 75 (36.1) |
| History of psoriasis[†] | 17 (15.9) | 16 (7.7) |
| History of uveitis[†] | 27 (25.2) | 68 (32.7) |

*No significant differences between groups except for psoriasis
[†]Stable for at least four weeks prior to Baseline
[‡]At least one SJC at Baseline Baseline disease activity is shown in Table 28. Concomitant Treatment at baseline is shown in Table 29. The disposition of subjects in the trial is shown above in Table 13. Patients receiving early escape open-label therapy are shown in Table 30.

TABLE 28

Baseline Disease Activity

|  | Placebo (N = 107) | Adalimumab 40 mg eow (N = 208) |
|---|---|---|
| BASDAI score* | 6.3 | 6.3 |
| BASDAI categories† < 4 | 12 (11.2) | 25 (12.0) |
| 4-6 | 30 (28.0) | 62 (29.8) |
| >6 | 65 (60.7) | 121 (58.2) |
| Total Back Pain VAS | 6.7 | 6.4 |
| Morning Stiffness | 6.7 | 6.7 |
| BASFI score* | 5.6 | 5.2 |
| CRP (mg/dL)* | 2.2 | 1.8 |
| Patients with elevated CRP†‡ | 75 (70.1) | 138 (66.3) |

*Mean
†n (%)
‡Normal CRP range ≤ 0.494 mg/dl

TABLE 29

Concomitant Treatment at Baseline

|  | Placebo (N = 107) | Adalimumab 40 mg eow (N = 208) |
|---|---|---|
| Baseline DMARD use* | 22 (20.6) | 40 (19.2) |
| Methotrexate | 8 (7.5) | 20 (9.6) |
| Sulfasalazine | 15 (14.0) | 26 (12.5) |
| Leflunomide | 1 (0.9) | 0 |
| Oral corticosteroids | 6 (5.6) | 25 (12.0) |
| NSAIDs | 84 (78.5) | 166 (79.8) |

*n (%)

TABLE 30

Patients Receiving Early Escape Open-label Therapy

| Visit | Placebo (N = 107) n (%) | Adalimumab 40 mg eow (N = 208) n (%) |
|---|---|---|
| Total | 74 (69.2) | 81 (38.9) |
| Week 12 | 55 (51.4) | 54 (26.0) |
| Week 14 | 11 (10.3) | 5 (2.4) |
| Week 16 | 6 (5.6) | 10 (4.8) |
| Week 18 | 0 (0.0) | 1 (0.5) |
| Week 20 | 2 (1.9) | 8 (3.8) |
| Week 22 | 0 (0.0) | 3 (1.4) |

A statistically significant change from baseline was observed between the adalimumab and placebo patient treatment groups in the following ASAS20 components: patient's global assessment of disease activity, total back pain, and inflammation. The baseline mean score for patient's global assessment of disease activity was 64.5 for the placebo treatment group and 63.2 for the adalimumab treatment group. The percentage change from baseline observed in the placebo group was 6.5 at Week 12, and 8.7 at Week 24 (N=107). The percentage change from baseline observed in the adalimumab group was −39.1 at Week 12, and −37.8 at Week 24 (N=208; difference between placebo vs. adalimumab is significant at p=0.001 level, determined by ANCOVA).

The baseline mean score for total back pain was 67.2 for the placebo treatment group and 64.6 for the adalimumab treatment group. The percentage change from baseline observed in the placebo group was −9.5 at Week 12 and −10.0 at Week 24 (N=107). The percentage change from baseline observed in the adalimumab group was −40.5 at Week 12, and −42.4 at Week 24 (N=208; difference between placebo vs. adalimumab is significant at p=0.001 level, determined by ANCOVA).

The baseline mean score for inflammation (the mean of BASDAI questions 5 and 6) was 6.7 for both the placebo and adalimumab treatment groups. The percentage change from baseline observed in the placebo group was −15.2 at Week 12 and −12.5 at Week 24 (N=107). The percentage change from baseline observed in the adalimumab group was −41.7 at Week 12, and −42.9 at Week 24 (N=208; difference between placebo vs. adalimumab is significant at p=0.001 level, determined by ANCOVA).

The mean change in ASAS 20, ASAS 40, and ASAS 5/6 from baseline at Week 12 and Week 24 is shown in Table 31. BASDAI 50 at Week 12 and Week 24 is shown in Table 32.

TABLE 31

ASAS20†, ASAS40‡, and ASAS 5/6‡

| | Mean Change from Baseline | | |
|---|---|---|---|
| | ASAS20 | ASAS40 | ASAS5/6 |
| Week 12 | | | |
| Placebo | 20.6 | 14.0 | 13.1 |
| Adalimumab | 58.2*** | 40.9*** | 48.6*** |
| Week 24 | | | |
| Placebo | 18.7 | 14.0 | 12.1 |
| Adalimumab | 50.5*** | 39.4*** | 44.7*** |

†Imputed;
‡LOCF
***Statistically significant at p < 0.001 level (ANCOVA)

TABLE 32

BASDAI 50

| | % of Patients | |
|---|---|---|
| | Placebo (N = 107) | Adalimumab (N = 208) |
| Week 12 | 15.9 | 45.2*** |
| Week 24 | 15.0 | 42.3*** |

***Statistically significant at p = 0.001 level (Pearson's Chi-Square test).
Patients with missing data at Weeks 12 and 24 are counted as non-responders.

The percentage of patients achieving partial remission at Week 12 and Week 24 is shown in Table 33. The mean change in BASDAI, BASFI, and BASAMI from baseline at Week 24 is shown in Table 34.

TABLE 33

Partial Remission‡

| | Partial Remission % of Patients† | |
|---|---|---|
| | Placebo (N = 107) | Adalimumab (N = 208) |
| Week 12 | 3.7 | 20.7*** |
| Week 24 | 5.6 | 22.1*** |

†LOCF;
‡Partial remission is defined as a value <20 on a 0-100 scale in each of the four ASAS domains.
***Statistically significant at p = 0.001 level (Pearson's Chi-Square test).

TABLE 34

BASDAI, BASFI, and BASMI at Week 24

|  | Mean change from Baseline | |
|---|---|---|
|  | Placebo | Adalimumab |
| BASDAI | −0.8 | −2.6*** |
| BASFI | −0.5 | −1.87*** |
| BASMI | 0.0 | −0.6 |

†LOCF
***Statistically significant at p < 0.001 level (ANCOVA)

A Subgroup Analysis of ASAS 20 responders with Total Spinal Ankylosis is shown in Table 35.

TABLE 35

Subgroup Analysis-Total Spinal Ankylosis

|  | ASAS20 Responders (% of Patients) | |
|---|---|---|
|  | Yes | No |
| Week 12 | | |
| Placebo | 0 (n = 5) | 21.6 (n = 102) |
| Adalimumab | 50 (n = 6) | 58.2 (n = 201) |
| Week 24 | | |
| Placebo | 0 (n = 5) | 19.6 (n = 102) |
| Adalimumab | 66.7 (n = 6) | 49.8 (n = 201) |

The Maastricht AS Enthesitis Score (MASES), which assesses the patients response to firm palpation at 13 points in the chest, hip, and foot regions, was measured at Weeks 12 and 24. Possible total scores range from 0-13, with a score of 0 indicating no pain, and a score of 1 indicating pain. Consequently, a decrease in MASES is representative of improvement. The mean baseline MASES was 6.7 in the placebo treatment group, and 6.3 in the adalimumab treatment group. The mean change from baseline MASES (LOCF) in the placebo group was −1.3 at Week 12 and −1.6 at Week 24 (N=106). The mean change from baseline MASES in the adalimumab group was −2.7 at Week 12 (N=204; statistically significant at p<0.05 vs. placebo as determined by ANCOVA), and −3.2 at Week 24 (N=205; statistically significant at p<0.01 vs. placebo as determined by ANCOVA).

Adverse events with a ≥5% incidence through Week 24 are shown in Table 36. Treatment-emergent adverse events through week 24 are shown in Table 37.

TABLE 36

Adverse Events ≥ 5% Incidence Through Week 24†

| MedDRA preferred term: | Placebo (N = 107) n (%) | Adalimumab 40 mg eow (N = 208) n (%) | P-value‡ |
|---|---|---|---|
| Nasopharyngitis | 8 (7.5) | 26 (12.5) | 0.249 |
| Injection site reaction | 3 (2.8) | 22 (10.6) | 0.015* |
| Headache | 9 (8.4) | 20 (9.6) | 0.838 |

†During administration of blinded study medication
‡Fischer's exact test (2 tail)
*Statistically significant at p ≤ 0.05 level

TABLE 37

Treatment-emergent Adverse Events (AEs) Through Week 24†

| Patients with: | Placebo (N = 107) n (%) | Adalimumab 40 mg eow (N = 208) n (%) | p-values‡ |
|---|---|---|---|
| Any AE | 66 (61.7) | 163 (78.4) | 0.002** |
| Serious AE | 3 (2.8) | 6 (2.9) | NS |
| Severe AE | 4 (3.7) | 6 (2.9) | NS |
| AE leading to discontinuation of study drug | 2 (1.9) | 4 (1.9) | NS |
| AE at least possibly drug-related | 18 (16.8) | 74 (35.6) | <0.001*** |
| Infections AE | 24 (22.4) | 70 (33.7) | NS |
| Serious infectious AE | 1 (0.9) | 0 (0.0) | NS |
| Drug hypersensitivity reaction | 1 (0.9) | 1(0.4) | NS |
| Malignant neoplasm | 0 (0.0) | 0(0.0) | NS |
| Death | 0 (0.0) | 0(0.0) | NS |

†During administration of blinded study medication
‡Only statistically significant p-values are shown
, *Statistically significant at the p = 0.01 and p = 0.001 levels, respectively (Pearson's Chi-Square test)

Laboratory tests were performed through Week 24. There were small changes in hemoglobin, platelets, neutrophils and lymphocyte counts in adalimumab-treated patients. Adalimumab patients had significantly higher levels of liver enzymes (ALT, AST) and total bilirubin compared with placebo; however, these changes were small. Baseline and maximum ALT values through Week 24 are shown in Table 38. Adalimumab patients also had a significantly greater decrease in C-reactive protein (CRP) at Weeks 12 and 24. The baseline mean CRP was 2.16 mg/dL in the placebo treatment group and 1.76 mg/dL in the adalimumab treatment group. The mean change from baseline (LOCF) in CRP (mg/dL) among patients in the placebo group was −0.08 at Week 12 and −0.06 at Week 24 (N=105). The mean change from baseline among patients in the adalimumab group was −1.28 at Week 12 and −1.25 at Week 24 (N=204; statistically significant vs. placebo at p≤0.001 level as determined by ANCOVA).

TABLE 38

Baseline and Maximum ALT Values Through Week 24

| Baseline ALT Value | Maximum ALT Value | | | |
|---|---|---|---|---|
|  | <1.5 × ULN n (%) | ≥1.5 × ULN-<3.0 × ULN n (%) | ≥3.0 × ULN-<8.0 × ULN n (%) | ≥8.0 × ULN n (%) |
| Placebo (N = 107) | | | | |
| <1.5 × ULN | 104 (97.2) | 2 (1.9) | 0 | 0 |
| ≥1.5 × ULN-<3.0 × ULN | 0 | 0 | 0 | 0 |
| ≥3.0 × ULN-<8.0 × ULN | 0 | 1 (0.9) | 0 | 0 |
| ≥8.0 × ULN | 0 | 0 | 0 | 0 |
| Adalimumab 40 mg eow (N = 208) | | | | |
| <1.5 × ULN | 175 (84.1) | 23 (11.1) | 2 (1.0) | 1 (0.5) |
| ≥1.5 × ULN-<3.0 × ULN | 1 (0.5) | 1 (0.5) | 3 (1.4) | 0 |
| ≥3.0 × ULN-<8.0 × ULN | 0 | 2 (1.0) | 0 | 0 |
| ≥8.0 × ULN | 0 | 0 | 0 | 0 |

Conclusions

Adalimumab was generally well tolerated in patients with active AS. The safety profile of adalimumab in the Study H Trial was consistent with that observed in RA and PsA trials. Adalimumab was effective in treating subjects with active AS. Adalimumab showed similar efficacy in patients with and without Total Spinal Ankylosis (TSA).

EQUIVALENTS

Those skilled in the art will recognize, or be able to ascertain using no more than routine experimentation, many equivalents to the specific embodiments of the invention described herein. Such equivalents are intended to be encompassed by the following claims. The contents of all references, patents and published patent applications cited throughout this application are incorporated herein by reference.

What is claimed:

1. A method of treating active ankylosing spondylitis (AS) in a subject having total spinal ankylosis comprising selecting a subject having active AS and total spinal ankylosis, and subcutaneously administering 40 mg of an isolated human anti-TNFα antibody to the subject once every other week, wherein the human anti-TNFα antibody comprises a light chain variable region (LCVR) comprising the amino acid sequence of SEQ ID NO: 1, and comprises a heavy chain variable region (HCVR) comprising the amino acid sequence of SEQ ID NO: 2.

2. The method of claim 1, wherein the human anti-TNFα antibody is adalimumab.

3. The method of claim 1, wherein the subject had an inadequate response to treatment with at least one NSAID.

4. A method of reducing signs and symptoms of ankylosing spondylitis (AS) in a subject having active AS and total spinal ankylosis, the method comprising selecting a subject having active AS and total spinal ankylosis and subcutaneously administering 40 mg of an isolated human anti-TNFα antibody to the subject once every other week, wherein the human anti-TNFα antibody comprises a light chain variable region (LCVR) comprising the amino acid sequence of SEQ ID NO: 1, and comprises a heavy chain variable region (HCVR) comprising the amino acid sequence of SEQ ID NO: 2.

5. The method of claim 4, wherein the human anti-TNFα antibody is adalimumab.

6. The method of claim 4, wherein the subject had an inadequate response to treatment with at least one NSAID.

* * * * *